United States Patent [19]

Nakamura et al.

[11] Patent Number: 5,105,269
[45] Date of Patent: Apr. 14, 1992

[54] IMAGING APPARATUS AND ENDOSCOPE APPARATUS WITH SELECTABLE WAVELENGTH RANGES

[75] Inventors: Kazunari Nakamura; Akira Takano, both of Hachioji, Japan

[73] Assignee: Olympus Optical Co., Ltd., Tokyo, Japan

[21] Appl. No.: 583,277

[22] Filed: Sep. 17, 1990

Related U.S. Application Data

[60] Division of Ser. No. 128,118, Nov. 30, 1987, and a continuation of Ser. No. 449,436, Dec. 11, 1989, Pat. No. 4,974,076.

[30] Foreign Application Priority Data

| Nov. 29, 1986 | [JP] | Japan | 61-284614 |
| Nov. 29, 1986 | [JP] | Japan | 61-284615 |
| Oct. 20, 1987 | [JP] | Japan | 62-266060 |
| Nov. 17, 1987 | [JP] | Japan | 62-290302 |

[51] Int. Cl.$^5$ .......................... H04N 7/10; H04N 5/30
[52] U.S. Cl. ........................ 358/98; 358/110; 128/6
[58] Field of Search ............ 358/98, 42, 113, 110; 128/4, 6

[56] References Cited

U.S. PATENT DOCUMENTS

| 4,074,306 | 2/1978 | Kakinuma et al. | 358/1 |
| 4,593,313 | 6/1986 | Nagasaki et al. | 358/98 |
| 4,608,599 | 8/1986 | Kaneko et al. | 358/113 |
| 4,621,284 | 11/1986 | Nishioka et al. | 358/98 |
| 4,656,508 | 4/1987 | Yokota | 358/98 |
| 4,667,229 | 5/1987 | Cooper et al. | 358/98 |
| 4,679,068 | 7/1987 | Lillquist et al. | 358/44 |
| 4,717,952 | 1/1988 | Kohayakawa et al. | 358/113 |
| 4,720,178 | 1/1988 | Nishioka et al. | 350/401 |
| 4,740,837 | 4/1988 | Yanagisawa et al. | 358/98 |
| 4,807,026 | 2/1989 | Nishioka et al. | 358/98 |

FOREIGN PATENT DOCUMENTS

| 2506630 | 8/1976 | Fed. Rep. of Germany . |
| 2723243 | 11/1978 | Fed. Rep. of Germany . |
| 003033 | 1/1981 | Japan . |
| 139237 | 8/1984 | Japan . |
| 53918 | 3/1985 | Japan . |

*Primary Examiner*—John K. Peng
*Attorney, Agent, or Firm*—Armstrong, Nikaido, Marmelstein, Kubovcik & Murray

[57] ABSTRACT

The imaging apparatus and endoscope apparatus comprise an image forming optical system forming the image of an object to be imaged. An imaging device has a sensitivity to a wavelength range ranging from a visible range to a range other than the visible range and converts the image formed by the image forming optical system to an electric signal. A wavelength range divides device dividing the wavelength range ranging from the visible range to the range other than the visible range into a plurality of wavelength ranges. A selects device selecting at least one wavelength range from among the wavelength ranges divided by the wavelength range dividing device. A signal processing device processes the output signals of the imaging device in response to the selected wavelength ranges so as to be video signals.

4 Claims, 49 Drawing Sheets

FIG.18(A) ROTARY FILTER

FILTERING PART: R | G | B | IR₁ | IR₂ | IR₃ | UV₁ UV₂ UV₃ | W
LIGHT INTERCEPTING PART

FIG.18(B) VISIBLE BAND

FIG.18(C) INFRARED BAND

FIG.18(D) ULTRAVIOLET BAND

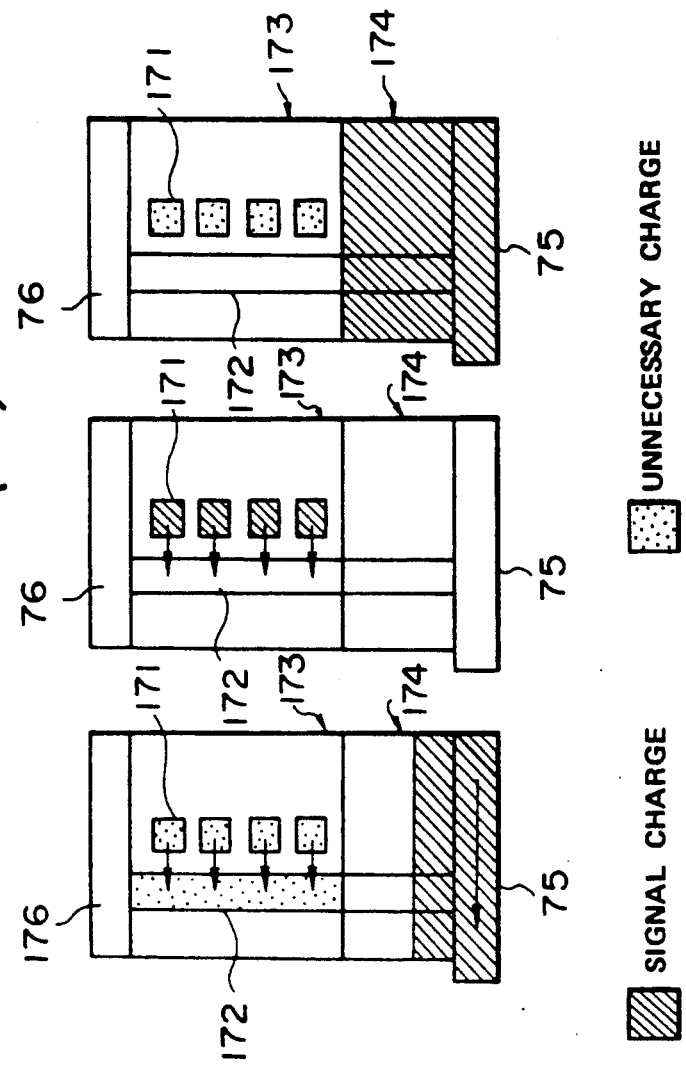

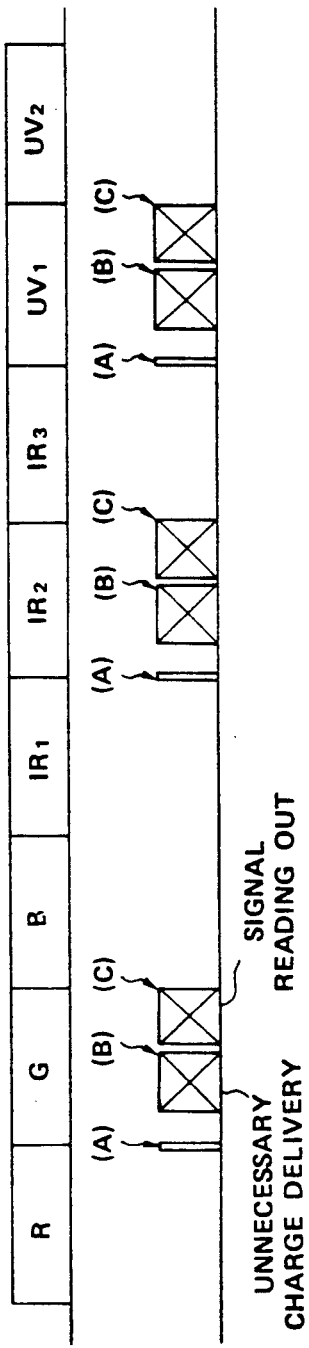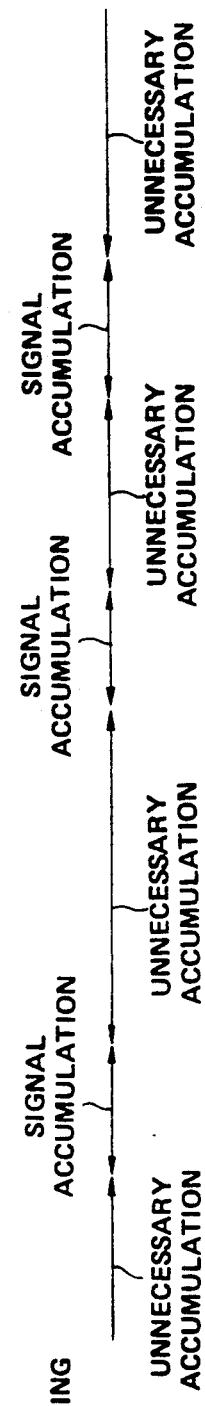

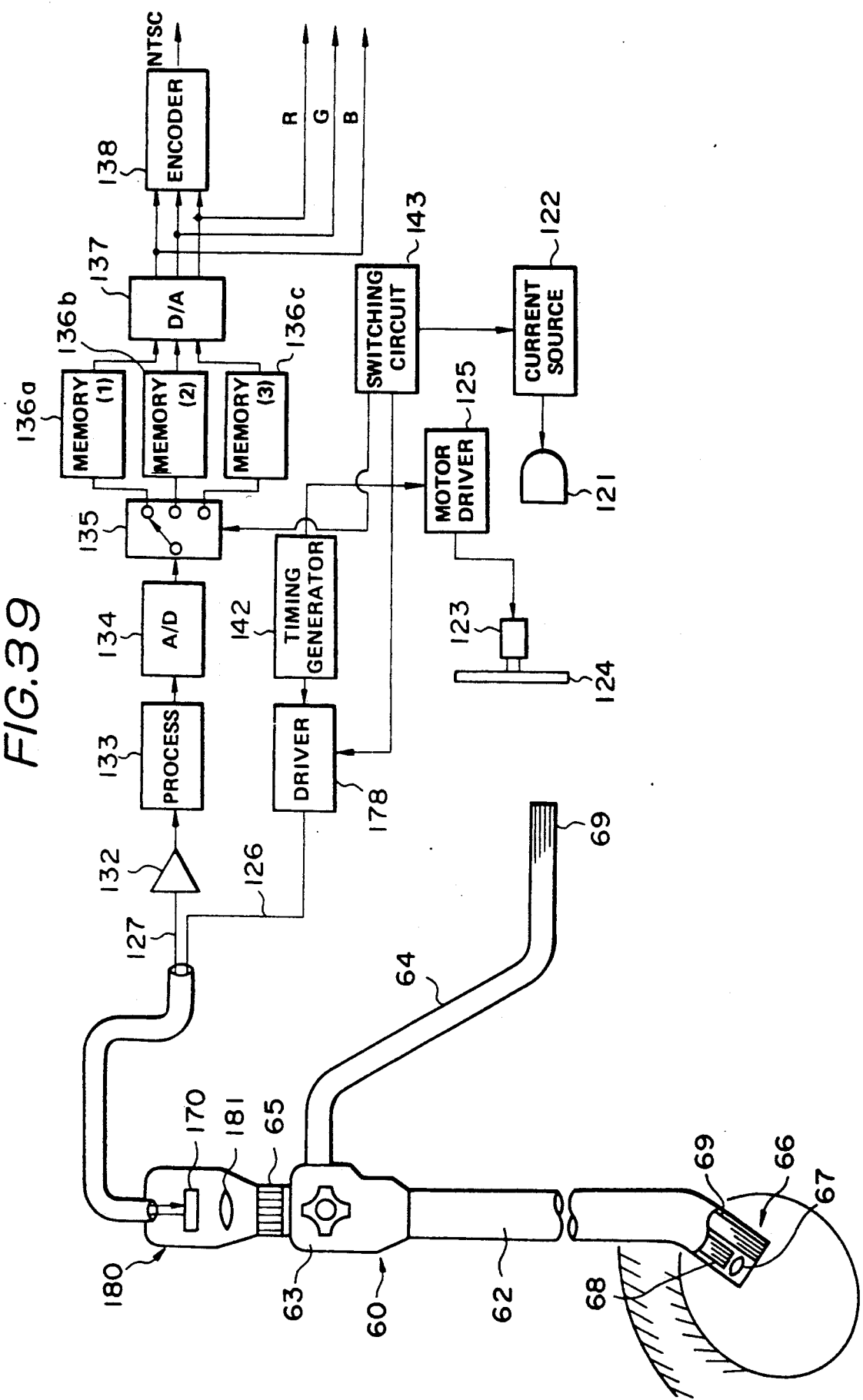

IMAGING APPARATUS AND ENDOSCOPE APPARATUS WITH SELECTABLE WAVELENGTH RANGES

This is a division, of application Ser. No. 128,118 filed on Nov. 30, 1987 and continued on Dec. 11, 1989 as Ser. No. 449,436 now U.S. Pat. No. 4,974,076.

BACKGROUND OF THE INVENTION

1. Field of the Invention

This invention relates to an imaging apparatus wherein the observing wavelength range can be selected in response to an observed object and an endoscope apparatus using the same.

2. Related Art Statement

Recently, there are suggested various electronic endoscopes wherein a solid state imaging device such as a charge coupled device (CCD) is used for an imaging means.

The electronic endoscope has advantages because the resolution is higher than in a fiberscope, it is easy to record and reproduce picture images and treatment of picture images such as enlargement and the comparison of two picture images are easy.

When observing an object by using an imaging device as of the above mentioned electronic endoscope and particularly when distinguishing an affected part and normal part from each other within a living body, it is necessary to sense (recognize) a delicate color tone difference. However, in case the difference of the color tone in the observed position is delicate, a high degree of knowledge and experience will be required to sense this delicate difference, a long time will be required until it is detected and it has been difficult to always properly judge the difference even if cautious forces are concentrated while sensing.

In order to cope with this situation, for example, in the gazette of Japanese Patent Laid Open No. 3033/1981, there is disclosed a technique wherein, by noting that the difference of the color tone may be large in a range other than the visible range as, for example, an infrared wavelength range, a spectral light having at least one infrared wavelength range is led in time series to illuminate an object to be observed. The reflected light from the object is imaged in a solid state imaging device and is converted to an electric signal. The electric signal is processed in response to the wavelength range and a picture image of the wavelength range is displayed by a specific color signal. According to this related art example, the invisible information obtained in the infrared wavelength range can be converted to visible information and, for example, the affected part and normal part can be quickly and easily discriminated from each other.

However, in the above mentioned related art example, since the observing wavelength range is fixed, for example, there are disadvantages that, when infrared light is utilized, no picture image of a general visible range will be obtained, it will be difficult to compare both picture images and there will be no effect on an observed object characteristic in another wavelength range.

Also, for example, in the gazette of Japanese Patent Laid Open No. 139237/1984, there is disclosed a technique that a plurality of picture images are taken by passing a fluorescence generated from a living body in response to an excited light radiation through a plurality of types of band pass filters and respectively different color tones are alloted to the density grade differences of the respective picture images to form respective quasi color picture images.

However, in this related art example, the density difference can be discriminated but the color tone difference can not be discriminated.

OBJECTS AND SUMMARY OF THE INVENTION

An object of the present invention is to provide an imaging apparatus and endoscope apparatus whereby visible information can be obtained by selecting a suitable wavelength range in response to an object to be observed.

Another object of the present invention is to provide an imaging apparatus and endoscope apparatus whereby the color tone differences, in the respective positions of an observed object which are difficult to discriminate in a picture image in a general visible range, can be easily detected.

A further object of the present invention is to provide an imaging apparatus and endoscope apparatus whereby the state of veins running below a mucous membrane and the penetrating range of a disease can be observed.

A further object of the present invention is to provide an imaging apparatus and endoscope apparatus whereby a color distribution in a living body tissue can be detected.

Each of the imaging apparatus and endoscope apparatus of the present invention comprises an image forming optical system forming an image of an object to be imaged, an imaging device having a sensitivity in a wavelength range ranging from a visible range to another range other than the visible range and converting the image formed by the above mentioned image forming optical system to an electric signal, a wavelength range dividing device dividing the wavelength range ranging from the visible range to the range other than the visible range into a plurality of wavelength ranges, a selecting device selecting at least one wavelength range from among the wavelength ranges divided by the above mentioned wavelength range dividing device and a signal processing device processing the output signal of the above mentioned imaging device to be a video signal in response to the above mentioned selected wavelength range.

The other features and advantages of the present invention will become apparent enough with the following explanation.

BRIEF DESCRIPTION OF THE DRAWINGS

FIG. 1 is a block diagram showing the formation of an imaging apparatus.

FIG. 2 is a side view showing an entire electronic endoscope apparatus.

FIG. 3 is an explanatory view showing a band switching filter.

FIG. 4 is an explanatory view showing a rotary filter.

FIG. 5 is an explanatory view showing the transmitted wavelength bands of the respective filters of the band switching filter.

FIG. 6 is an explanatory diagram showing the transmitting characteristics of the respective filters of the rotary filter.

FIG. 9 is a block diagram showing an imaging apparatus.

FIG. 10 is an explanatory view showing a rotary filter.

FIG. 11(A) is a timing chart showing a timing of an illuminating light.

FIG. 11(B) is a timing chart showing a timing of selecting a signal at the time of selecting a visible band.

FIG. 11(C) is a timing chart showing a timing of selecting a signal at the time of selecting an ultraviolet band.

FIG. 11(D) is a timing chart showing a timing of selecting a signal at the time of selecting an infrared band.

FIG. 11(E) is a timing chart showing a timing of selecting wavelength ranges of G, R and IR1.

FIG. 12 is a block diagram showing an imaging apparatus.

FIG. 15 is an explanatory diagram showing a spectral characteristic variation of blood by mixing in ICG.

FIGS. 16 to 18 relate to the fifth embodiment of the present invention.

FIG. 16 is an explanatory view showing the formation of an endoscope apparatus.

FIG. 17 is an explanatory view showing a rotary filter.

FIG. 18(A) is a timing chart showing a timing when respective filters of a rotary filter are interposed in an illuminating light path.

FIG. 18(B) is a timing chart showing a timing when a lamp emits a light at the time of selecting a visible band.

FIG. 18(C) is a timing chart showing a timing when a lamp emits a light at the time of selecting an infrared band.

FIG. 18(D) is a timing chart showing a timing when a lamp emits a light at the time of selecting an ultraviolet band.

FIG. 18(E) is a timing chart showing a timing when a lamp emits a light at the time of selecting wavelength ranges of G, IR2 and IR3.

FIG. 18(F) is a timing chart showing a timing when a lamp emits a light at the time of selecting a wavelength range of B.

FIG. 19 is an explanatory view showing the formation of an imaging apparatus.

FIG. 20 is an elevation of a band switching mirror.

FIG. 21 is an explanatory diagram showing reflection characteristics of respective mirrors of the band switching mirror.

FIG. 24 is an explanatory view showing a light source part.

FIG. 25 is an explanatory view showing a rotary filter.

FIG. 26 is a block diagram showing the formation of an imaging apparatus.

FIG. 27 is an explanatory view showing a rotary filter.

FIG. 28 is an explanatory diagram showing transmitting characteristics of respective filters of a rotary filter.

FIG. 29 is an explanatory diagram showing absorption spectra of respective colors of a living body.

FIGS. 33 and 34 relate to the ninth embodiment of the present invention.

FIG. 33 is an explanatory view showing the formation of a CCD (charge coupled device).

FIG. 34(A) is an explanatory view showing a shutter.

FIG. 34(B) is an explanatory view showing another state of the shutter.

FIGS. 35 to 38 relate to the tenth embodiment of the present invention.

FIG. 35 is a block diagram showing the formation of an imaging apparatus.

FIG. 36 is an explanatory view showing the formation of a CCD with an electronic shutter.

FIGS. 37(A), 37(B) and 37(C) are explanatory views showing respective operating modes of electronic shutters.

FIG. 38(A) is a timing chart showing timings when respective filters of a rotary filter are interposed in an illuminating light path.

FIG. 38(B) is a timing chart showing an operating mode of a CCD.

FIG. 38(C) is a timing chart showing an operation of a light receiving part of a CCD.

FIG. 39 is an explanatory view showing the formation of an endoscope apparatus relating to the eleventh embodiment of the present invention.

FIG. 40 is a block diagram showing an imaging apparatus.

FIG. 41 is an explanatory view showing a band limiting filter.

FIG. 42 is an explanatory diagram showing the transmitting characteristics of respective filters of a band limiting filter.

FIG. 43 is an explanatory view of a rotary filter.

FIG. 44 is an explanatory diagram showing the transmitting characteristics of respective filters of the rotary filter.

FIG. 48 is an explanatory diagram showing a light source part.

FIG. 49 is an explanatory diagram showing the transmitting characteristic of a band limiting filter of a narrow band.

FIG. 50 is an explanatory diagram showing the difference between the spectral characteristics of blood in which ICG is mixed and blood in which ICG is not mixed.

FIG. 53 is an explanatory view showing a rotary filter.

FIG. 54 is an explanatory diagram showing the transmitting characteristics of the respective filters of the rotary filter.

FIG. 55 is an explanatory view showing a band limiting filter.

FIG. 56 is an explanatory diagram showing the transmitting characteristics of the respective filters of the band limiting filter.

FIG. 57 is an explanatory view showing a rotary filter.

FIG. 58 is an explanatory diagram showing the transmitting characteristics of the respective filters of the rotary filter.

FIG. 60 is a block diagram showing the formation of an imaging apparatus.

FIG. 61 is an explanatory diagram showing the light emitting characteristic of a light source.

FIG. 62 is an explanatory diagram showing the transmitting characteristics of the respective filters of a band limiting filter.

FIG. 64 is an explanatory view showing a color filter.

FIG. 65 is an explanatory diagram showing the transmitting characteristics of the respective filters of the color filter.

FIG. 70 is an explanatory view showing a band limiting filter.

FIG. 71 is an explanatory diagram showing the transmitting characteristics of the respective filters of the band limiting filter.

FIG. 72 is an explanatory diagram showing the transmitting characteristics of the respective filters of a rotary filter.

FIG. 74 is a block diagram showing the formation of an imaging apparatus.

FIG. 75 is an explanatory diagram showing a color separating filter.

FIG. 76 is an explanatory diagram showing the transmitting characteristics of respective filters.

FIG. 77 is an explanatory diagram showing the transmitting characteristic of a filter interposed in an observing light path.

FIG. 78 is an explanatory diagram showing the transmitting characteristic of a visible light transmitting filter.

FIG. 79 is an explanatory diagram showing the transmitting characteristic of a near infrared band pass filter.

FIG. 80 is a block diagram showing the formation of an imaging apparatus.

FIG. 81 is an explanatory view showing a rotary filter.

FIG. 82 is an explanatory diagram showing the transmitting characteristics of respective filters of the rotary filter.

DETAILED DESCRIPTION OF THE PREFERRED EMBODIMENTS:

The first embodiment of the present invention is shown in FIGS. 1 to 6.

Figure 2:
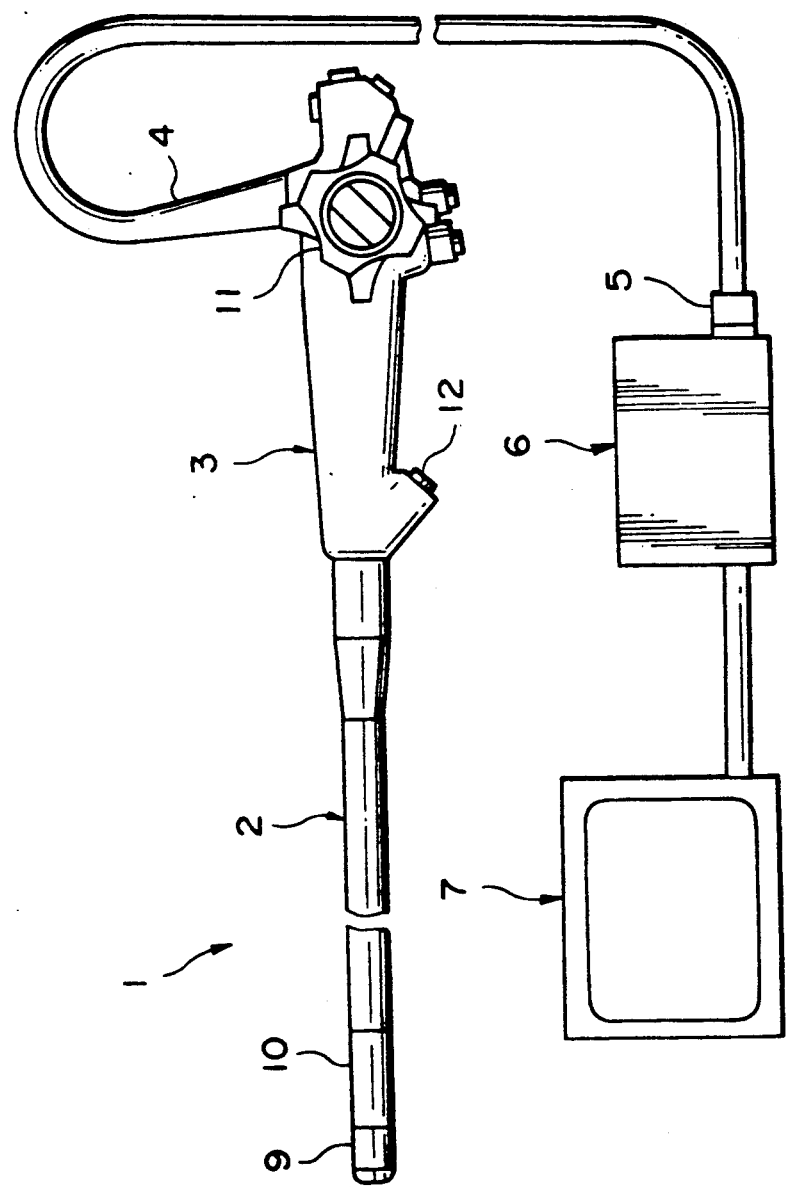

The imaging apparatus of this emobiment is applied to as electronic endoscope 1 as is shown, for example, in FIG. 2. In this electronic endoscope 1, a large diameter operating part 3 is connected to the rear end of an elongated, for example, flexible insertable part 2. A flexible cable 4 is extended sidewise from the rear end part of the above mentioned operating part 3 and is provided at the tip with a connector 5. The above mentioned electronic endoscope 1 is to be connected through the above mentioned connector 5 to a control apparatus in which light source part and video signal processing part are built. Further, a color CRT monitor as a displaying means is to be connected to the above mentioned control apparatus 6.

A rigid tip part 9 is provided on the tip side of the above mentioned insertable part 2 and a curvable curve part 10 is provided on the rear side adjacent to this tip part 9. The above mentioned curve part 10 can be curved in the horizontal and vertical directions by rotating a curving knob 11 provided on the above mentioned operating part 3. An inserting port communicating with a forceps channel provided within the above mentioned insertable part 2 is provided in the above mentioned operating part 3.

Figure 1:
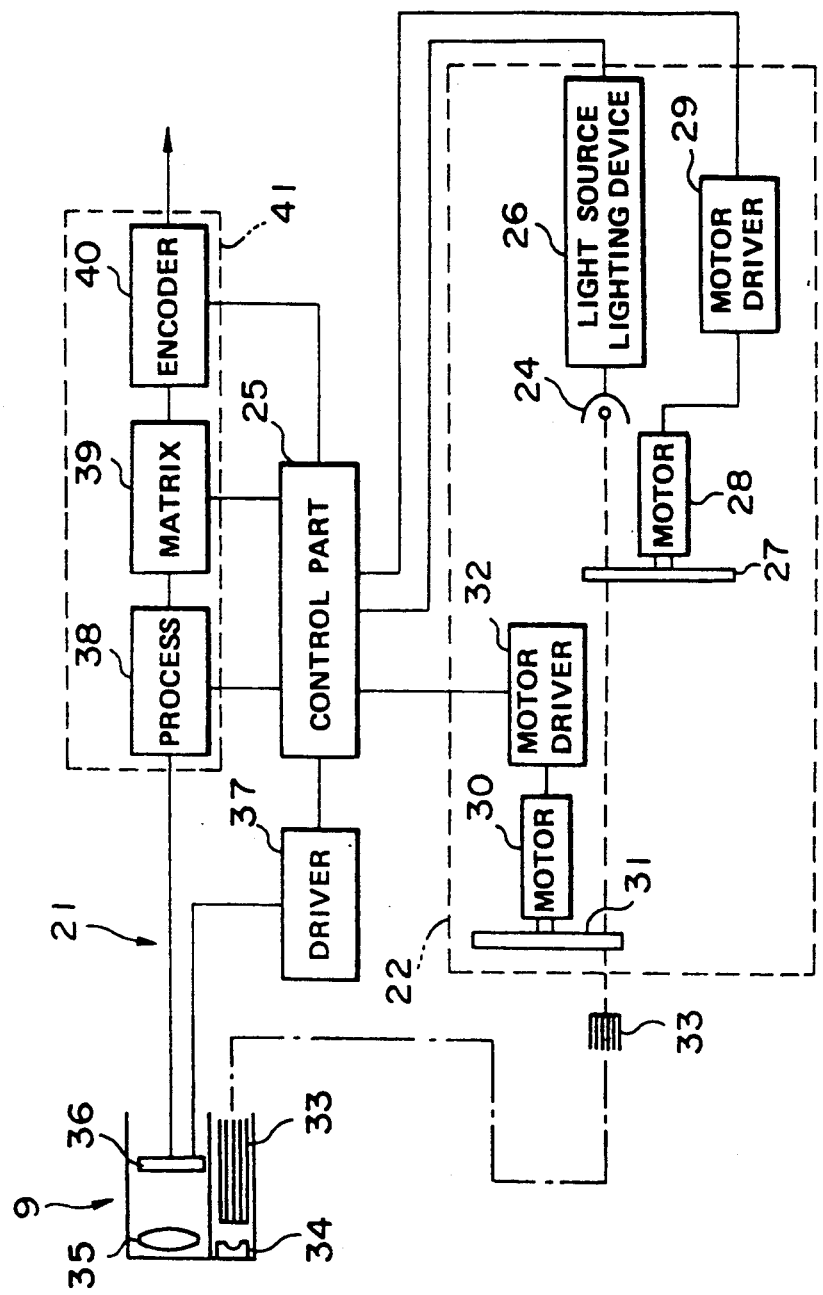
FIGS. 1 to 6 relate to the first embodiment of the present invention.
Figure 3:
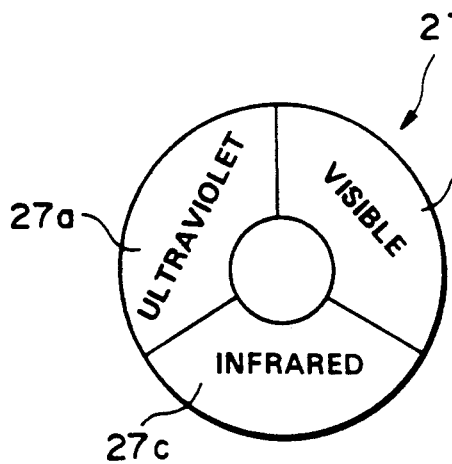
Figure 5:
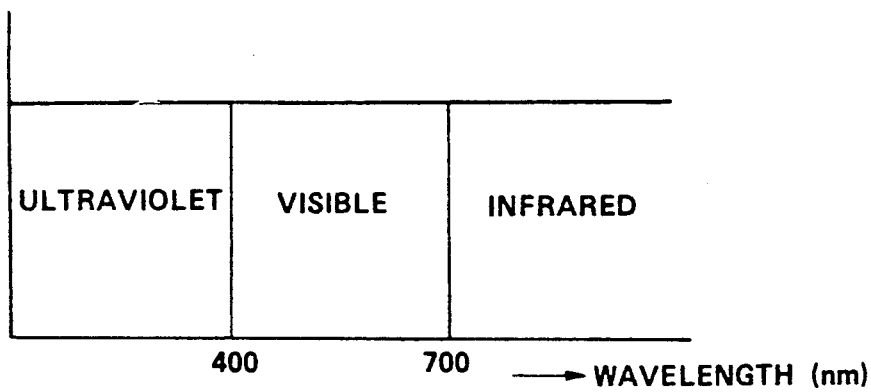

An imaging apparatus 21 of this embodiment is formed as shown in FIG. 1. A light source part 22 having a light source 24 is provided within the above mentioned control apparatus 6. The above mentioned light source 24 emits lights of wavelengths in a wide range from an ultraviolet range to an infrared range and including a visible range and can be a general halogen lamp, xenone lamp or strobo lamp. This light source 24 is controlled in lighting by a light source lighting apparatus 26 controlled by a control part 25. A band switching filter 27 as a selecting means rotated and driven by a driving motor 28 is arranged in front of the above mentioned light source 24. This band switching filter 27 is peripherally divided into three parts as shown in FIG. 3 and filters 27a, 27b and 27c, transmitting respectively an ultraviolet band, visible band and infrared band, as shown in FIG. 5, are arranged respectively in the divided parts so that any of the ultraviolet band, visible band and infrared band may be selectively transmitted by this band switching filter 27. The, above mentioned driving motor 28 is controlled in the rotation by a motor driver 29 controlled by the control part 25.

Figure 4:
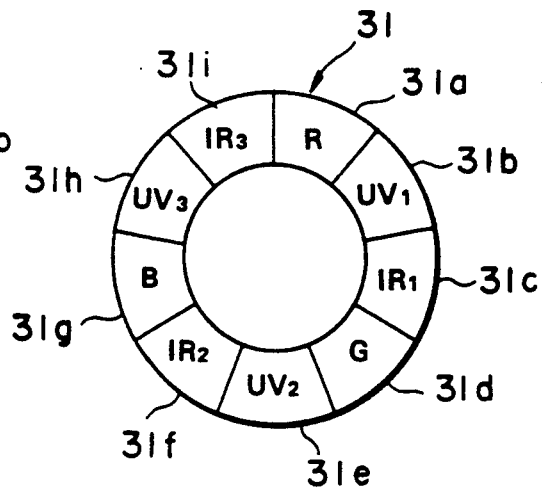
Figure 6:
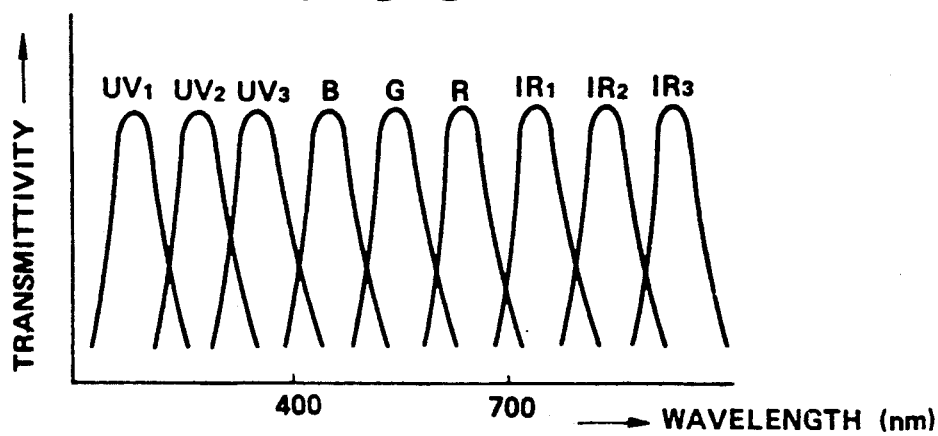

A rotary filter 31 as a dividing means, rotated and driven by a driving motor 30, is arranged forward in the advancing direction of the light having passed through the above mentioned band switching filter 27. This rotary filter 31 is peripherally divided into nine parts as shown in FIG. 4 and filters 31a to 31i transmitting respectively a red light (R), first ultraviolet light (UV1), first infrared light (IR1), green light (G), second ultraviolet light (UV2), second infrared light (IR2), blue light (B), third ultraviolet light (UV3) and third infrared light (IR3) having respectively transmitting characteristics as are shown in FIG. 6 are arranged in this order in the respective divided parts. The above mentioned first to third infrared lights are different from each other in wavelength range and the central wavelength is longer in the order of R1, IR2, and IR3. In the same manner, the above mentioned first to third ultraviolet lights are different from each other in wavelength range and the central wavelength is longer in the order of UV1, UV2 and UV3. The above mentioned driving motor 30 is controlled in the rotation by a motor driver 32 controlled by the control part 25.

The light emitted from the light source part 22 through the above mentioned rotary filter 31 enters the light guide 33 inserted through the above mentioned cable 4 and insertable part 2, is led to the tip part 9 through this light guide 33 and is emitted from a light distributing lens system 34 provided in this tip part 9 to illuminate an object to be observed.

In this embodiment, the combination of the wavelength ranges of the light emitted from the above mentioned rotary filter 31 is switched by the band selected by the above mentioned band switching filter 27. That is to say, in case the infrared band is selected by the above mentioned band switching filter 27, the first to third infrared light IR1, IR2 and IR3 will be emitted in time series. In case the visible band is selected, the respective color light of red (R), green (G) and blue (B) will be emitted in time series. In case the ultraviolet band is selected, the first to third ultraviolet light UV1, UV2 and UV3 will be emitted in time series.

On the other hand, a solid state imaging device 36 as an imaging means is arranged in the image forming position of an objective lens system provided in the above mentioned tip part 9. This solid state imaging device 36 has a sensitivity to a wide wavelength range from the ultraviolet range to the infrared range and including the visible range. Also, the respective filters 31a to 31i of the above mentioned rotary filter 31 have transmitting characteristics within the range to which the above mentioned solid state imaging device 36 has a sensitivity.

The image of the observed object formed by the above mentioned solid state imaging device 36 is photo-electrically converted and the signals corresponding to the respective picture elements of this solid state imaging device 36 are read out in time series as synchronized with the switching of the illuminating light by a driver 37 controlled by the control part 25. The output signal of this solid state imaging device 36 is input into a video signal processing part consisting of a process circuit 38, matrix circuit 39 and encoder 40 respectively controlled by the control part 25. The output signals of the above mentioned solid state imaging device 36 are first input into the process circuit 38 wherein the output signals corresponding to the illuminating lights in the respective wavelength ranges are alloted to the respective colors of red (R), green (G) and blue (B) to produce R, G and B color signals.

The R, G and B color signals from the above mentioned process circuit 38 are input into the matrix circuit 39 wherein, for example, an NTSC system luminance signal Y and color difference signals R-Y and B-Y are produced by the above mentioned R, G and B signals. Further, the output of this matrix circuit 39 is input into the encoder 40 by which an NTSC system video signal is produced. This video signal is input into the above mentioned color CRT monitor and the observed object is color-displayed.

In this embodiment formed as in the above, the wavelength range in which the solid state imaging device 36 has a sensitivity is divided into nine wave-length ranges UV1 to IR3 by the rotary filter 31. Three wavelength ranges are selected from among the above mentioned nine wavelength ranges UV1 to IR3 by selecting any of the ultraviolet, visible and infrared bands by the band switching filter 27. The combination of these three wavelength ranges is of the first to third ultraviolet light UV1 to UV3, the respective color light of red (R), green (G) and blue (B) or the first to third infrared light IR1 to IR3. The light of these selected three wavelength ranges are radiated in time series onto the observed object.

The reflected light of the observed object corresponding to the respective illuminating light of the selected three wavelength ranges are photo-electrically converted by the solid state imaging device 36, are synchronized with the switching of the illuminating light and read out in time series.

The output signals corresponding to the respective illuminating light of the above mentioned solid state imaging device 36 are alloted to any of the respective colors of red (R), green (G) and blue (B) and are processed to be video signals in the video signal processing part 41.

The observed object is color-displayed by the respective alloted colors. That is to say, in case the ultraviolet band or infrared band is selected by the band switching filter 27, the observed object will be displayed in quasi colors.

Thus, according to this embodiment, the observed object can be color-displayed by selecting any of the ultraviolet, visible and infrared bands and alloting them to any colors. Therefore, the color tone differences in the respective positions of the observed object difficult to discriminate in a picture image in a general visible range can be easily detected.

The band switching filter 27 is not limited to be divided into the ultraviolet range, visible range and infrared range but, for example, a filter in which the long wavelength side of the visible range and a part of the short wavelength side of the infrared range are made transmitting bands may be provided so that the light having passed through this filter may be transmitted through the rotary filter 31, the respective color light of green (G) and red (R) and the first infrared light (IR1) may be radiated in time series onto the observed object and the respective colors of blue (B), green (G) and red (R) may be alloted to the above mentioned respective color light of green(G) and red(R) and the first infrared light(IR1) so as to be color-displayed. These color picture image may be compared with a color picture image in a general visible range. Thus, various color picture images can be obtained by the combination of the band switching filters 27 and rotary filter 31.

The above mentioned band switching filter 27 and rotary filter 31 may be arranged between the light source 24 and solid state imaging device 36 and the arranging order can be freely determined.

The arrangement in time series of the respective filters 31a to 31i of the rotary filter 31 can be properly set in relation to the timing of reading out of the solid state imaging device 36.

The light source 24 is not limited to emit the light of all the ultraviolet, visible and infrared ranges but, for example, a plurality of light sources each emitting the light of at least one band may be provided to be used as switched.

For example, in case a line transfer type CCD is used for the solid state imaging device 36, for example, in case the respective color light of red(R), green(G) and blue(B) are used for the illuminating light, UV1+IR1, UV2+IR2 and UV3+IR3 may be used for the light intercepting parts and, in case IR1 to IR3 are used for the illuminating light, G+UV2, B+UV3 and R+UV1 may be used for the light intercepting parts.

A strobo lamp which can be switched on and off at a high speed may be used instead of using a wavelength band limiting filter as the band switching filter 27 so that light may be emitted when the filters of the wavelength bands UV1 to UV3, B, G and R and IR1 to IR3 which are required among the respective filters 31 are in the light path and the other filter parts may be used for the read out periods.

Figure 7:
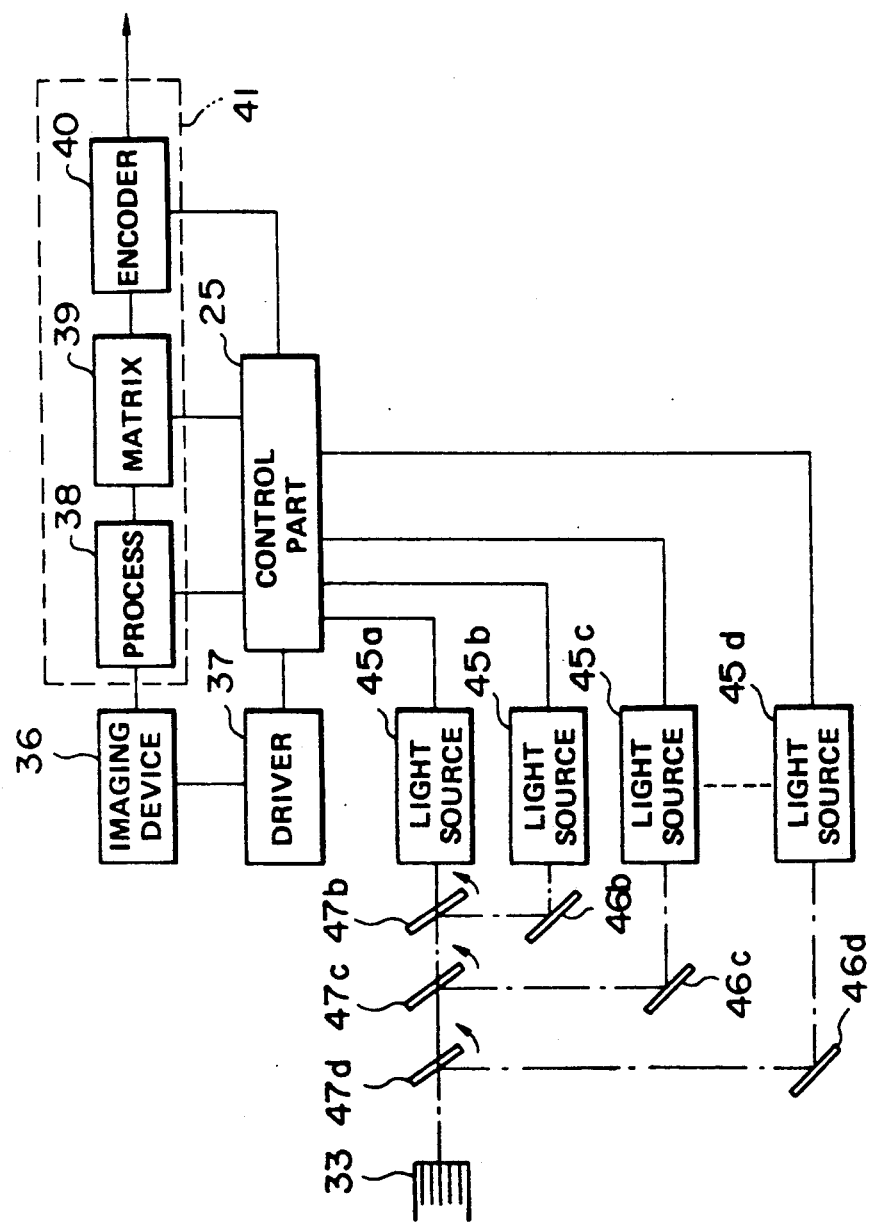
FIGS. 7 and 8 are block diagrams showing imaging apparatus relating to the second embodiment of the present invention.
Figure 8:
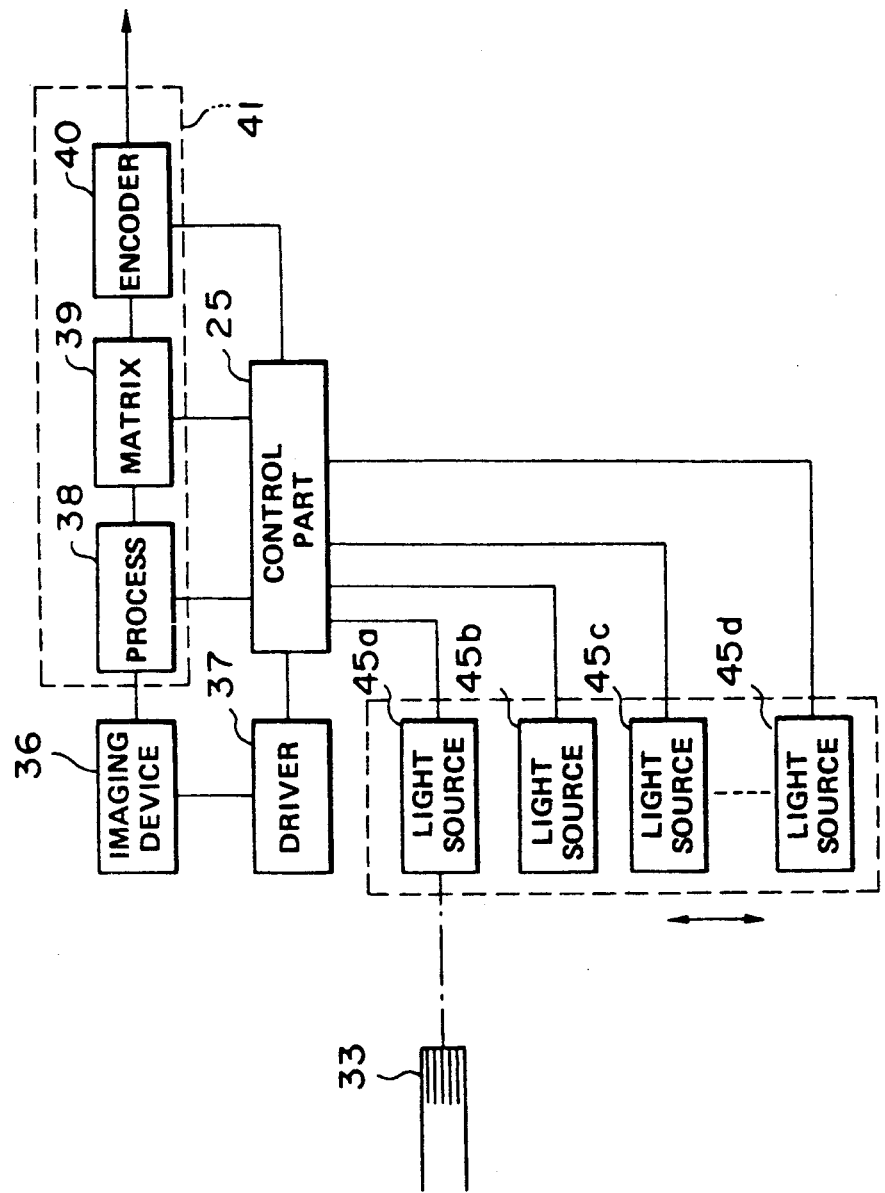

The second embodiment of the present invention is shown in FIGS. 7 and 8.

In this embodiment, a plurality of light sources respectively emitting light of different specific wavelength ranges are provided. Such narrow band light sources as lasers are used for this plurality of light sources 45a to 45d. One to three light sources are selected by the control part 25 from among the above mentioned plurality of light sources 45a to 45d and are made to emit lights in time series as synchronized with the timing of reading out of the solid state imaging device 36. The light of the selected three wavelength ranges are radiated in time series onto the observed object. The other formations are the same as in the first embodiment.

There is a means by which the light emitted selectively from the above mentioned plurality of light sources 45a to 45d are made to enter one light guide 33 as is shown, for example, in FIG. 7. That is to say, one light source 45a is arranged in the position in which the light emitted from this light source 45a directly enters the light guide 33 and the light emitted from the other light sources 45b to 45d are made to enter the above mentioned light guide 33 respectively through mirrors 46b to 46d and through rotatable mirrors 47b to 47d arranged between the above mentioned light source 45a and light guide 33. In case the light emitted from the light source 45a is to be made to enter the light guide 33, all the above mentioned mirrors 47b to 47d are retreated from the illuminating light path of the light source 45a. In case the light emitted from the other light sources 45b to 45d are to be made to enter the light guide 33, only the mirror corresponding to the light source made to emit the light among the above mentioned mirrors 47b to 47d is interposed in the illuminating light path of the light source 45a.

As another means by which the lights emitted selectively from the above mentioned plurality of light sources 45a to 45b are made to enter one light guide 33, for example, as shown in FIG. 8, the plurality of light sources 45a to 45d may be made integrally movable and the light source to emit the light may be selectively opposed to the entrance end of the light guide 33.

For the lamps to be used for the light sources 45a to 45d shown in FIGS. 7 or 8, there are enumerated a laser and LED each emitting a light by limiting the wavelength. A xenone lamp, halogen lamp and strobo lamp in each of which an absorption type filter or evaporative deposition type filter in which a color is mixed may be provided in the emitting port emitting a light in a wide band may be provided to limit the output wavelength.

According to this embodiment, the wavelength range can be selected more freely.

Figure 9:
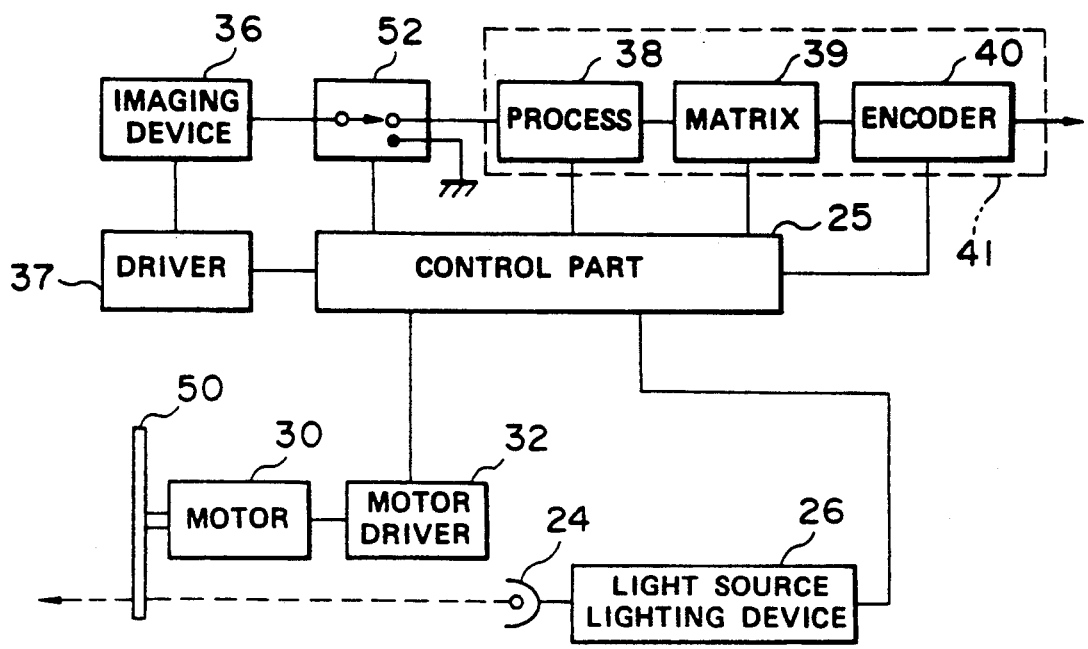
FIGS. 9 to 11 relate to the third embodiment of the present invention.
Figure 10:
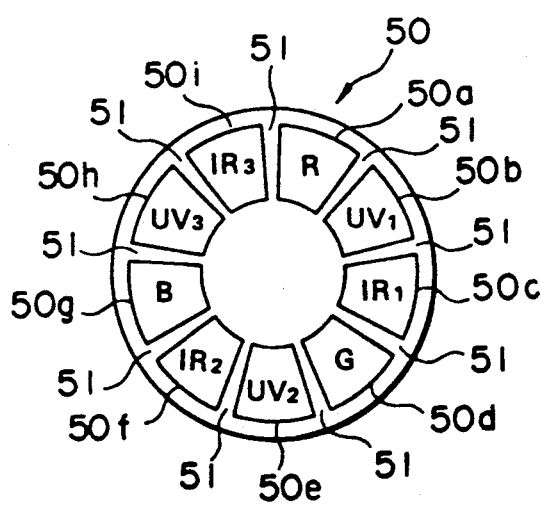
Figure 11:
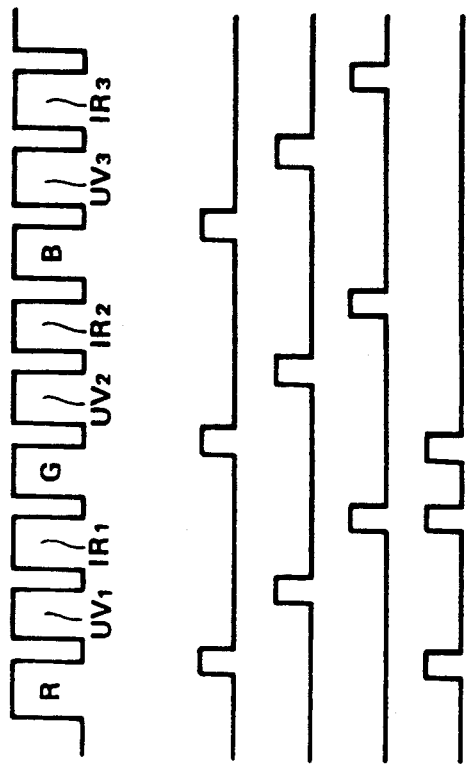
Figure 12:
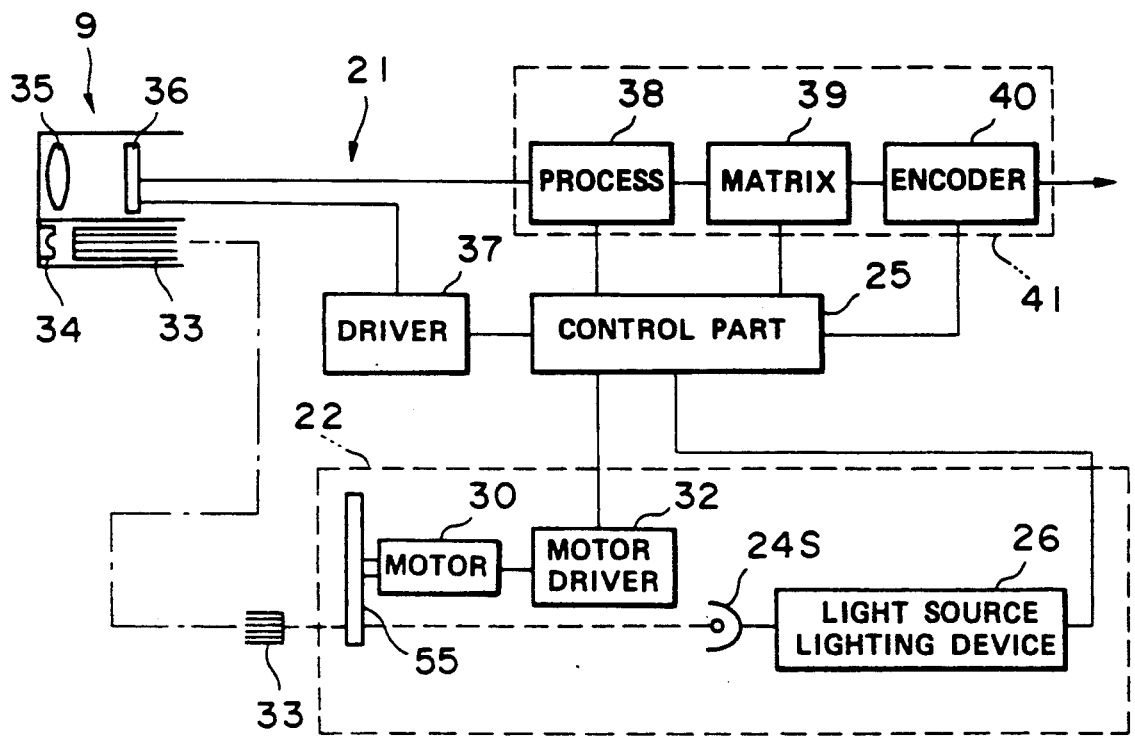
FIGS. 12 and 15 relate to the fourth embodiment of the present invention.

The third embodiment of the present invention is shown in FIGS. 9 to 11.

In this embodiment, a color filter 50 as is shown in FIG. 10 is arranged in front of the light source 24. This color filter 50 is divided into nine parts in the peripheral direction the same as in the rotary filter 31 in the first embodiment. Filters 50a to 50i transmitting a red light(R), first ultraviolet light(UV1), first infrared light(IR1), green light(G), second ultraviolet light(UV2), second infrared light(IR2), blue light(B), third ultraviolet light(UV3) and third infrared light(IR3) respectively having transmitting characteristics as are shown in FIG. 6 are arranged in this order in the divided respective parts. Light intercepting parts 51 are provided respectively between the above mentioned filters 50a to 50i.

The light of the respective wavelength ranges having passed through the above mentioned respective filters 50a to 50i are radiated in time series onto an object to be observed.

In case the wavelength range of this illuminating light is switched, a light intercepting period corresponding to the above mentioned light intercepting part 51 will be provided. In this embodiment, the signal of the solid state imaging device 36 is read out in this light intercepting period.

Also, in this embodiment, a selecting circuit 52 is provided between the above mentioned solid state imaging device 36 and video signal processing part 41 and is controlled by the control part 25 so that the output signal of the above mentioned solid state imaging device 36 may be selected and delivered to the video signal processing part 41.

The timing of the selection of this selecting circuit 52 is shown in FIGS. 11(A) to 11(E). That is to say, when the observation is in the visible band, the signal will be selected at the time of reading out corresponding to the illuminating light of R, G and B as shown in FIG. 11(B) for the timing of the illuminating light shown in FIG. 11(A). In the case when the observation is in the ultraviolet band, the signal will be selected at the time of reading out corresponding to the illuminating light of UV1, UV2 and UV3 as shown in FIG. 11(C). When the observation is in the infrared band, the signal will be selected at the time of reading out corresponding to the illuminating light of IR1, IR2 and IR3 as shown in FIG. 11(D). When the observation is in the band of a part of the long wavelength side of the visible range and the short wavelength side of the infrared range, the signal will be selected at the time of reading out corresponding to the illuminating light of R, IR1 and G.

According to this embodiment, the wavelength range can be selected more freely the same as in the second embodiment.

In the above mentioned first to third embodiments, the illuminating light may be radiated onto the observed object and the light having passed through this observed object may be received. The imaging means is not limited to the solid state imaging device provided in the tip part of the endoscope but may be a television camera externally fitted to the eyepiece part of the endoscope transmitting the observed image through the image guide.

The fourth embodiment of the present invention is shown in FIGS. 12 to 15.

Figure 13:
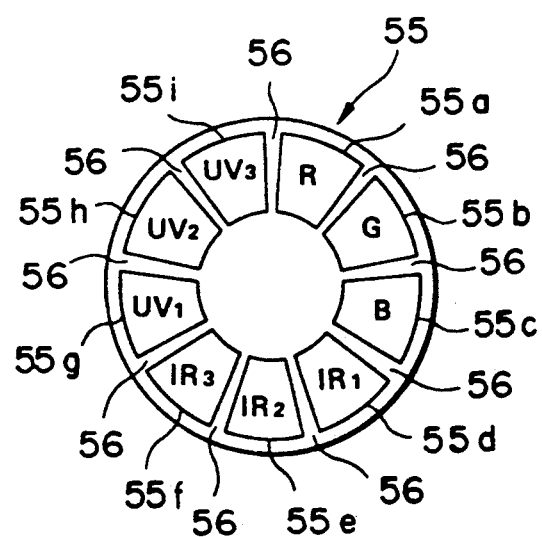
FIG. 13 is an explanatory view showing a rotary filter.
Figure 14:
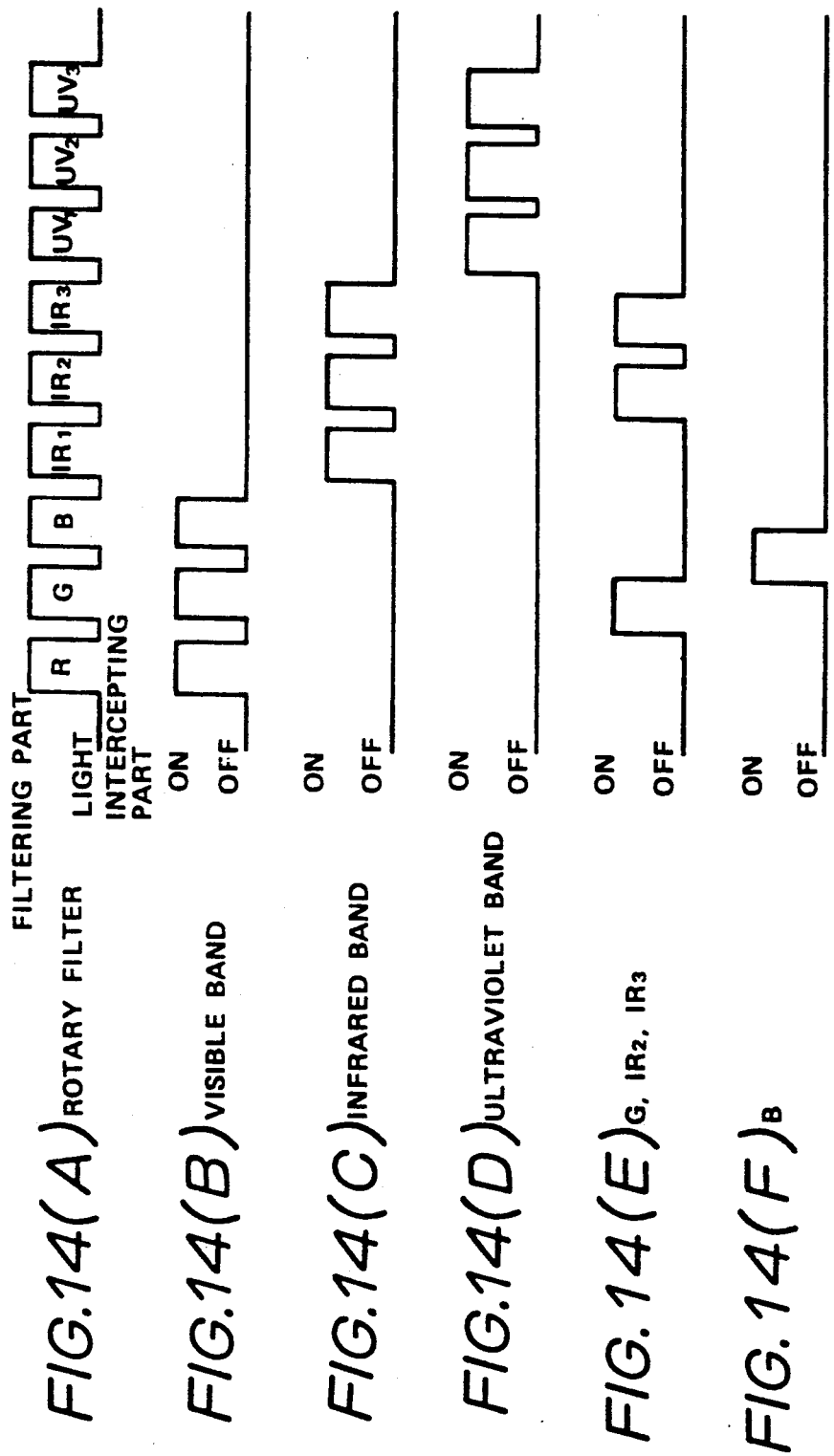
FIG. 14(A) is a timing chart showing a timing when respective filters of a rotary filter are interposed in an illuminating light path.
FIG. 14(B) is a timing chart showing a timing when a lamp emits a light at the time of selecting a visible band.
FIG. 14(C) is a timing chart showing a timing when a lamp emits a light at the time of selecting an infrared band.
FIG. 14(D) is a timing chart showing a timing when a lamp emits a light at the time of selecting an ultraviolet band.
FIG. 14(E) is a timing chart showing a timing when a lamp emits a light at the time of selecting wavelength ranges of G, IR2 and IR3.
FIG. 14(F) is a timing chart showing a timing when a lamp emits a light at the time of selecting a wavelength range of B.

In this embodiment, the observing wavelength band can be switched by using a strobo lamp 24S for the light source 24 instead of the band switching filter 27, motor 28 and motor driver 29 in the first embodiment. Also, in this embodiment, a rotary filter 55 different in the arrangement from the rotary filter 31 in the first embodiment is provided instead of the rotary filter 31 and is divided into nine parts in the peripheral direction as shown in FIG. 13. Filters 55a to 55i transmitting respectively R, G, B, IR1, IR2, IR3, UV1, UV2 and UV3 are arranged in this order in the divided respective parts. Light intercepting parts 56 are provided respectively between the filters 55a to 55i.

When the above mentioned rotary filter 55 is rotated, as shown in FIG. 14(A), the respective filters 55a to 55i of the above mentioned rotary filter 55 will be interposed in time series in the illuminating light path of the above mentioned strobe lamp 24S. The above mentioned strobo lamp 24S which can emit a light within a short time will emit a light when the filter corresponding to the wavelength range selected by the control part 25 comes into the light path. The object image corresponding to the light emitted from this strobo lamp 24S and having passed through the selected filter will be imaged by the solid state imaging device 36.

The other formations are the same as in the first embodiment.

In this embodiment, as shown, for example, in FIG. 14(B), the strobo lamp 24S will emit the light when the filters 55a, 55b and 55c corresponding respectively to the wavelength ranges of R, G and B come into the light path. A color picture image in the ordinary visible range will be obtained when the respective colors of R, G and B are alloted to the above mentioned wavelength ranges of R, G and B.

Also, as shown in FIG. 14(C), when the filters 55d, 55e and 55f corresponding respectively to the wavelength ranges of IR1, IR2 and IR3 come into the light path, the strobo lamp 24S will emit a light and the object image in the infrared range will be displayed in quasi colors. In the same manner, as shown in FIG. 14(D), when the filters 55g, 55h and 55i corresponding respectively to the wavelength ranges of UV1, UV2 and UV3 come into the light path, the strobo lamp 24S will emit a light and the object image in the ultraviolet range will be displayed in quasi colors.

Figure 15:
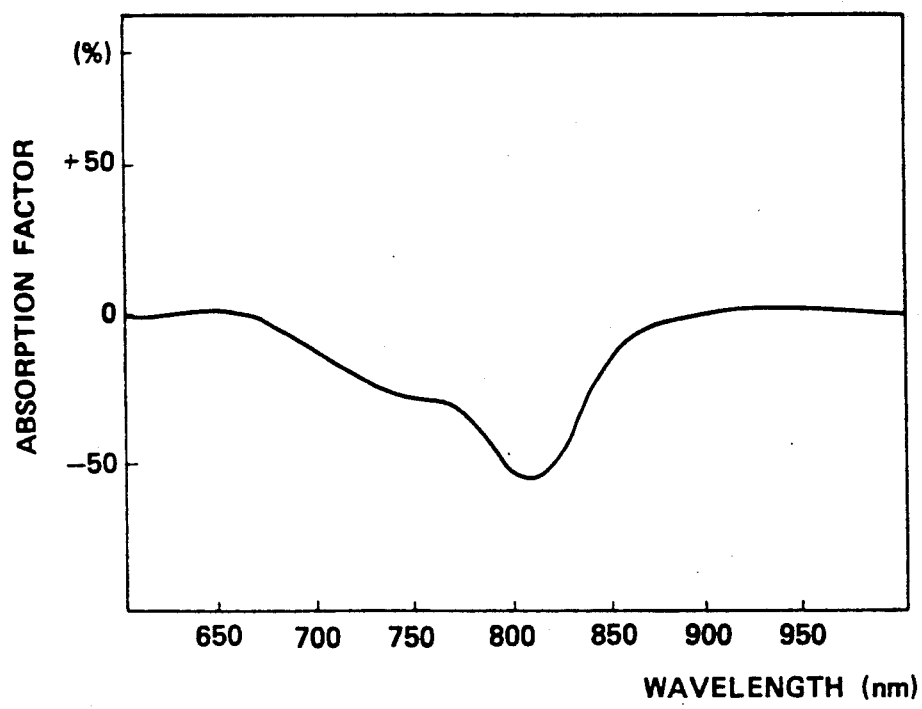

Now, the spectral characteristic variation of blood in which Indocyanine green(ICG) which is an infrared ray absorbing color is mixed is shown in FIG. 15. As shown in this diagram, the blood in which ICG is mixed has a maximum absorption of 805 nm. Therefore, the filter 55e corresponding to IR2 is made to have a band pass characteristic of an absorption factor having a maximum of 805 nm./in the center and the filter 55f corresponding to IR3 is made to be of a characteristic of transmitting a wavelength range of more than 850 nm. wherein the variation of the absorption factor is little recognized. The above mentioned ICD is mixed in blood, for example, by a venous injection. The strobo lamp 24S will emit a light when the filter 55e, 55f and 55b corresponding respectively to the wavelength ranges of IR2, IR3 and G as shown in FIG. 14(e) come into the light path. When the imaged object is displayed in quasi colors by the combination of the wavelength ranges of the above mentioned IR2, IR3 and G, the running state of the veins below the mucous membrane will be able to be confirmed by the difference between the outputs of IR2 and IR3. That is to say, when the infrared light high in the transmittivity through the tissue is used, the light will be able to reach the deep part of the tissue. On the other hand, as the blood has a maximum absorption at 805 nm. by the action of the above mentioned ICG, IR2 of IR2 and IR3 of the same reaching degree in the tissue will be more absorbed and will become a shadow in the vein part in the picture image by IR2. Therefore, by taking the difference from the picture image by IR3, the running state of the blood can be video-imaged at a high contrast. Also, by the picture image by G, the concavo-convexes and congested state on the surface of the mucous membrane can be definitely confirmed and the diagnosing activity can be improved.

Also, as shown in FIG. 14(F), when the filter corresponding to the specific single wavelength range comes into the filter light path, the strobo lamp 24S will emit a light and the object image in this wavelength range may be monocolor-displayed. In FIG. 14(F), only the picture image by B is obtained. However, the absorption in the short wavelength of B of the short wavelength is higher than the absorption characteristic of hemoglobin by R, IR1, IR2 and IR3 on the long wavelength side and therefore the distribution of the hemoglobin on the surface of the mucous membrane can be definitely observed. Also, by using another single wavelength range, a disease or the like can be diagnosed from the difference in picturing between the wavelength ranges.

Further, by forming the rotary filter 55 in a filter arrangement as is shown in FIG. 13, when the ordinary color displaying by R, G and B, as the filters 55a, 55b and 55c corresponding to the wavelength ranges of R, G and B are adjacent, there is an effect that the color displacement can be reduced.

Figure 17:
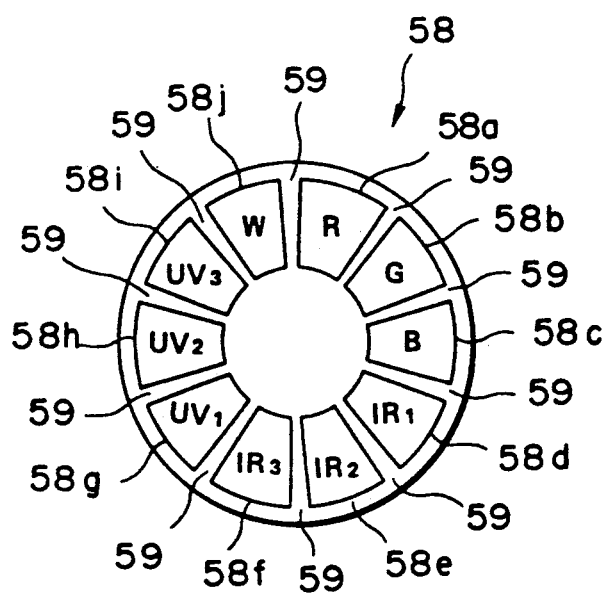
Figure 16:
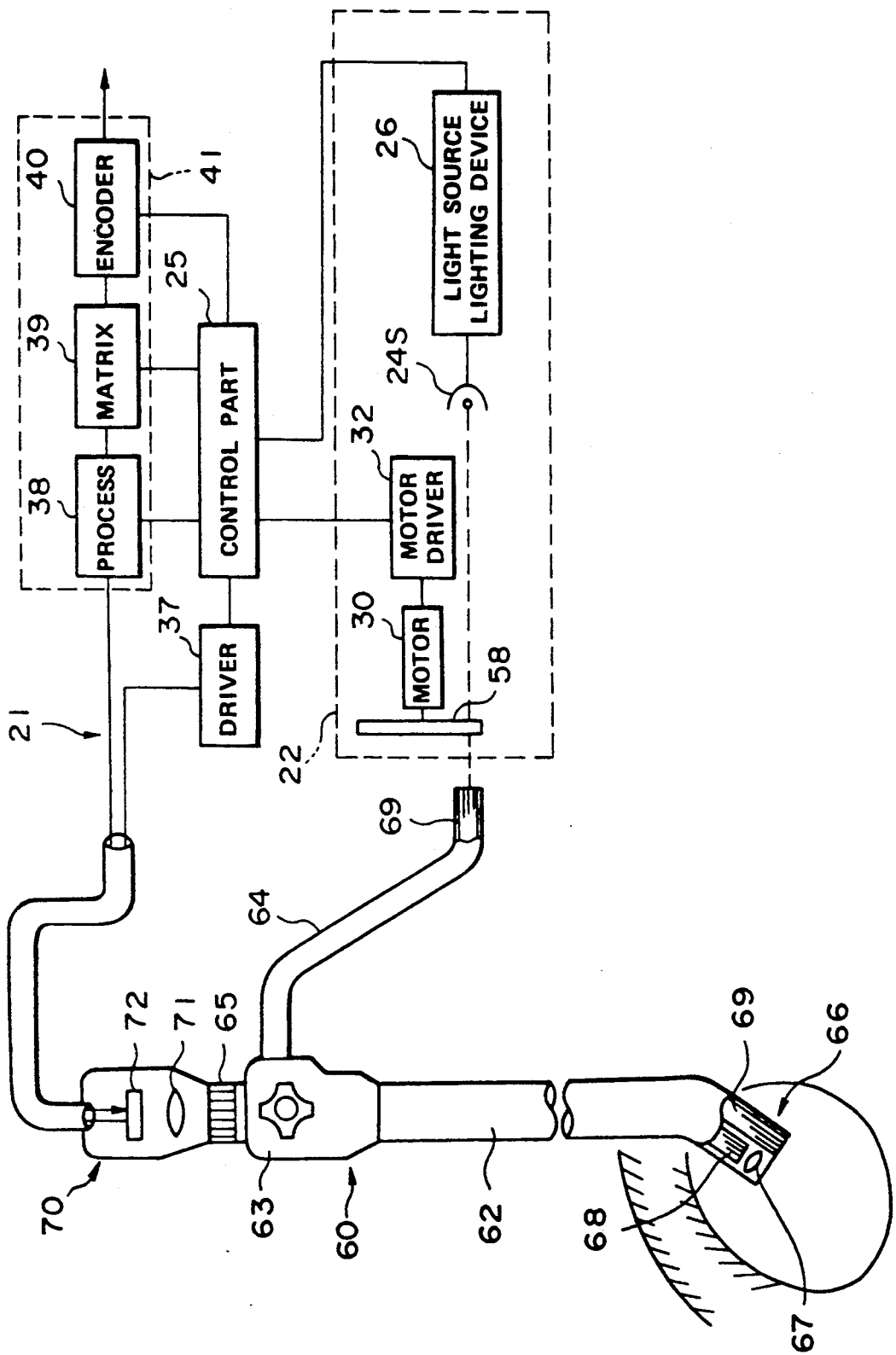

The fifth embodiment of the present invention is shown in FIGS. 16 to 18.

This embodiment is an endoscope apparatus in which a television camera is externally fitted to the eyepiece part of a fiberscope.

As shown in FIG. 16, a fiberscope 60 is provided with an elongated, for example, flexible insertable part 62 and a large diameter operating part 63 is connected to the rear end of this insertable part 62. A flexible light guide cable 64 is extended sidewise from the rear end part of the above mentioned operating part 63. An eyepiece part 65 is provided at the rear end of the above mentioned operating part 63.

A light guide 69 is inserted through the above mentioned insertable part 62 and is arranged on tip surface in the tip part 66 of the insertable part 62 so that an illuminating light may be emitted from this tip part 66. The above mentioned light guide 69 is inserted on the entrance end side through the above mentioned light guide cable 64, is connected to a connector not illustrated provided in the tip part of this light guide cable 64 and is connected to the control apparatus 6 through this connector so that the light emitted from the strobo lamp 24S within the control apparatus 6 may be incident.

The above mentioned tip part 66 is provided with an objective lens system 67. The tip surface of the image guide 68 is arranged in the image forming position of this objective lens system 67. This image guide 68 is inserted through the above mentioned insertable part 62 and is extended to the above mentioned eyepiece part 65. An object image formed by the above mentioned objective lens system is led to the eyepiece part 65 by the above mentioned image guide 68 so as to be observed from this eyepiece part 65.

An externally fitted television camera 70 is removably fitted to the above mentioned eyepiece part 65. This externally fitted television camera 70 is provided with an image forming lens 71 forming an image of the light from the above mentioned eyepiece part 65 and a solid state imaging device 72 arranged in the image forming position of this image forming lens 71. This solid state imaging device 72 is driven by the driver 37 within the control apparatus 6 the same as in the fourth embodiment and the signal read out is processed by the signal processing part 41.

The other formations are substantially the same as in the fourth embodiment but a rotary filter 58 is provided instead of the rotary filter 55 in the fourth embodiment. As shown in FIG. 17, this rotary filter 58 is divided into ten parts in the peripheral direction. Filters 58a to 58j respectively transmitting R, G, B, IR1, IR2, IR3, UV1, UV2, UV3 and W (white light) are arranged in this order in the divided respective parts. The filter 58j transmitting W is provided to enable the observation by a general visible light from the eyepiece part 65 of the fiberscope 60 and may be a filter transmitting substantially all the light emitted from the above mentioned strobo lamp 24 or may be a filter transmitting only a visible light range. Light intercepting parts 59 are provided respectively between the filters 58a to 58j.

When the above mentioned rotary filter 58 is rotated, as shown in FIG. 18(A), the respective filters 58a to 58j of the above mentioned rotary filter 58 will be interposed in time series in the illuminating light path of the above mentioned strobo lamp 24S. The above mentioned strobo lamp 24S will emit a light when the filter corresponding to the wavelength range selected by the control part 25 comes into the light path. The light emitted from this strobo lamp 24S and transmitted through the selected filter enters the entrance end of the light guide 69 and is emitted from the tip part 66. The returning light from the object by this illuminating light is formed to be an image on the tip surface of the image guide 68 by the objective lens system 67. This objective image is led to the eyepiece part 65 by the image guide 68 and is further imaged by the solid state imaging device 72 within the externally fitted television camera 70 connected to this eyepiece part 65.

In this embodiment, the same as in the fourth embodiment, as shown in FIG. 18(B), when the filters 58a, 58b and 58c corresponding respectively to the wave-length ranges of R, G and B come into the light path, the strobo lamp 24S will emit a light and, by alloting the respective colors of R, G and B to the wavelength ranges of the above mentioned R, G and B, a color image in the ordinary visible range will be obtained.

Also, as shown in FIG. 18(C), when the filters 58d, 58e and 58f corresponding respectively to the wavelength ranges of IR1, IR2 and IR3 come into the light path, the strobo lamp 24S will emit a light and the object image in the infrared range will be displayed in quasi colors. In the same manner, as shown in FIG. 18(D), when the filters 58g, 58h and 58j corresponding respectively to the wavelength ranges of UV1, UV2 and UV3 come into the light path, the strobo lamp 24S will emit a light and the object image will be displayed in quasi colors.

The same as in the fourth embodiment, the filter 58e corresponding to IR2 is made to be of a band pass characteristic of having 805 nm. in the center and the filter 58f is made to be of a characteristic of transmitting a wavelength range of more than 850 nm. The above mentioned ICG is mixed in blood. When the filters 58e, 58f and 58b corresponding respectively to the wavelength ranges of IR2, IR3 and G come into the light path, the strobo lamp 24S will emit a light. When the object is displayed in quasi colors by the combination of the wavelength ranges of the above mentioned IR2, IR3 and G, the running state of the veins below the mucous membrance will be able to be confirmed by the difference between the outputs of IR2 and IR3. Also, by the picture image by G, the concavo-convexes and congested state on the surface of the mucous membrane can be definitely confirmed and the diagnosing activity can be improved.

As shown in FIG. 18(F), when a filter corresponding to a specific single wavelength range comes into the light path, the strobo lamp 24S will emit a light and the object image of this wavelength range will be monocolor-displayed.

When the above mentioned rotary filter 58 is stopped in the position in which the filter 58j transmitting W is interposed in the light path, the light of the visible light range will be constantly emitted and therefore the naked eye observation will be able to be made from the eyepiece part 65 of the fiberscope 60.

Thus, according to this embodiment, even if not only such electronic endoscope 1 as is shown in the first to fourth embodiments but also the generally used fiberscope 60 is used, the observation will be possible by selecting any wavelength range in wavelength ranges including others than the visible light range.

The other operations and effects are the same as in the fourth embodiment.

Figure 19:
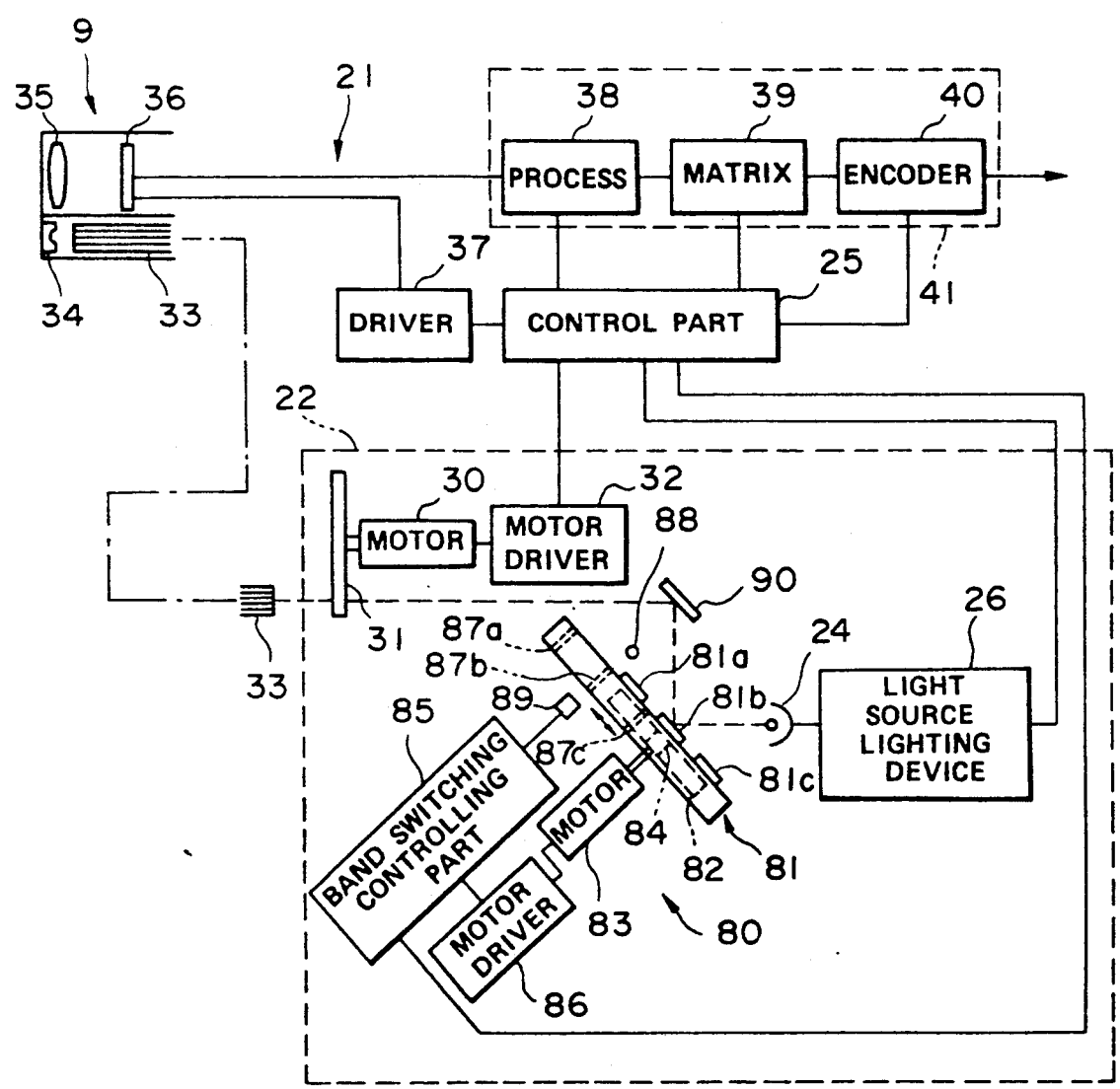
FIGS. 19 to 21 relate to the sixth embodiment of the present invention.
Figure 20:
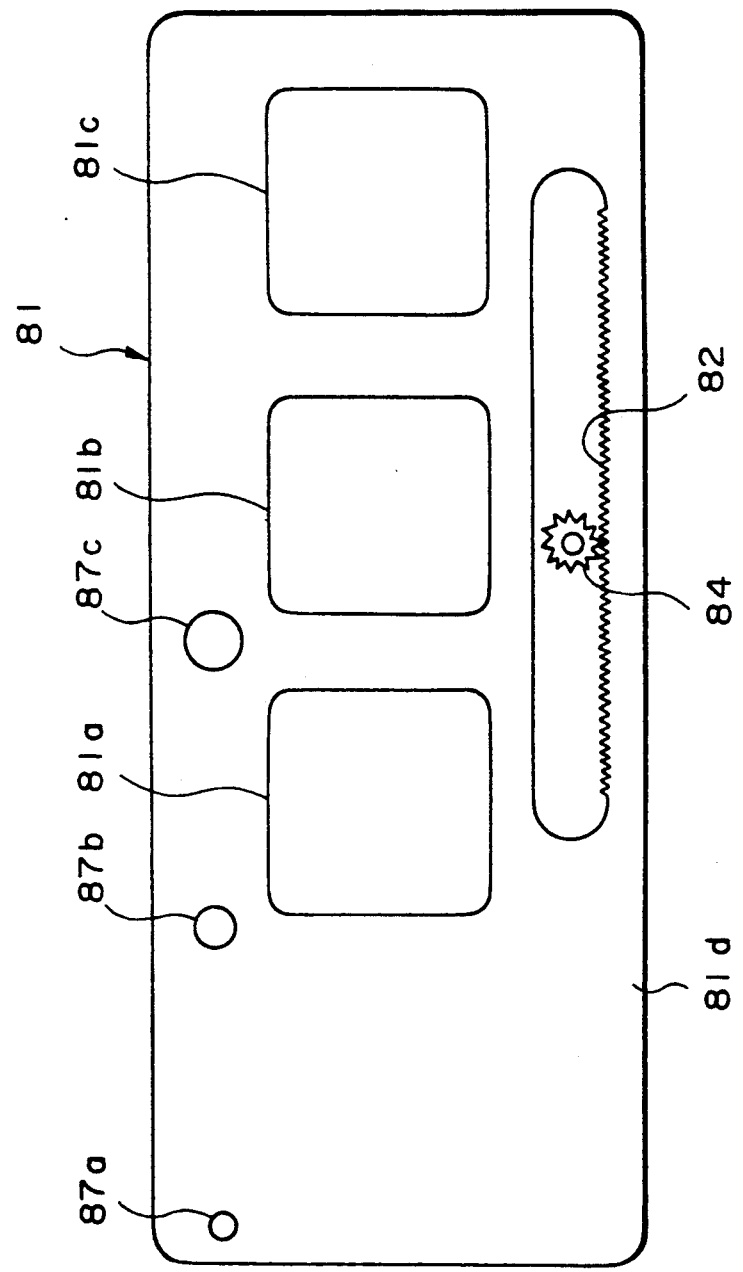
Figure 21:
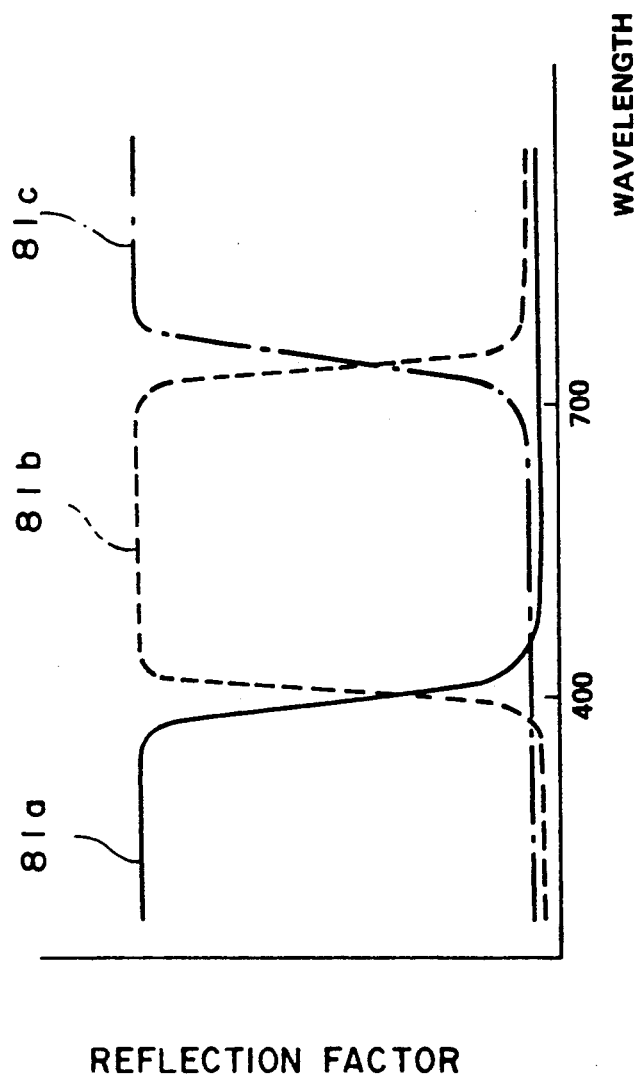

The sixth embodiment of the present invention is shown in FIGS. 19 to 21.

In this embodiment, a reflecting mirror is used as a selecting means instead of the band switching filter 27 in the first embodiment.

As shown in FIG. 19, a band switching apparatus 80 is provided within the light source part 22. As shown in FIG. 20, this band switching apparatus 80 is provided with a band switching mirror 81 having three mirrors 81a, 81b and 81c arranged in a row and respectively different in reflective characteristic. This band switching mirror 81 is arranged to reflect at a predetermined angle the emitted light from the above mentioned light source 24 and is movable in the arranging direction (the direction indicated by the arrows in the drawing) of the mirrors 81a, 81b and 81c along a rail (not illustrated) so that the light emitted from the above mentioned light source 24 may be reflected selectively by any of the mirrors 81a, 81b and 81c.

The reflective characteristics of the above mentioned mirrors 81a, 81b and 81c are as shown, for example, in FIG. 21.

That is to say, the mirror 81a reflects only substantially the ultraviolet light range, the mirror 81b reflects only substantially the visible light range and the mirror 81c reflects only substantially the infrared light range.

Also, as shown in FIG. 20, a rack 82 is provided in the moving direction on a frame 81d of the above mentioned band switching mirror 81. A pinion gear 84 rotated by a motor 83 is meshed with this rack 82. The above mentioned motor 83 is rotated by a motor driver 86 controlled by a band switching controlling part 85. The above mentioned band switching mirror 81 is moved by rotating the above mentioned pinion gear 84. Three kinds of aperture windows 87a, 87b and 87c of apertures of respectively different areas are provided at intervals equal to those of the above mentioned mirrors 81a, 81b and 81c in the moving direction. A light emitting device 88 and light receiving sensor 89 are provided in the positions holding the above mentioned band switching mirror 81 and opposed selectively to the above mentioned aperture windows 87a, 87b and 87c so that the output of this light receiving sensor 89 may be input into the above mentioned band switching controlling part 85. The above mentioned aperture window 87a is provided in the position opposed to the light emitting device 88 and light receiving sensor 89 when the mirror 81a is interposed in the illuminating light path. The aperture 87b is provided in the position opposed to the light emitting device 88 and light receiving sensor 89 when the mirror 81b is interposed in the illuminating light path. The aperture window 87c is provided in the position opposed to the light emitting device 88 and light receiving sensor 89 when the mirror 81c is interposed in the illuminating light path. In the above mentioned band controlling part 85, which of the mirrors 81a, 81b and 81c is interposed in the illuminating light path can be discriminated by the difference in the amount of light received by the above mentioned light receiving sensor 89.

The light reflected by any of the above mentioned mirrors 81a, 81b and 81c is reflected by a mirror 90 reflecting the light of all the ultraviolet to infrared band. The light reflected by the mirror 90 enters the rotary filter.

The other formations are the same as in the first embodiment.

In this embodiment, when any of the ultraviolet visible and infrared observing bands is selected in the band switching controlling part 85, the motor 83 will be rotated through the motor driver 86 and the band switching mirror 81 will be moved in the directions indicated by the arrows in the drawing. When any of the mirrors 81a, 81b and 81c corresponding to the selected band is interposed in the illuminating light path, any of the aperture window 87a, 87b and 87c corresponding to this mirror will be positioned between the light emitting device 88 and light receiving sensor 89 and the light emitted from the light emitting device 88 will be received by the light receiving sensor 89 through the above mentioned aperture window. In case the light amount received by this light receiving sensor 89 coincides with the light amount set in advance by the area of the aperture window corresponding to the selected band, the rotation of the above mentioned motor 83 will be stopped and the band switching mirror 81 will be stopped. Thus, the mirror reflecting only the light of the selected band will be interposed in the illuminating light path. The lights reflected by the mirrors 81a, 81b and 81c are reflected by the mirror 90 and enter the entrance end of the light guide 33.

For example, when the visible band is selected, as shown in FIG. 19, the mirror 81b, reflecting only the visible light, will be interposed in the illuminating light path and the light emitted from the light source 24 will be reflected by the mirror 81b to be a visible light and will be further transmitted through the rotary filter 31 to be divided in time series into light of the respective wavelength bands of R, G and B. When the ultraviolet band is selected, the mirror 81a reflecting only the ultraviolet light will be interposed in the illuminating light path and the light emitted from the light source 24 will be reflected by the mirror 81a to be an infrared light and will be further transmitted through the rotary filter 31 to be divided in time series into light of the respective wavelength bands of UV1, UV2 and UV3. In case the infrared band is selected, the mirror 81c reflecting only the infrared light will be interposed in the illuminating light path and the light emitted from the light source 24 will be reflected by the mirror 81c to be an infrared light and will be further transmitted through the rotary filter 31 to be divided in time series into light of the respective wavelength bands of IR1, IR2 and IR3.

The other operations and effects are the same as in the first embodiment.

The above mentioned mirrors 81a, 81b and 81c are not limited to be divided into the ultraviolet, visible and infrared ranges but may have any spectral characteristics.

Figure 22:
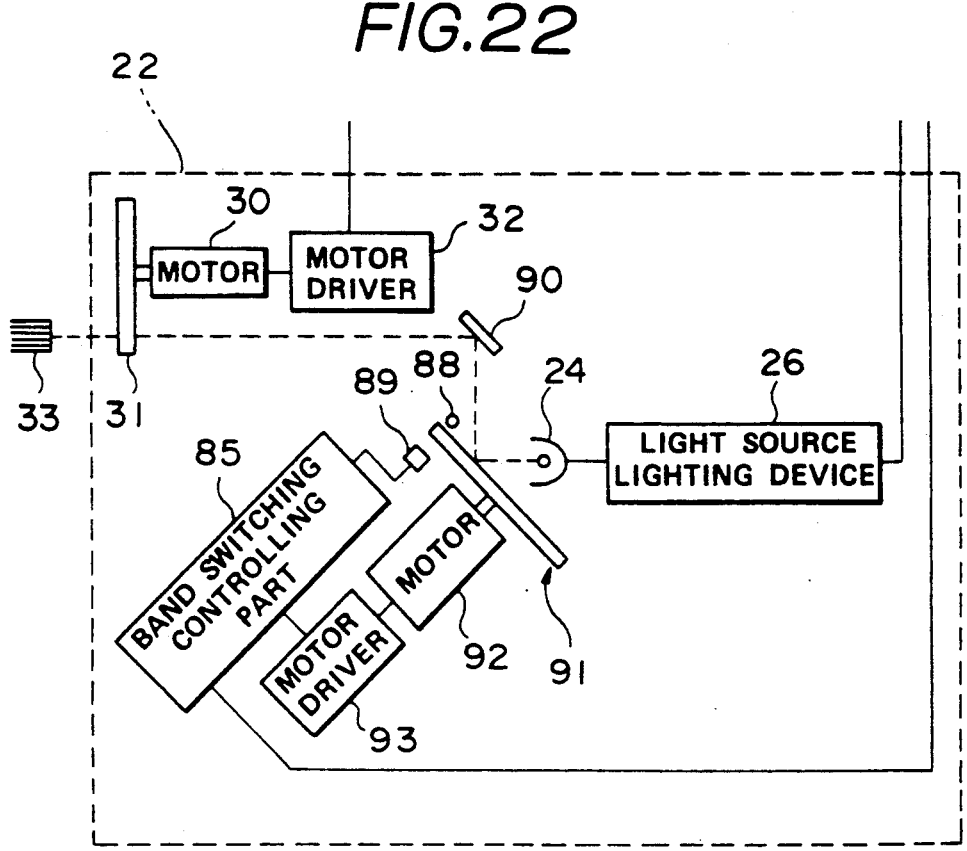
FIG. 22 is an explanatory view showing a modification of a light source part in the sixth embodiment.
Figure 23:
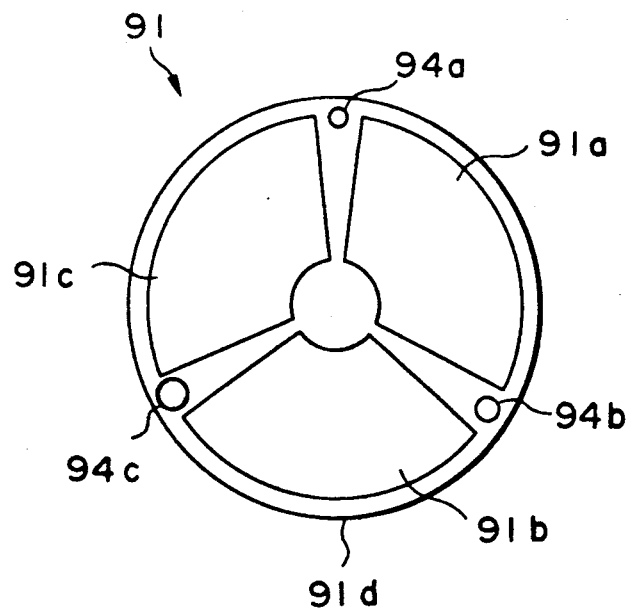
FIG. 23 is an elevation of a band switching mirror in a modification of the sixth embodiment.

A modification of the sixth embodiment is shown in FIGS. 22 and 23.

In this modification, a rotary mirror 91 in which the observing band is switchable by rotation is provided instead of the band switching mirror 81 in the sixth embodiment.

In the above mentioned rotary mirror 91, as shown in FIG. 23, a disc-like frame 91d is divided into three parts in the peripheral direction and a mirror 91a reflecting only the ultraviolet light, mirror 91b reflecting only the visible light and mirror 91c reflecting only the infrared light are provided in the divided respective parts. This rotary mirror 91 is rotated and driven by a motor 92. This motor 92 is rotated by a motor driver 93 controlled by the band switching controlling part 85. As shown in FIG. 23, in the above mentioned rotary mirror 91, three kinds of aperture windows 94a, 94b and 94c of apertures of respectively different areas are provided in the rotating direction in response to the above mentioned mirrors 91a, 91b and 91c. The same as in the sixth embodiment, the above mentioned aperture windows 94a, 94b and 94c are to be selectively positioned between the light emitting device 88 and light receiving sensor 89 arranged to hold the above mentioned rotary mirror 91. Which of the mirrors 91a, 91b and 91c is interposed in the illuminating light path can be discriminated by the amount of light received by the above mentioned light receiving sensor 89.

The other formations, operations and effects are the same as in the sixth embodiment.

Figure 24:
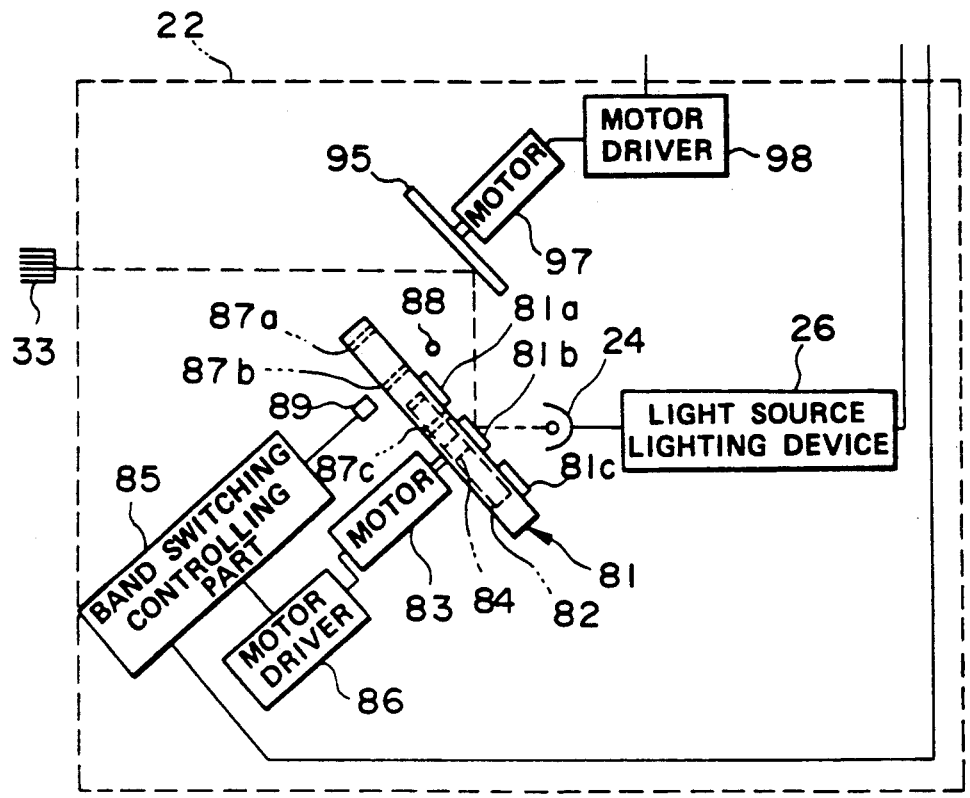
FIGS. 24 and 25 relate to the seventh embodiment of the present invention.
Figure 25:
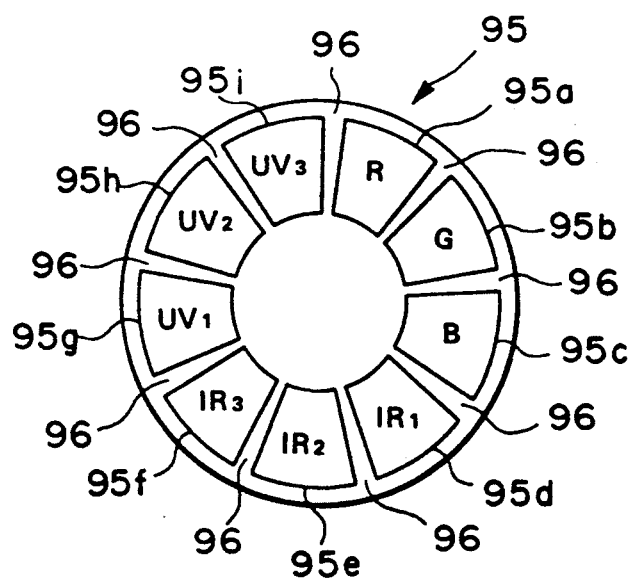

The seventh embodiment of the present invention is shown in FIGS. 24 and 25.

In this embodiment, a rotary mirror 95 is provided instead of the rotary filter in the sixth embodiment.

In the above mentioned rotary mirror 95, as shown in FIG. 25, a disc-like frame is divided into nine parts in the peripheral direction and mirrors 95a to 95i reflecting respectively only R, G, B, IR1, IR2, IR3, UV1, UV2 and UV3 are arranged in this order in the divided respective parts. Light intercepting parts 96 reflecting no light of any band are provided between the respective mirrors 95a to 95i. The above mentioned rotary mirror 95 is rotated and driven by a motor 97 which is rotated by a motor driver 98 controlled by the control part 25.

The above mentioned rotary mirror 95 is so arranged that the light reflected by the band switching mirror 81 may be reflected by any of the mirrors 95a to 95i and this reflected light may enter the entrance end of the light guide 33.

The other formations are the same as in the sixth embodiment.

In this embodiment, any of the observing bands of the ultraviolet, visible and infrared light is selected by the band switching mirror 81 and is divided in time series into light of respective wavelength bands of R, G and B.

The other operations and effects are the same as in the sixth embodiment.

In the above, the rotary mirror 91 in the modification of the sixth embodiment may be used instead of the band switching mirror 81 or the band switching filter 27 in the first embodiment may be used.

The eighth embodiment of the present invention is shown in FIGS. 26 to 29.

Figure 26:
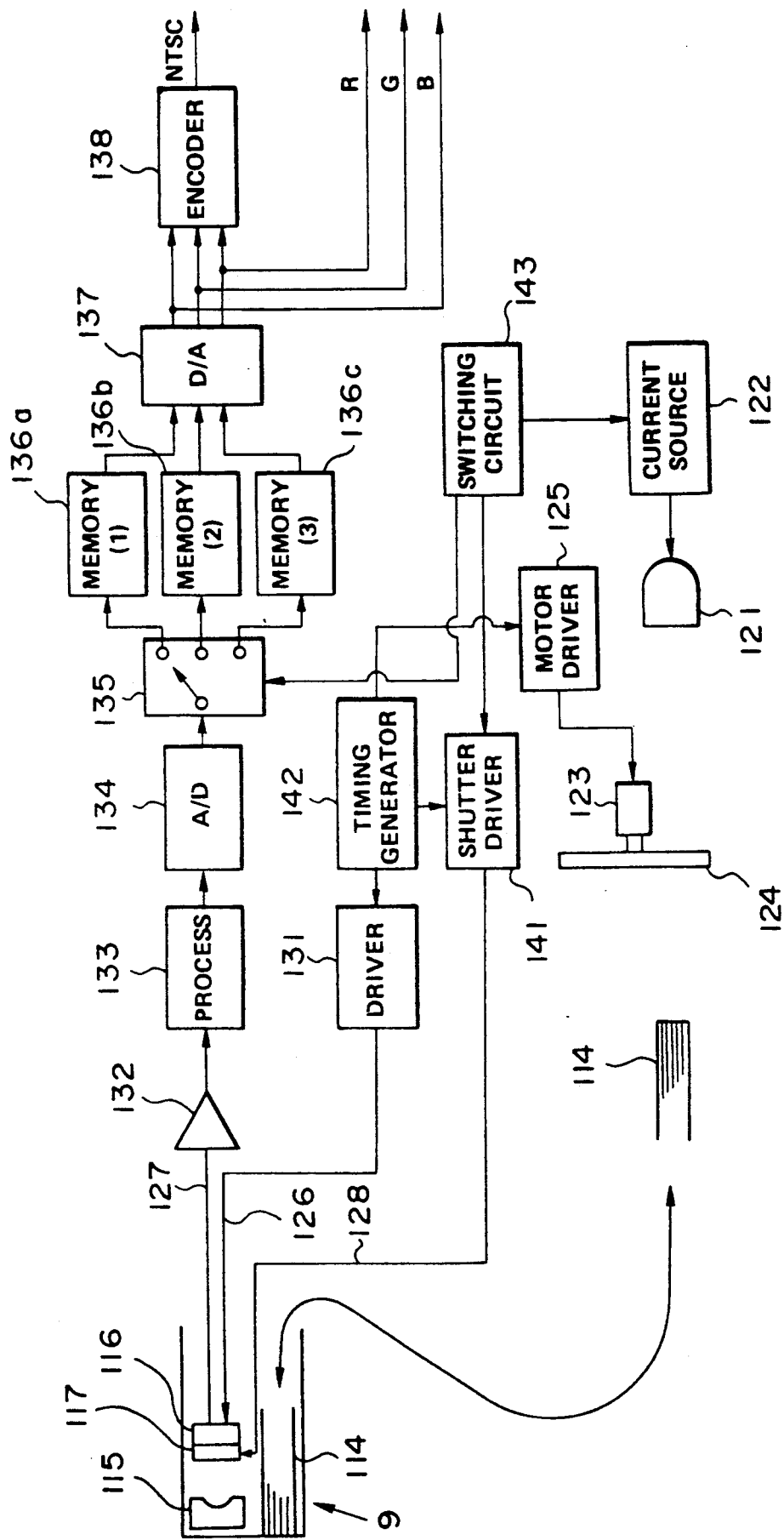
FIGS. 26 to 29 relate to the eighth embodiment of the present invention.

As shown in FIG. 26, a light guide 114 transmitting an illuminating light in inserted through the insertable part of the electronic endoscope 1. The tip surface of this light guide 114 is arranged in the tip part 9 of the insertable part 2 so that the illuminating light can be emitted from this tip part 9. The above mentioned light guide 114 is inserted on the entrance end side throughout the universal cord 4 and is connected to the connector 5. An objective lens system 115 is provided in the above mentioned tip part 9. A solid state imaging device 116 is arranged in the image forming position of this objective lens system 115 and has a sensitivity to a wide wavelength range from the ultraviolet range to the infrared range and including the visible range. A liquid crystal shutter 117 temporarily intercepting the light entering this solid state imaging device 116 is provided on the front surface of this solid state imaging device 116. Signal lines 126 and 127 are connected to the above mentioned solid state imaging device. A signal line 128 is connected to the above mentioned liquid crystal shutter 117. These signal lines 126, 127 and 128 are inserted through the above mentioned insertable part 2 and universal cord 4 and are connected to the above mentioned connector 5.

Figure 27:
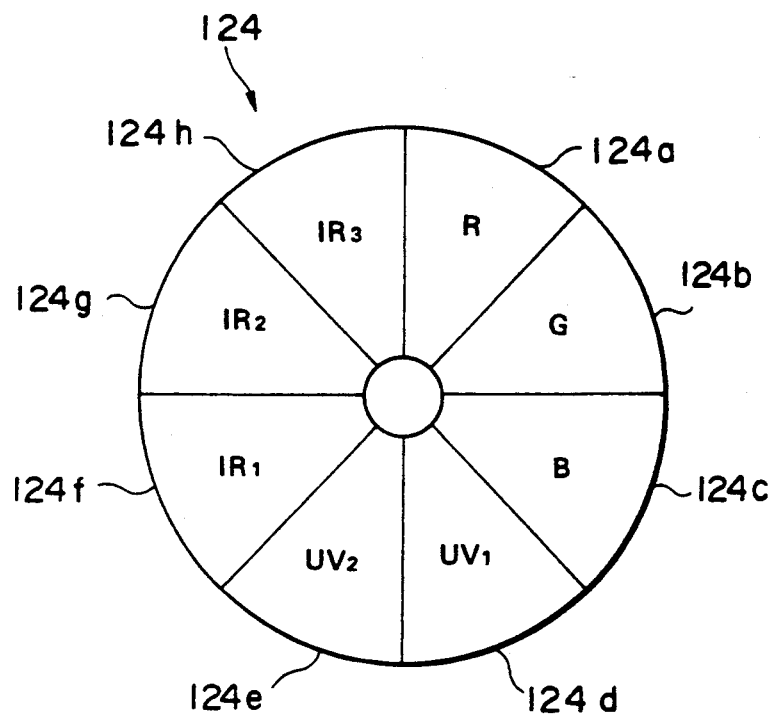
Figure 28:
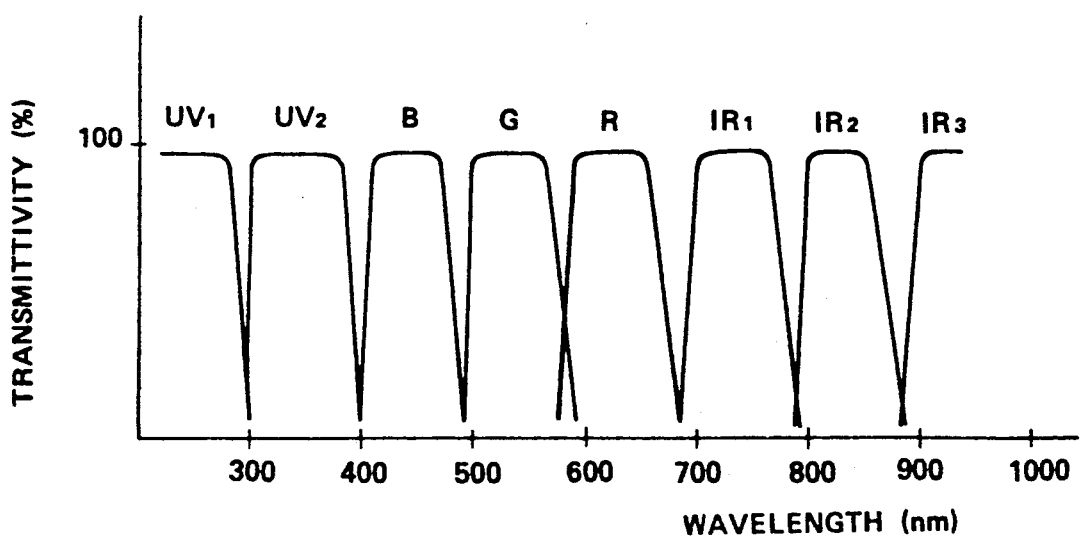

On the other hand, a lamp 121 emitting a light in a wide range from the ultraviolet light to the infrared light is provided within the control apparatus 6 A general xenone lamp or strobo lamp can be used for this lamp 121. The above mentined xenone lamp or strobo lamp emits a large amount of not only a visible light but also ultraviloet and infrared lights. This lamp 121 is fed with an electric power by a current source part 122. A rotary filter 124 as a dividing means rotated and driven by a motor 123 is arranged in front of the above mentioned lamp 121. as shown in FIG. 27, this rotary filter 124 is divided into eight parts in the peripheral direction. As shown in FIG. 28, filters 124a to 124h transmitting respectrively the red light (R), green light (G), blue light (B), first ultraviolet light (UV1), second ultraviolet light (UV2), first infrared light (IR1), second infrared light (IR2) and third infrared light (IR3) and having a band pass characteristic of selectively transmitting the wavelength of a narrow band over ultraviolet light to infrared light bands are arranged in this order in the divided respective parts. The above mentioned first to third infrared light are different from each other in the wavelength range and the wavelength is longer in the order of IR1, IR2 and IR3. In the same manner, the above mentioned first and second ultraviolet light are different from each other in the wavelength range and the wavelength is longer in the order of UV1 and UV2. The above mentioned motor 123 is controlled to be rotated and driven by a motor driver 125.

The light having passed through the above mentioned rotary filter 124 enters the entrance end of the above mentioned light guide 114, is led to the tip part 9 through this light guide 114 and is emitted out of this tip part 9 to illuminate the observed position.

The returning light. from the observed position by this illuminating light is made to form an image on the solid state imageing device 116 by the objective lens system 115 and is photoelectrically converted. A driving pulse from a driver circuit 131 within the above mentioned control apparatus 6 is applied to this solid state imaging element 116 through the above mentioned signal line 126. The reading out and transfer are made by this driving pulse. The video signal read out of this solid state imaging device 116 is input into a pre-amplifier 132 provided within the above mentioned control apparatus 6 or electronic endoscope 1 through the above mentioned signal line 127. The video signal amplified by this pre-amplfier 132 is input into a processing circuit 133, is processed to be γ-corrected and white-balanced and is converted to a digital signal by an A/D converter 134. This digital video signal is to selectively stored in three memories (1)136a, (2)136b and (3)136c corresponding to the respective colors, for example, of red (R), green (G) and blue (B) by a selecting circuit 135. The signals of the above mentioned memories (1)136a, (2)136b and (3)136c are simultaneously read out, are converted to analogue signals by a D/A converter 137, are output as R, G and B color signals, are input into an encoder 138 and are output out of this encoder 138 as an NTSC composite signal.

The above mentioned R, G and B color signals or NTSC composite signal is input into the color monitor 7 and the observed position is color-displayed by this color monitor 7.

The above mentioned liquid crystal shutter 117 is connected to a shutter driver 141 within the above mentioned control apparatus 6 through the signal line 128 and is opened and closed by this shutter driver 141.

A timing generator 142 making a timing of the entire system is provided within the above mentioned control apparatus 6 so that such respective circuits as the motor drive 25 and driver circuit 131 may be synchronized.

Within the above mentioned control apparatus 6, there is provided a switching circuit 143 controlling the shutter driver 141 so that, as synchronized with the above mentioned timing generator, the light may enter the solid state imaging device 116 only at the time of the illumination by the filter of any transmitted wavelength range of the operator in the above mentioned rotary filter 124. Also, this switching circuit 143 controls the above mentioned selecting circuit 135 so that the video signals corresponding to the respective wavelength ranges selected by the liquid crystal shutter 117 driven by the above mentioned. shutter driver 141 may be stored in the respectively different memories 136a to 136c. Further, the above mentioned switching circuit 143 controls the current source part 122 so that, when the above mentioned liquid crystal shutter 117 is closed and the solid state imaging device 116 receives no light, the emitted light amount of the lamp 121 will be reduced.

The operation of this embodiment formed as in the above shall be explained in the following.

When the lamp 121 emits a light and the rotary filter 124 is rotated by the motor 123 in the light path of the light of this lamp 121, the light of the wavelength range in the wide band from the ultra-violet light to the infra-red light as emitted from the above mentioned lamp 121 will be transmitted in turn through the respective filters 124a to 124h of the above mentioned rotary filter 124 and will be separated in time series into color light of the wavelength range shown in FIG. 28. This light is radiated onto an observed object out of the tip part 9 of the insertable part 2 of the electronic endoscope 1 inserted in a body cavity through the light guide 114. The returning light from the observed object by this illuminating light is made to form an image on the solid state imaging device 116 by the object lens system 115.

Here, if, for example, any three wavelength ranges are selected from among the divided wavelength ranges as shown in FIG. 28, when the filters corresponding to the selected wavelength ranges from among the respective filters 124a to 124h of the above mentioned rotary filter are inserted in the illuminating light path, by the drive of the shutter driver 141, the liquid crystal shutter 117 will open, the above mentioned solid state imaging device 116 will be exposed and a video signal will be obtained. On the other hand, when the filters corresponding to the wavelength ranges not selected are inserted in the illuminating light path, the above mentioned liquid crystal shutter 117 will close and the above mentioned solid state imaging device 116 will not be exposed. Thus, only the video images of the object illuminated by the light transmitted through the filters corresponding to the wavelength ranges selected by the switching circuit 143 among the respective filters 124a to 124h of the rotary filter 124 will be read out in time series by the driver circuit 131 synchronized with the timing generator 142. The signals read out of this solid state imaging device 116 are amplified by the pre-amplifier 132, are processed to be γ-corrected and white-balanced by the processing circuit 133 and are then converted to digital signls by the A/D converter 134 and the video signals read out in time series by the selecting circuit 135 are stored respectively in the memories (1)136a, (2)136b and (3)136c corresponding to the respective colors of R, G and B for the respective wavelength ranges. The signals simultaneously read out of the memories 136a, 136b and 136c are converted to analogue signals by the D/A converter 137 and are output as R, G and B signals in the color monitor 7 capable of inputting R, G and B signals. Respective colors of R, G and B are alloted to the selected wavelength ranges and the observed object is displayed in quasi colors. Also, the above mentioned R, G and B signals are converted to an NTSC composite signal by the encoder 138, this signal is input into the color monitor and the observed object is displayed in quasi colors in the same manner. When respective transmitted wavelength ranges of R, G and B are selected and the respective colors of R, G and B are alloted to the respective transmitted wavelength ranges or R, G and B, an ordinary color picture image will be obtained.

As synchronized with the above mentioned timing generator 142, the above mentioned switching circuit 143 will reduced the emitted light amount of the lamp 121 when the liquid crystal shutter 117 is closed but will increase the emitted light amount of the lamp 121 when the liquid shutter 117 is opened.

Thus, according to this embodiment, any wavelength ranges can be selected from among the wavelength ranges divided as shown in FIG. 28 in the ranges of not only the visible range but also from the ultraviolet light range to the infrared light range, the observed object can be color-displayed with any color allotment and an optimum observing wavelength band can be selected in response to the observed object.

Therefore, the color tone difference in the respective positions of the observed object difficult to discriminate in a picture image in a general visible range can be easily detected and a disease can be easily detected.

Figure 29:
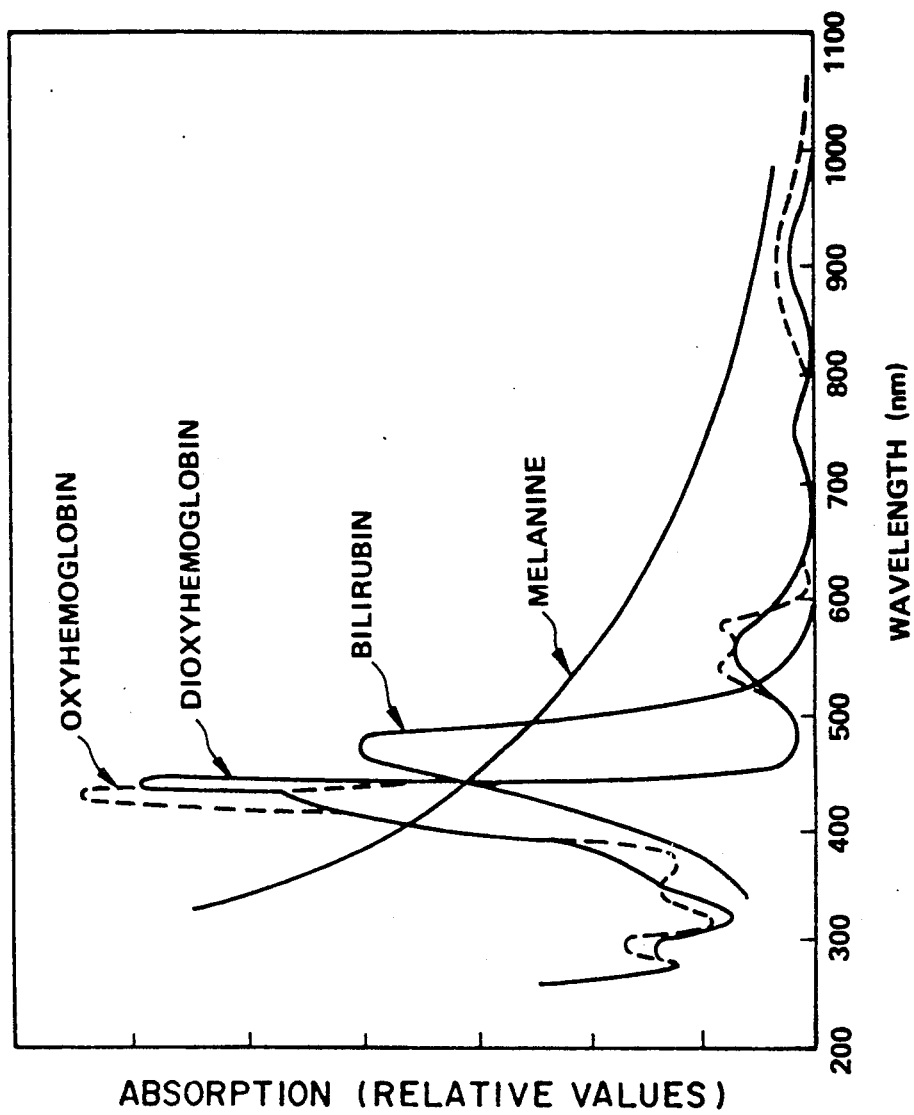

For example, as shown in FIG. 29, by selecting a wavelength range including absorption peaks different with the respective colors of a living body or a wavelength range in which the difference of the absorption factor with other colors is the largest, the color distribution in the living body tissue can be detected.

Further, by using a light of a long wavelength range above 600 nm. high in the transmittivity in a living body, the veins running below the mucous membrane and the pentration range of a disease can be easily observed. Thus, according to this embodiment, there is an effect that the diagnosing activity can be improved.

The solid state imaging device 116 may be a device provided with light intercepting parts to be transferred or a device provided with no light intercepting part.

Figure 30:
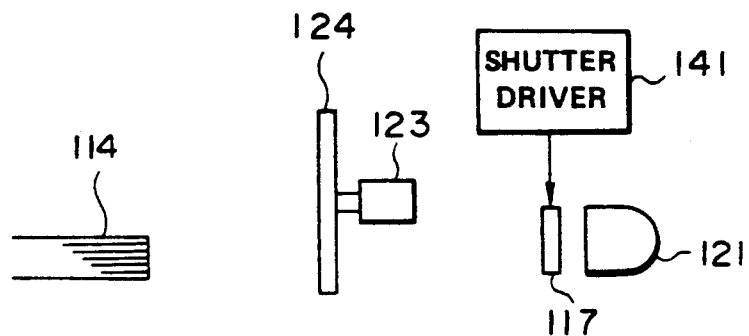
FIGS. 30 to 32 are explanatory views showing modifications of the eighth embodiment.
Figure 31:
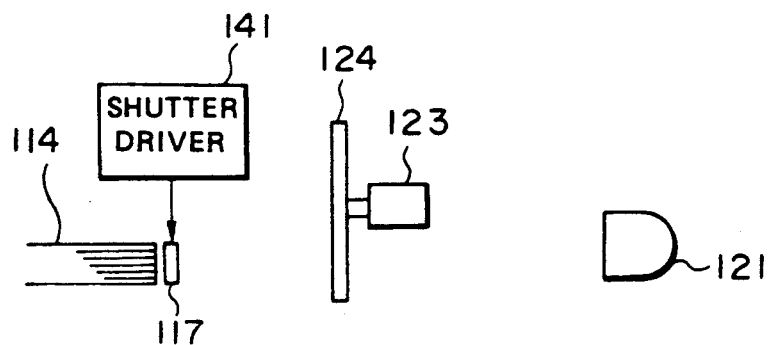
Figure 32:
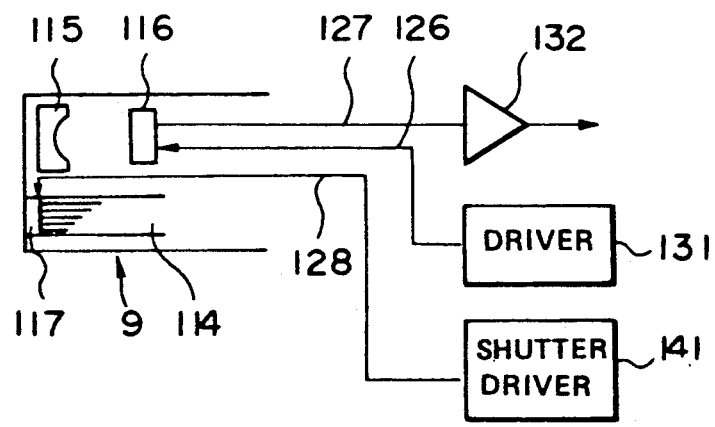

The position of the liquid crystal shutter 117 is not limited to be in front of the solid state imaging device 116 but may be between the lamp 121 and solid state imaging device 116. For example, the liquid crystal shutter 117 may be provided in front of the lamp 121 as shown in FIG. 30, at the entrance end of the light guide 114 as shown in FIG. 31 or at the exit end of the light guide 114.

Figures 33, 34A, 34B:
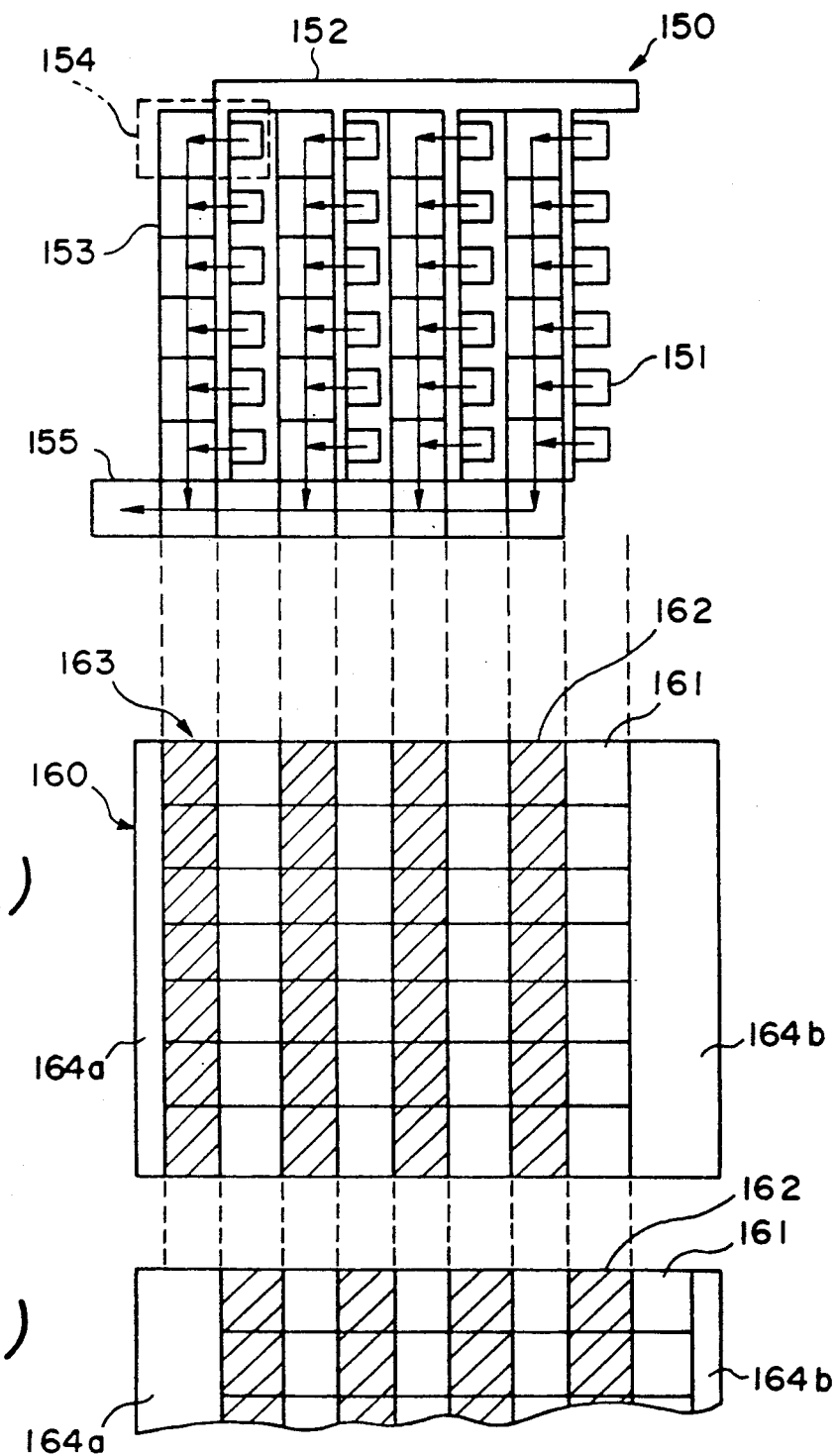

The ninth embodiment of the present invention is shown in FIGS. 33 and 34.

In this embodiment, the solid state imaging device 116 in the eighth embodiment is made an interline type CCD 150 and a shutter 160 using a piezoelectric device is provided instead of the liquid crystal shutter 160.

As shown in FIG. 33, the above mentioned CCD 150 has each picture element 154 formed of a photosensitive part 151 receiving a light and photoelectrically converting it to an electric signal, a read-out gate 152 reading out a signal charge accumulated in this photosensitive part and a vertically transferring CCD 153 transferring in the vertical direction the signal charge read out of this readout gate 152 and is further provided with a horizontally transferring CCD 155 transferring in the horizontal direction the charge transferred by the above mentioned vertically transferring CCd 153. The rate occupied by the above mentioned light receiving part 151 in the entire CCd 150 is less than 50% as there are the read-out gate 152 and vertically transferring CCD 153.

On the other hand, the above mentioned shutter 160 is arranged in front of the above mentioned CCD 150 and, as shown in FIG. 34(A), is formed of a filter 163 in which the width of each picture element 154 of the above mentioned CCd 150 is divided into two parts, a transmitting part 161 is arranged on one part and a light intercepting part 162 is arranged on the other part and piezoelectric devices 164a and 164b fitted to both end parts in the arranging direction of the transmitting part 161 and light intercepting part 162 of this filter 163. The above mentioned piezoelectric devices 164a and 164b are driven by a shutter driver 141 and , when one contracts, the other will extend so that the above mentioned filter 163 may be parallelly moved in the horizontal direction by half the picture element part. The transmitting part 161 can be switched to be positioned on the photosensitive part 151 of the CCD 150 as shown in FIG. 34(B) and the light intercepting part 162 can be switched to be positioned on the above mentioned photosensitive part 151.

The other formations are the same as in the eighth embodiment.

In this embodiment, the same as in the eighth embodiment, the light emitted from the lamp 121 is color-separated in time series by the rotary filter 124 and is radiated onto the observed position through the light guide 114. The returning light from this observed position is made to form an image on the above mentioned CCD 150 by the objective lines system 115.

Here, if any wavelength ranges are selected from among the wavelength ranges divided as shown in FIG. 28 by the switching circuit 143, when the filters corresponding to the selected wavelength ranges among the respective filters 124a to 124h of the above mentioned rotary filter 124 are inserted in the illuminating light path, the piezoelectric devices 164a and 164b will be driven and, as shown in FIGS. 34(A), the transmitting part 161 will be positioned on the photosensitive part 151 to make exposure. On the other hand, when the filters corresponding to the wavelength ranges not selected are inserted in the illuminating light path, as shown in FIG. 34(B), the light intercepting part 162 will be positioned on the above mentioned photosensitive part 151 to make no exposure.

Thus, according to this embodiment, the same as in the eighth embodiment, only the video images of the object illuminated by the light transmited through the filters corresponding to the wavelength ranges selected by the switching circuit 143 among the respective filters 124a to 124h of the rotary filter 124 will be read out in time series.

Also, in this embodiment, the transmitting part 161 and light intercepting part 162 of the above mentioned shutter 160 can be arranged in any proportion on the photosensitive part 151 of the CCD 150 without being perfectly switched over to each other. Thereby, the shutter 160 can be made to have the same function as a diaphragm. Therefore, when the reflection factors of the mucous membrane tissue in the respective wavelength ranges are extremely different, the video image by the respective wavelenght ranges can be made proper.

The other operations and effects are the same as in the eighth embodiment.

The tenth embodiment of the present invention is shown in FIGS. 35 to 38.

in this embodiment, a CCD 170 fitted with an electronic shutte is used instead of the solid state imaging device 116, liquid crystal shutter 117 and shutter driver 141 in the eighth embodiment.

As shown in FIG. 36, the above mentioned CCD 170 fitted with an electronic shutter is provided with an imaging part 173 formed of a light receiving part photoelectrically converting an optical picture image to a video signal and a vertically reading-out register 172 reading out the electric charge of this light receiving part, an accumulating part 174 accumulating the video signals of the respective lines of the above mentioned vertically reading-out register 172, a horizontally reading-out register 175 horizontally reading out as a video signal the electric charge accumulated in the above mentioned accumulating part 174 and a charge absorbing drain 176 absorbind the unnecessary charge read out by the above mentioned vertically reading-out register 172.

The above mentioned CCD 170 fitted with an electronic shutter is driven by a driver circuit 178.

In this embodiment, the same as in the eighth embodiment, the light emitted from the lamp 121 is color-separated in time series by the rotary filter 124 and is radiated onto the observed position through the light guide 114. The returning light from this observed position is made to form an image on the above mentioned CCD 170 fitted with an electronic shutter by the objective lens system 115.

Here, the driver circuit 178 driving the above mentioned CCd fitted with an electronic shutter operates as shown in FIGS. 37 and 38. The drawing shows an example that the video images of the respective wavelength ranges of G, IR2 and UV2 are quasicolored.

The same as in the eighth embodiment, as shown in FIG. 38(A), the light emitted from the lamp 121 is color-separated into the respective wavelength ranges of R, G, B, IR1, IR2, IR3, UV1 and UV2 by the rotary filter 124 and is radiated onto the observed position through the light guide 114. The returning light from this observed position is made to form an image on the above mentioned CCd 170 fitted with an electronic shutter. When quasi-coloring the video images of G, IR2 and UV1 as described above, first, as shown by (A) in FIG. 38(B), just before the required illumination by the G filter is made, as shown in FIG. 38(C), the video signal by the illuminating light accumulated by then in the light receiving parts 171 and transmitted through the other filters will be vertically read out of the light receiving parts 171 into the vertically reading-out register 172 as an unnecessary charge as shown in FIG. 37(A). This shall be temporarily called an (A) mode. Then, in FIG. 38(B), by a predetermined time in the illumination by the G filter indicated by (B) in FIG. 38(B), the above mentioned vertically reading-out register 172 will transfer the unnecessary charge to the charge absorbing drain 176. On the other hand, in the above mentioned (A) mode, the light receiving part 171 having read out the unnecessary charge will accumulate the video information by the illuminating light transmitted through the necessary G filter. Then, the signal charge accumulated in the above mentioned high receiving part 171 will be read out into the vertically reading-out register 172 and will be accumulated in the accumulating part 174. When the signal charge is transferred to the accumulating part 174 for the imaging part 173 as shown in FIG. 37(C) by a predetermined time indicated by (C) in FIG. 38(C), the signal will be read out as a video image by the illuminating light transmitted through the G filter by the horizontally reading-out register 175.

In the same manner, also in the case of the IR2 filter, the unnecessary charge by the illuminating lights transmitted through the B filter and IR1 filter will be read out and will be absorbed by the charge absorbing drain 176. On the other hand, since just after the unnecessary charge is read out, the signal charge by IR2 will be accumulated in the light receiving part 71, will be read out and transferred the same as in the case of the above mentioned G filter and will be read out as a video image by IR2 by the horizontally reading-out register 175.

The case of the UV2 filter is also the same.

The video signals corresponding to the illuminating lights transmitted through the respective filters B, IR2 and UV1 and thus read otu in time series are processed the same as in the eighth embodiment and are output as quasi-colored video images.

When a combination of other filters is selected, the driving pattern of the driver circuit 178 will be varied by the switching circuit 143 and the video signal will be output with any combination.

According to this embodiment, since there is no shutter part in front of the solid state imaging device and the device itself functions as a shutter, the tip part 9 of the electronic endoscope can be made small. Further, since there is no mechanical movable part as in the ninth embodiment, the size can be made small and the reliability can be elevated.

The eleventh embodiment of the present invention is shown in FIG. 39.

In this embodiment, the imaging apparatus of the tenth embodiment is applied to an externally fitted television camera fitted to the eyepiece part of a fiberscope.

The fiberscope 60 is of the same formation as is shown in the fifth embodiment and therefore its explanation shall be omitted.

An externally fitted television camera 180 is to be removably fitted to the eyepiece part 65 of the above mentioned fiberscope 60. This externally fitted television camera 180 is provided with an image forming lens 181 making the light from the above mentioned eyepiece part 65 from an image and a CCd 170 fitted with an electronic shutter and arranged in the image forming position of this image forming lens 181. The same as in the tenth embodiment, this CCD 170 fitted with an electronic shutter is driven by the driver circuit 178 within the control apparatus 6 and the signal read out is inptu into a pre-amplifier 132 and is processed the same as in the tenth embodiment.

The other formations, operations and effects are the same as in the tenth embodiment.

In this embodiment, the externally fitted television camera 180 fitted to the eyepiece part 65 of the fiberscope 60 is provided with the CCD 170 fitted with an electronic shutter as in the tenth embodiment but may be provided with the liquid crystal shutter 117 as in the eighth embodiment or may be provided with the shutter 160 using a piezoelctric device as in the ninth embodiment.

The twelfth embodiment of the present invention is shown in FIGS. 40 to 44.

In this embodiment, the light source is to emit lights ranging from the visible light range to the infrared light range. A band limiting filter 227 as a band limiting means is provided instead of the band switching filter 27 in the first embodiment and a rotary filter 231 is provided instead of the rotary filter 23.

Figure 41:
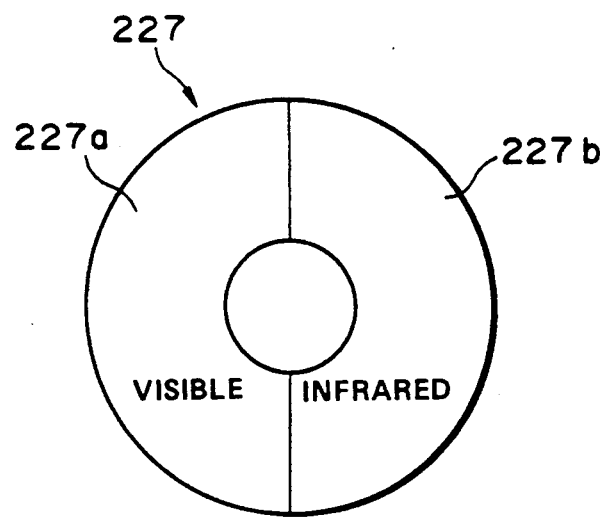
Figure 42:
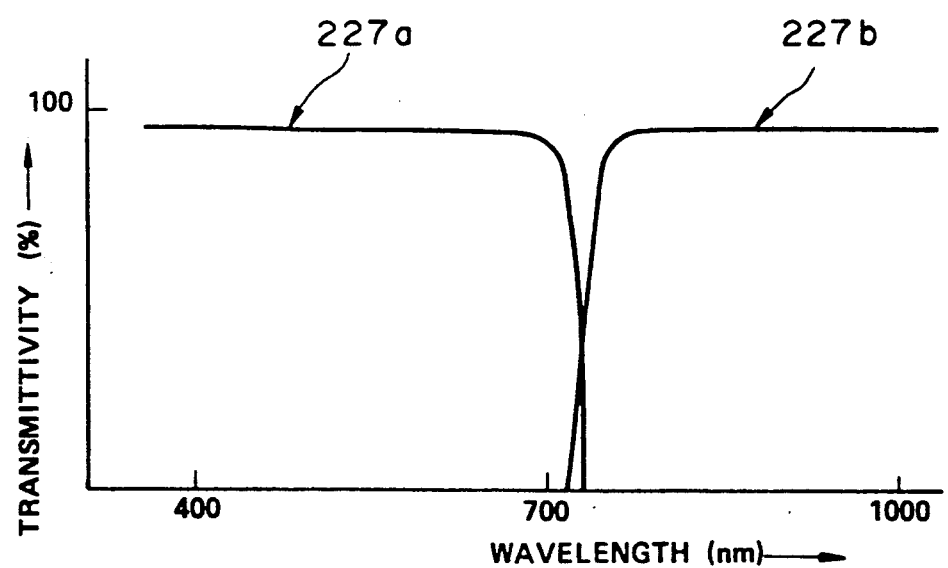

The above mentioned band limiting filter 227 is divided into two parts as shown in FIG. 41 and a filter 227a tranmitting the visible band and a filter 227b transmitting the infrared band as shown in FIG. 42 are arranged in the divided respective parts.Therefore, the light emitted from the above mentioned light source 24 will have either of the visible band and infrared band transmitted depending on the position of this band limiting filter 227.

Figure 43:
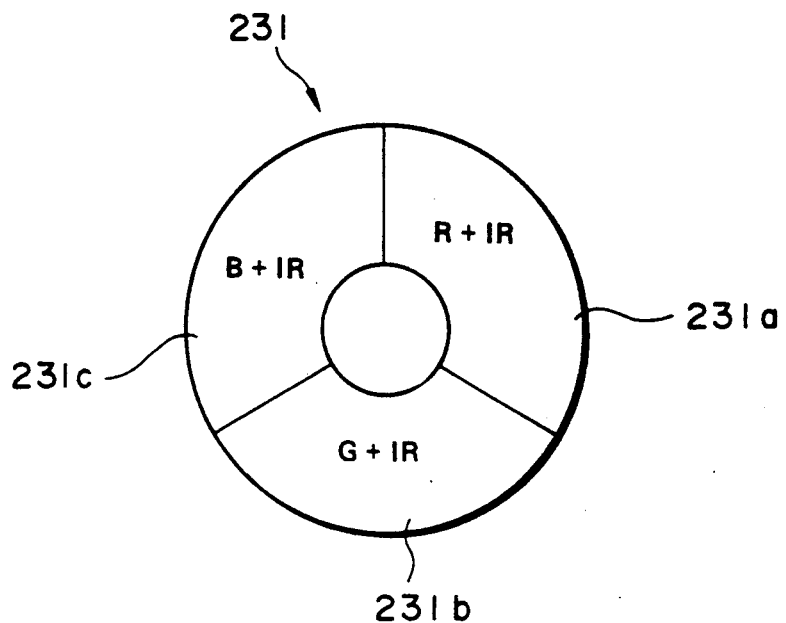
Figure 44:
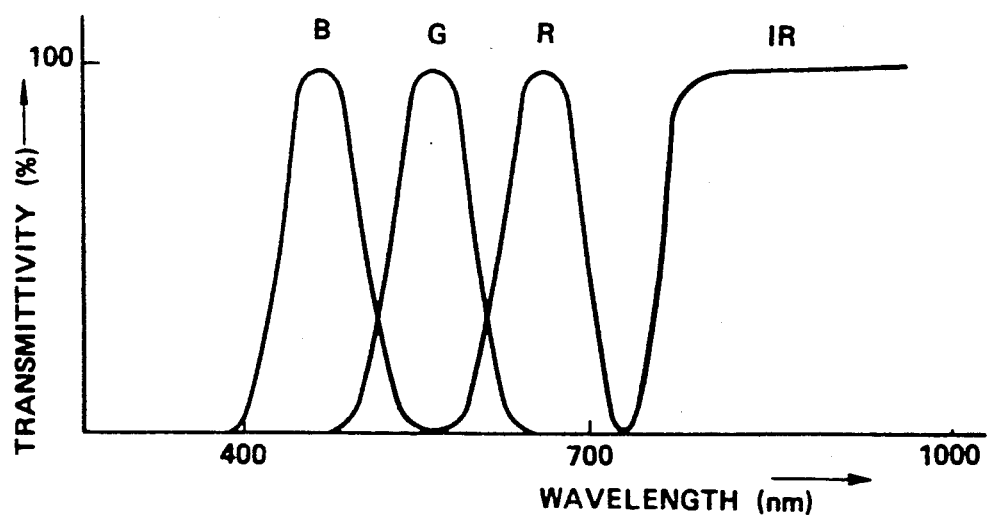

On the other hand, the above mentioned rotary filter 231 is divided into three parts in the peripheral direction as shown in FIG. 43. Filters 231a, 231b and 231c are provided repsectively in the divided parts. In this embodiment, the above mentioned respective filters have a double transmitting characteristic. As shown in FIG. 44, the filter 231a transmits R in the visible band and the infrared band IR, the filter 231b transmits G in the visible band and the infrared band IR and the filter 231c transmits B in the visible band and the infrared band IR.

The other formations are the same as in the first embodiment.

In this embodiment, the transmitted wavelength ranges of the respective filters of the above mentioned filter 231 are limited to wavelength ranges belonging to either of the visible band and infrared band by the above mentioned band limiting filter 227. That is to say, when the visible band is selected by the above mentioned band limiting filter 227, only the visible light will enter the rotary filter 231 and therefore the lights of R, G and B will be color-separated in time series by the above mentioned rotary filter 231 and will enter the entrance end of the light guide 33. On the other hand, when the infrared band is selected by the above mentioned band limiting filter 227, only the infrared light will enter the rotary filter 231, the above mentioned rotary filter 231 will not color-separate R, G and B and the light of the infrared band IR will be emitted from this rotary filter 231 and will enter the entrance end of the light guide 33.

In ease the visible band is selected by the above mentioned band limiting filter 227, the light of the respective wavelength ranges of R, G and B will be radiated in time series onto the observed object and the returning light from this observed object will be made to form an image on the solid state imaging device 36 by the objective lens system 35. This solid state imaging device 36 is driven by the driver 37. The signals read out of the solid state imaging device 36 in response to the respective wavelength ranges are to the respective colors of red, green and blue and are processed to be video signals in the video signal processing part 41. For example, the output signal of the above mentioned solid state imaging device 36 is amplified and γ-corrected in the process circuit 38 and the color signal is corrected in the matrix circuit 39 so as to reproduce the colors accurately in the color measurement. Further, the three kinds of picture images color-separated in the respective wavelength ranges are temporarily stored in the encoder 40, are converted to video signals observable with a general television monitor and are output in the monitor 7. Therefore, when the respective colors of red, green and blue are alloted to the respective wavelength ranges of R, G and B, an ordinary color picture image will be obtained.

On the other hand, when the infrared band is selected by the above mentioned band limiting filter 227, irrespective of the position of the rotary filter 231, the light of the infrared band IR will be radiated onto the observed object and the observed object image in the infrared band will be monocolor-displayed.

Thus, according to this embodiment, the color picture image in the visible range and the picture image in the infrared range can be switched over to each other and the disease and vein running state below the mucous membrane so far difficult to detect with only the visible light can be confirmed and the diagnosing activity can be improved.

Figure 45:
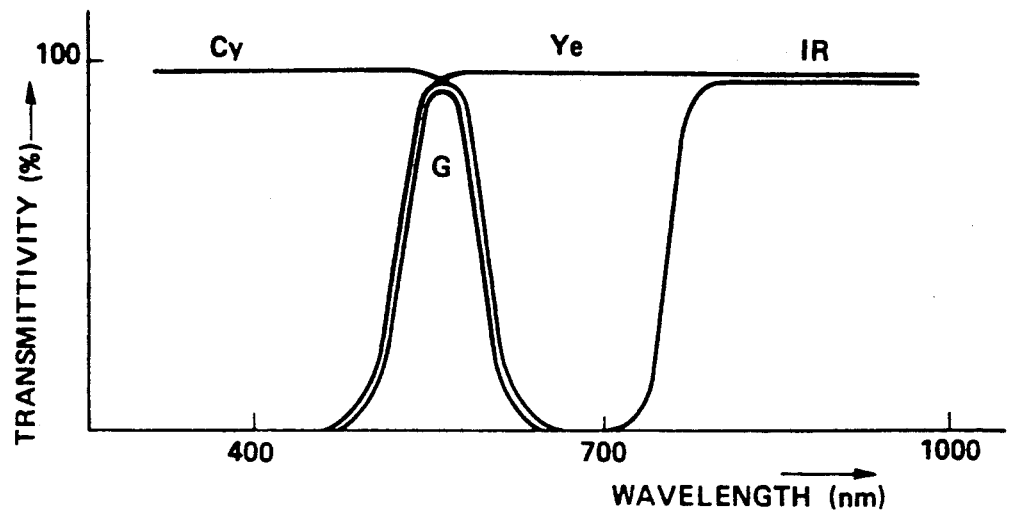
FIG. 45 is an explanatory diagram showing the transmitting characteristics of respective filters of a modification of the rotary filter in the twelfth embodiment.

The respective filters 231a, 231b and 231c of the above mentioned rotary filter 231 not only transmit respective R, G and B in the visible band as shown in FIG. 44 but also may transmit respectively yellow (Ye), green (G) and cyanine (Cy) in the visible band as shown, for example, in FIG. 45.

Figure 46:
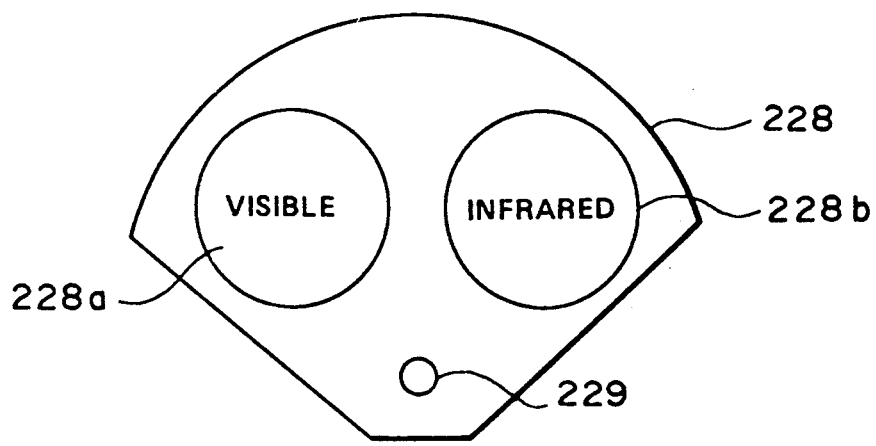
FIGS. 46 and 47 are explanatory views showing modifications of the band limiting filter in the twelfth embodiment.
Figure 47:
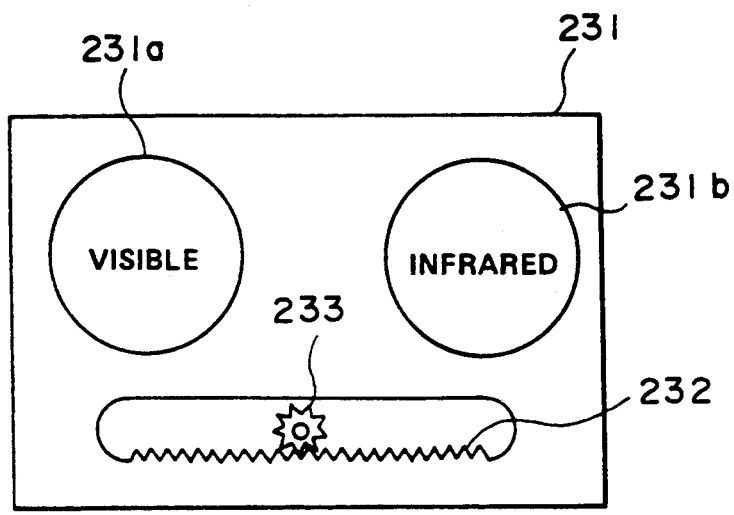

The above mentioned band limiting filter 227 is not limited to be disc-like as shown, for example, in FIG. 41 but also, as shown, for example, in FIG. 46, a filter 228a transmitting the visible band and a filter 228b transmitting the infrared band are arranged in the peripheral direction in a substantially fan-shaped frame 228 so that, when the frame 228 is rotated by a predetermined angle with the rotary shaft 229 as a center, either of the filters 228a and 228b may selectively interposed in the illuminating light path of the light source 24. Also, as shown in FIG. 47, the filter 231a transmitting the visible band and the filter 231b transmitting the infrared band are arranged on the left and right in the frame 231 so that, when the above mentioned frame 231 is moved in the rightward and leftward direction by a rack 232 provided in the rightward and leftward direction in the above mentioned frame 231 and a pinion 233 meshing with this rack 232, the above mentioned frame 231 may be moved in the rightward and leftward direction and thereby either of the filters 231a and 231b may be selectively interposed in the illuminating light path of the light source 24.

Figure 48:
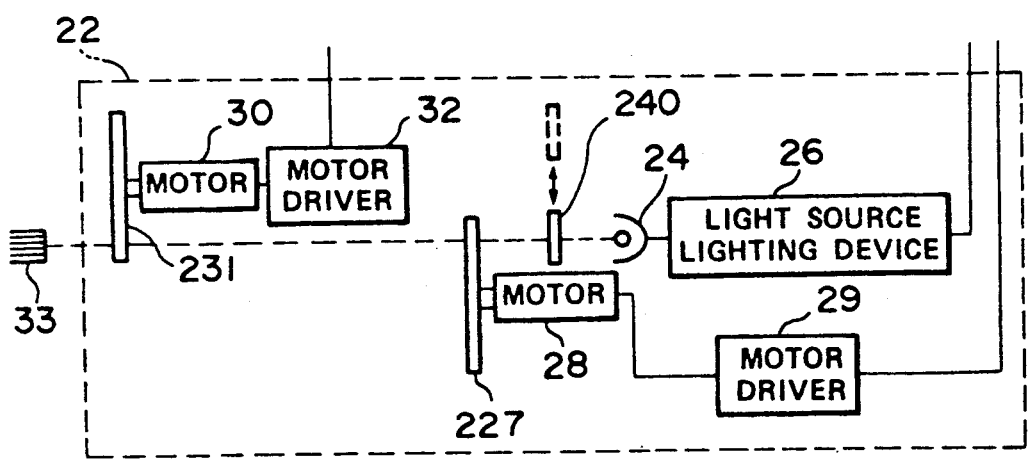
FIGS. 48 to 50 related to the thirteenth embodiment of the present invention.
Figure 49:
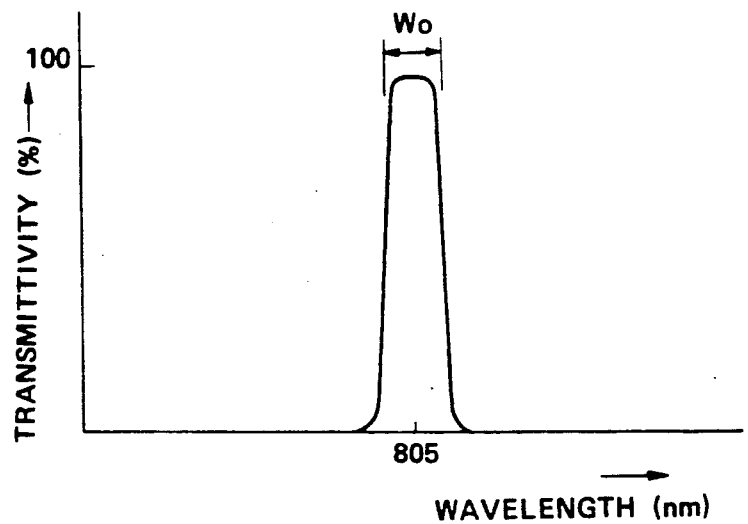
Figure 50:
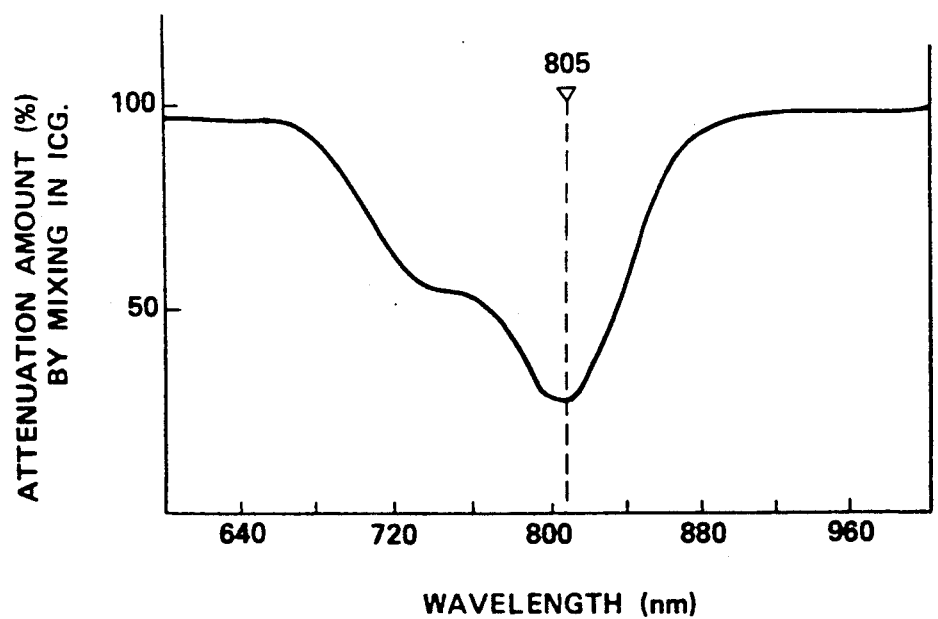

The thirteenth embodiment of the present invention is shown in FIGS. 48 to 50.

In this embodiment, a band limiting filter 240 is provided insertably in the illuminating light path of the light source 24 in the light source part 22 in the twelfth embodiment. The above mentioned band limiting filter 240 has a band pass characteristic of a narrow band having 805 nm. in the center as shown in FIG. 49. The transmitted wavelength band Wo of this band limiting filter 240 is so narrow as to be preferably less than about 40 nm.

The other formations are the same as in the twelfth embodiment.

FIG. 50 shows a difference in the spectral characteristic (the attenuation rate by mixing in ICG) between blood in which was mixed Indocyanine green (ICG) which is an infrared ray absorbing color and blood in which ICG was not mixed. As shown in this diagram, the blood in which ICG was mixed has a maximum absorption at 805 nm. Therefore, when ICG is mixed into blood, for example, by venous injection and the infrared band is selected by the band limiting filter 227 and the above mentioned band limiting filter 240 having a band pass characteristic in which the absorption factor has a maximum of 805 nm. in the center is interposed in the illuminating light path, a light of a narrow band having 805 nm. in the center will be radiated onto the observed object and the observed object image in this narrow band will be observed. The light having 805 nm. in the center will reach the deep part of the mucous membrane and will be absorbed in the venous part and therefore the venous part will be observed as a shadow. Therefore, as compared with the observation in other wavelength ranges, the vein running state can be observed in a much higher contrast.

The operation when the above mentioned band limiting filter 240 is retreated from the illuminating light path of the light source 24 is the same as in the twelfth embodiment. It is needless to say that the rotary filter 231 may have a transmitting characteristic as is shown in FIG. 45.

Figure 51:
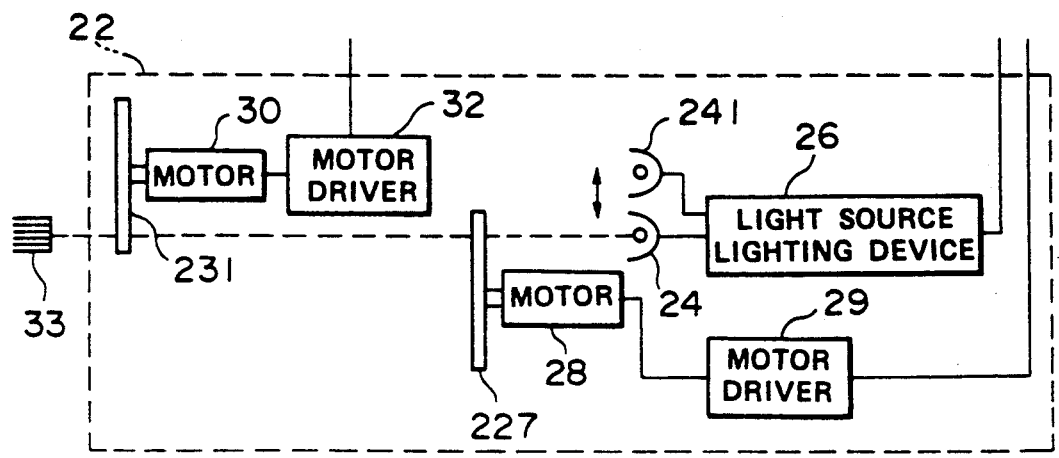
FIG. 51 is an explanatory diagram showing a light source part in a modification of the thirteenth embodiment.

A light source 241 as a laser or LED emitting a light of a narrow band having 805 nm. in the center as shown in FIG. 51 may be prepared instead of inserting the above mentioned band limiting filter 240 in the illuminating light path and may be used instead of the light source 24 emitting a light of a wide band in the case of observing the observed object image in the narrow band having 805 nm. in the center.

Figure 52:
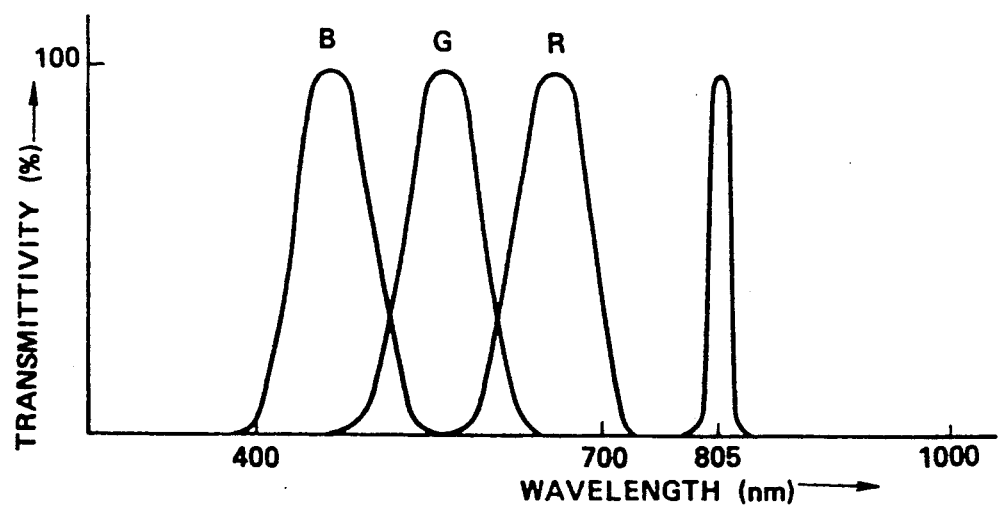
FIG. 52 is an explanatory diagram showing the transmitting characteristics of the respective filters of the rotary filter in the fourteenth embodiment of the present invention.

The fourteenth embodiment of the present invention is shown in FIG. 52.

In this embodiment, the transmitting characteristics of the respective filters 231a, 231b and 231c of the rotary filter 231 in the twelfth embodiment are so made that, as shown in FIG. 52, the filter 231a may transmit R in the visible band and the narrow band having 805 nm. in the center, the filter 231b may transmit G in the visible band and the narrow band having 805 nm. in the center and the filter 231c may transmit B in the visible band and the narrow band having 805 nm. in the center.

The other formations are the same as in the twelfth embodiment.

In this embodiment, when the visible band is selected by the band limiting filter 227, a color picture image by an ordinary visible band will be obtained. On the other hand, when the infrared band is selected by the above mentioned band limiting filter 227, only a light of the narrow band having 805 nm. in the center will be transmitted through the above mentioned rotary filter 231 and will be radiated onto the observed object and the observed object image in this narrow band will be observed.

The filters transmitting the narrow band having 805 nm. in the center need not be all of the filters 231a, 231b and 231c. For example, one filter may be made to have the above mentioned narrow band transmitting characteristic. In this case, when the rotary filter 231 is stopped in the position in which the filter transmitting this narrow band is interposed in the illuminating light path and the visible band is selected by the band limiting filter 227, the observed object image in the narrow band having 805 nm. in the center will be observed. Thus, even if only one filter is made to have the above mentioned narrow band transmitting characteristic, in the case of imaging in a field sequential system, the resolution will not reduce.

Figure 53:
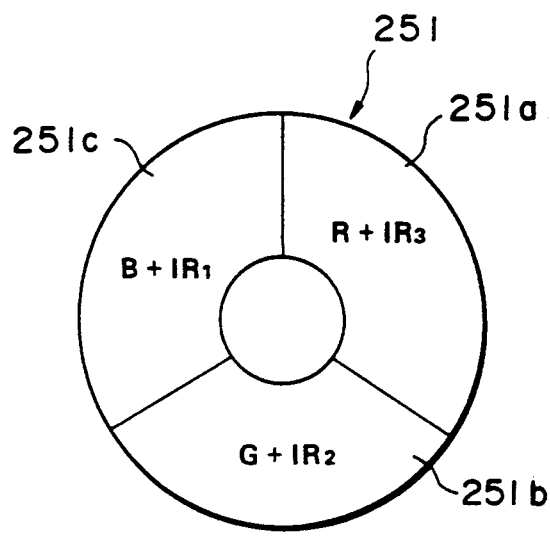
FIGS. 53 and 54 relate to the fifteenth embodiment of the present invention.
Figure 54:
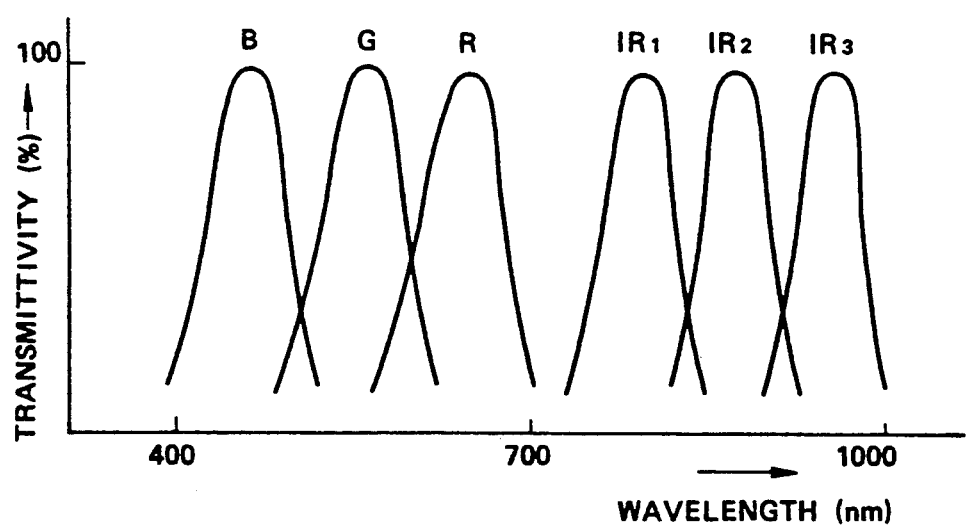

The fifteenth embodiment of the present invention is shown in FIGS. 53 and 54.

In this embodiment, a rotary filter 251 is provided instead of the rotary filter 231 in the twelfth embodiment.

As shown in FIG. 53, the above mentioned rotary filter 251 is divided into three parts and filters 251a, 251b and 251c are arranged in the divided respective parts. The respective filters 251a, 251b and 251c have a double transmitting characteristic. As shown in FIG. 54, the filter 251a transmits R in the visible band and IR3 in the infrared band, the filter 231b transmits G in the visible band and IR2 in the infrared band and the filter 231c transmits B in the visible band and IR1 in the infrared band.

The other formations are the same as in the twelfth embodiment.

In this embodiment, when the visible band is selected by the band limiting filter 227, the same as in the twelfth embodiment, the light of R, G and B will be color-separated in time series by the rotary filter 251 and a color picture image in an ordinary visible band will be obtained. On the other hand, when the infrared band is selected by the above mentioned band limiting filter 227, the light of IR1, IR2 and IR2 will be color-separated in time series by the above mentioned rotary filter 251 and three lights will be radiated onto the observed object. In the video signal processing part 41, the respective colors of red, green and blue are optionally alloted to the above mentioned wavelength ranges of IR1, IR2 and IR3 and the video signals are processed. Therefore, the observed object image of the infrared band is displayed in quasi colors.

According to this embodiment, the observed object image in the infrared band can be color-displayed and therefore the color tone difference in the respective positions of the observed object in the infrared band can be easily detected.

The sixteenth embodiment of the present invention is shown in FIGS. 55 to 58.

In this embodiment, the light source 24 is to emit light ranging from the visible light range to the ultraviolet light range. A band limiting filter 261 is provided instead of the band limiting filter 227 in the twelfth embodiment. A rotary filter 262 is provided instead of the rotary filter 231.

Figure 55:
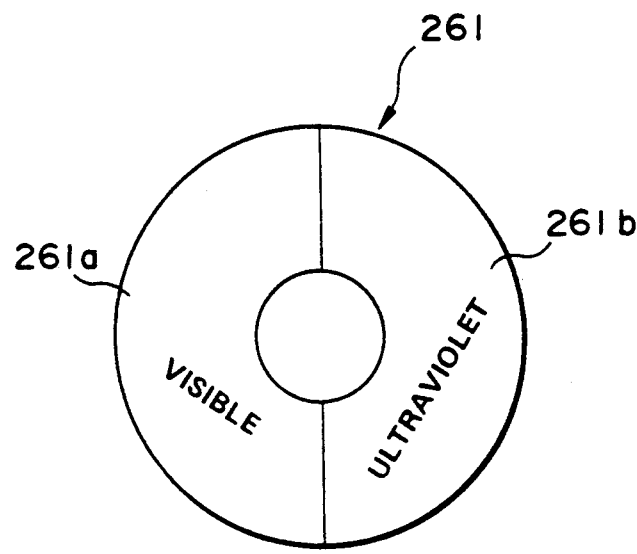
FIGS. 55 to 58 relate to the sixteenth embodiment of the present invention.
Figure 56:
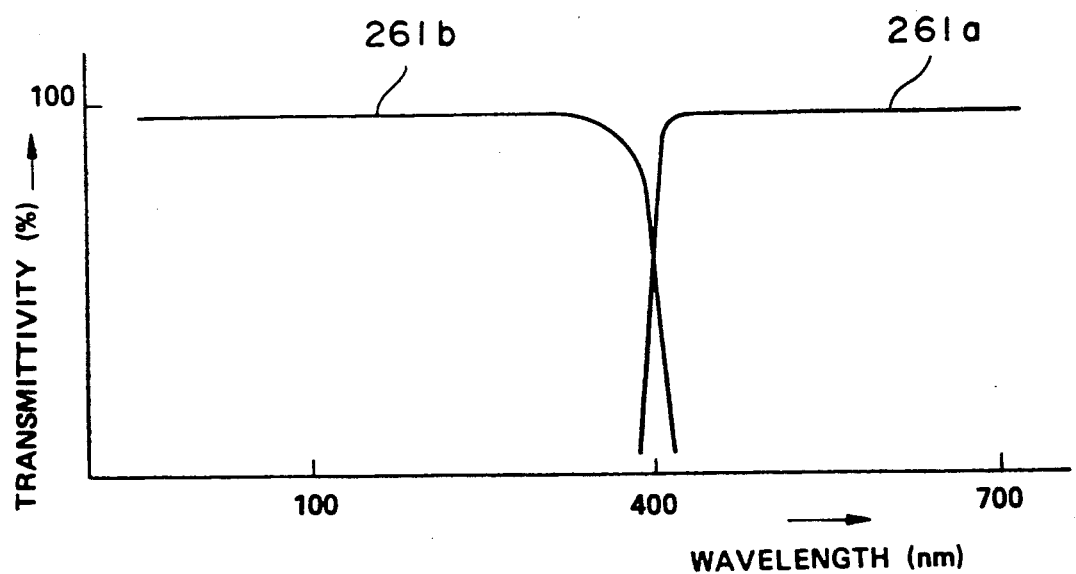

As shown in FIG. 55, the above mentioned band limiting filter 261 is divided into two parts in the peripheral direction. As shown in FIG. 56, a filter 261a transmitting the visible band and a filter 261b transmitting the ultraviolet band are arranged in the divided respective parts. Therefore, depending on the position of this band limiting filter 261, of the light emitted from the above mentioned light source 24, either of the visible band and ultraviolet band will be selectively transmitted.

Figure 57:
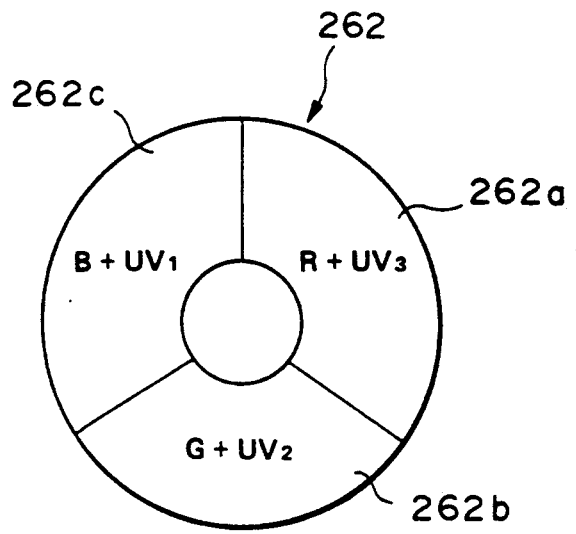
Figure 58:
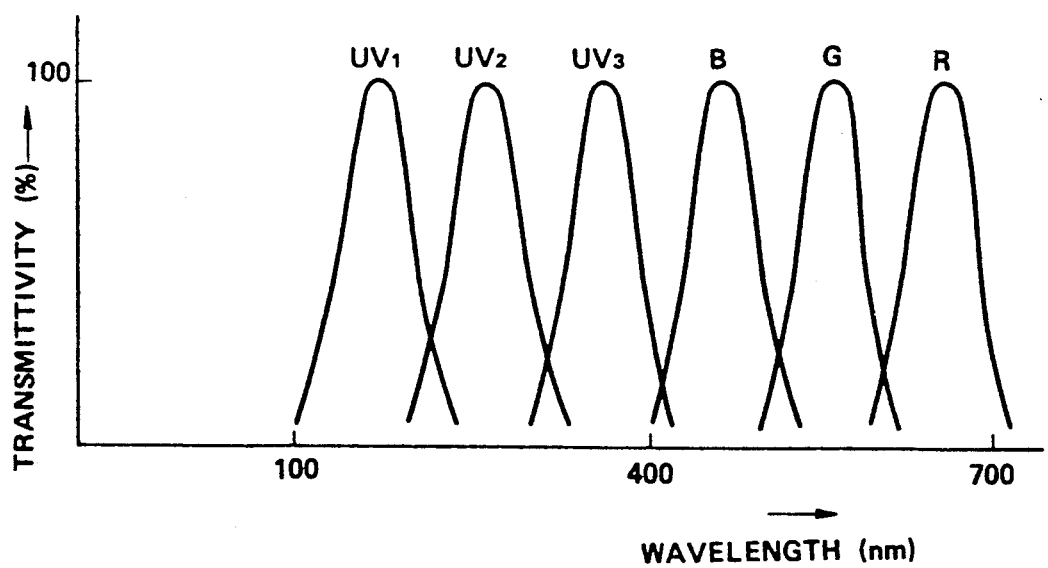

On the other hand, as shown in FIG. 57, the above mentioned rotary filter 262 is divided into three parts in the peripheral direction and filters 262a, 262b and 262c are arranged in the divided respective parts. In this embodiment, the above mentioned respective filters 262a, 262b and 262c have a double transmitting characteristic. As shown in FIG. 58, the filter 262a transmits R in the visible band and UV3 in the ultraviolet band, the filter 262b transmits G in the visible band and UV2 in the ultraviolet band and the filter 262c transmits B in the visible band and UV1 in the infrared band.

The other formations are the same as in the twelfth embodiment.

In this embodiment, when the visible band is selected by the band limiting filter 261, the same as in the twelfth embodiment, the light of R, G and B will be color-separated in time series by the rotary filter 262 and a color picture image in an ordinary visible range will be obtained. On the other hand, when the ultraviolet band is selected by the above mentioned band limiting filter 261, the light of UV1, UV2 and UV3 will be color-separated in time series by the above mentioned rotary filter 262 and will be radiated onto the observed object. In the video signal processing part 41, the respective colors of red, green and blue are optionally alloted to the above mentioned wavelength ranges of UV1, UV2 and UV3 to process video signals. Therefore, the observed object image in the ultraviolet band is displayed in quasi colors.

According to this embodiment, as the observed object image not only in the visible band but also in the ultraviolet band can be color-displayed, the color tone difference in the respective positions of the observed object in the ultraviolet band can be easily detected.

Figure 59:
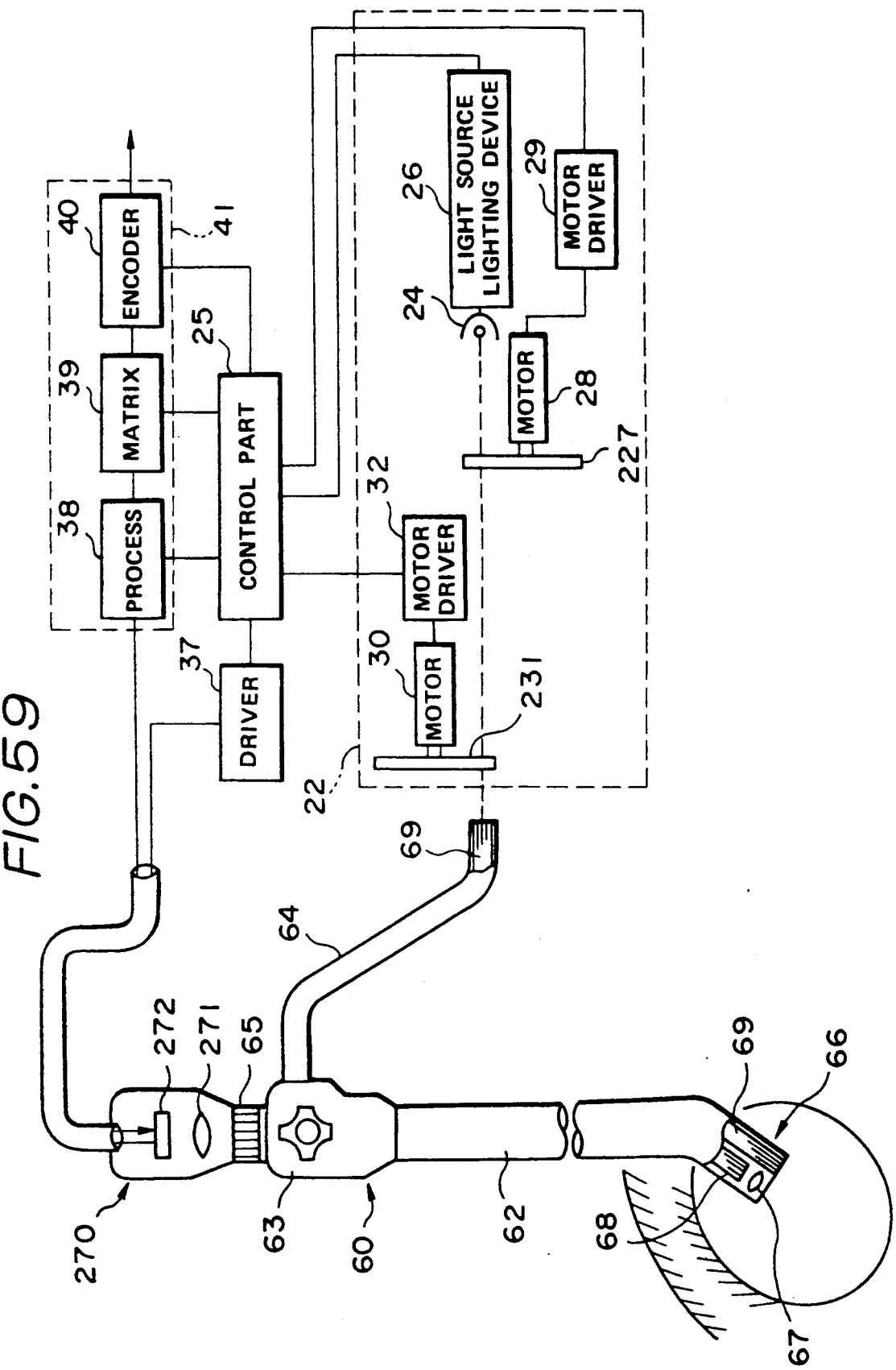
FIG. 59 is an explanatory view showing the formation of an endoscope apparatus relating to the seventeenth embodiment of the present invention.

The seventeenth embodiment of the present invention is shown in FIG. 59.

In this embodiment, the imaging apparatus of the twelfth embodiment is applied to an externally fitted television camera fitted to the eyepiece part of a fiberscope.

The fiberscope 60 is of the same formation as is shown in the fifth and eleventh embodiments and its explanation shall be omitted.

An externally fitted television camera 270 is to be removably fitted to the eyepiece part 65 of the above mentioned fiberscope 60. This externally fitted television camera 270 is provided with an image forming lens 271 forming an image of the light from the above mentioned eyepiece part 65 and a solid state imaging device arranged in the image forming position of this image forming lens 271. The light emitted from the light source 24 is to enter the entrance end of the light guide 69 of the fiberscope 60 through the band limiting filter 117 and rotary filter 231.

The other formations, operations and effect are the same as in the twelfth embodiment.

In this embodiment, the combination of the rotary filter and band limiting filter is not limited to be such as is shown in the twelfth embodiment but may be such as is shown in the thirteenth to sixteenth embodiments.

In the above mentioned twelfth to seventeenth embodiments, there may be used a band limiting filter which can selectively transmit such three or more bands as the ultraviolet band, visible band and infrared band and respective filters of the color filter having a transmitting characteristic in three or more ranges selectable by the above mentioned band limiting filter so that any observing wavelength band may be selected from among three or more observing wavelength bands.

The selectable observing wavelength band is not limited to be divided into ultraviolet, visible and infrared bands but may be set so that, for example, a part of the long wavelength side of the visible range and the short wavelength side of the infrared range may be made an observing wavelength band.

The band limiting filter and rotary filter 37 may be arranged between the light source 24 and an imaging means such as the solid state imaging device 36 and the arranging order can be optionally determined.

Not only the light reflected by the observed object but also the light transmitted through the observed object may be received.

The eighteenth embodiment of the present invention is shown in FIGS. 60 to 65.

Figure 60:
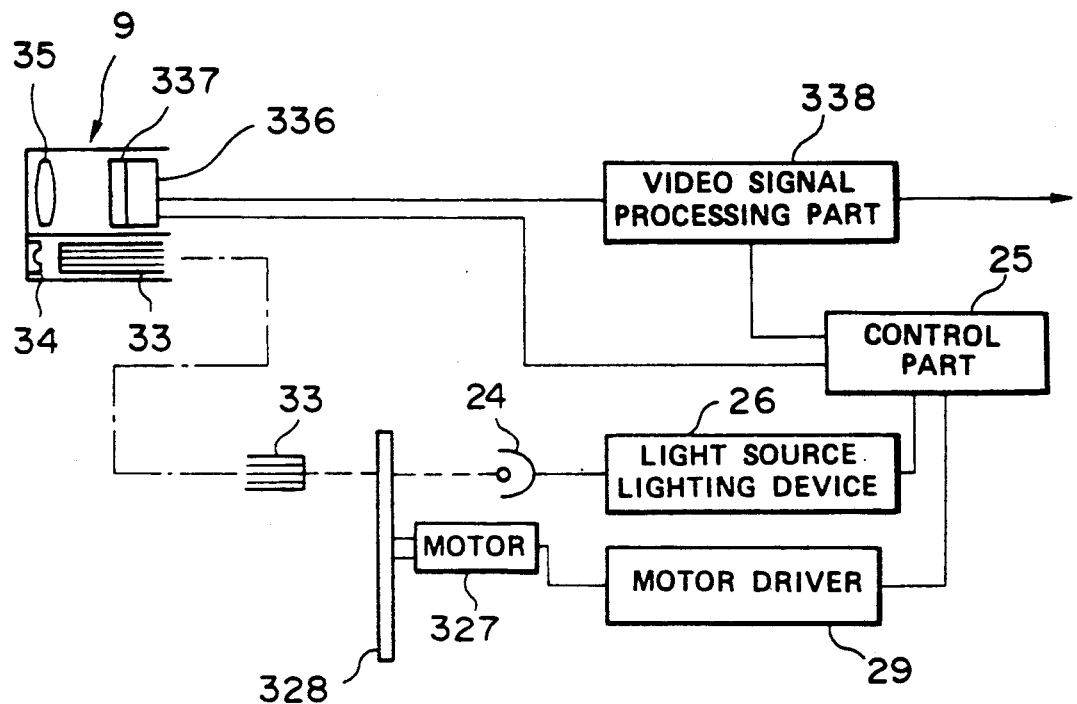
FIGS. 60 to 65 relate to the eighteenth embodiment of the present invention.

The imaging apparatus of this embodiment is formed as shown in FIG. 60.

Figure 61:
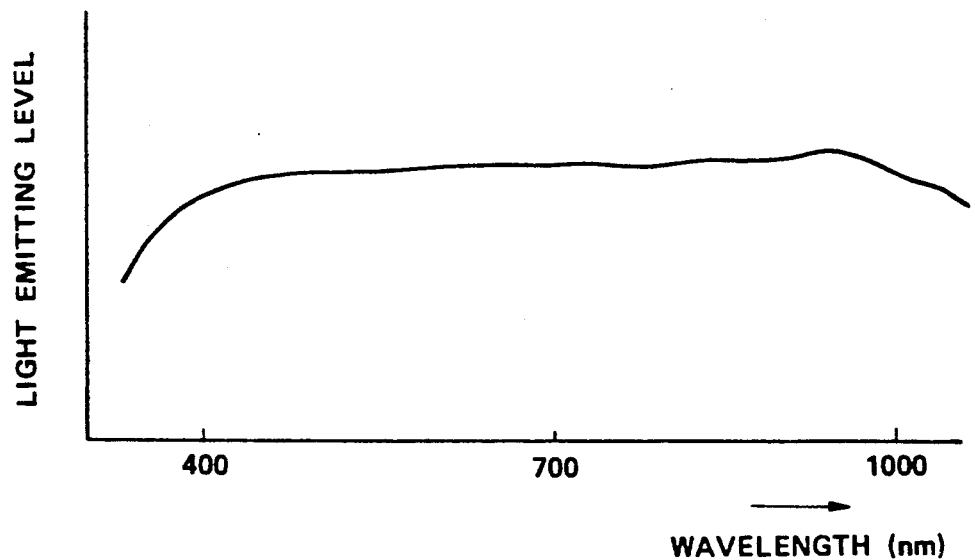
Figure 62:
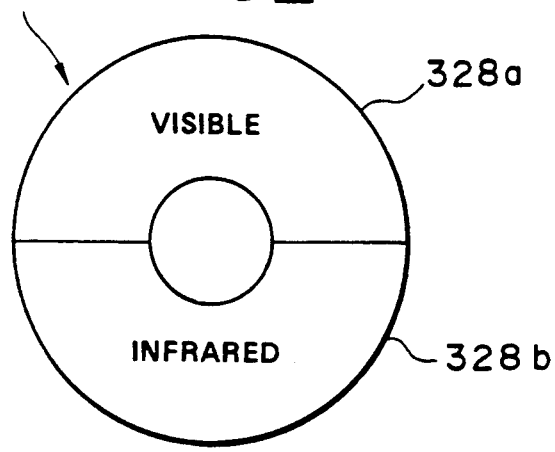
Figure 63:
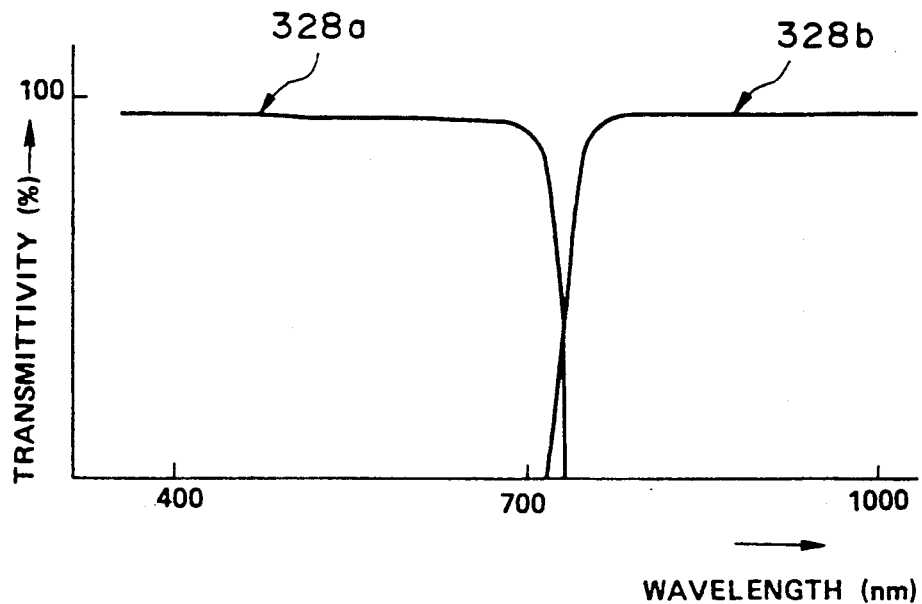

A light source 24 is provided within the control apparatus 6. As shown in FIG. 61, this light source 24 is to emit a light of a wavelength in a wide band at least ranging from the visible range to the infrared range and can be a general halogen lamp, xenone lamp or the like. This light source 24 is controlled to be lighted by a light source lighting apparatus 26 controlled by the control part 25. A band limiting filter 328 as a band limiting means rotated and driven by a driving motor 327 is arranged in front of the above mentioned light source 24 and is divided into two parts in the peripheral direction as shown in FIG. 62. A filter 328a transmitting the visible band and a filter 328b transmitting the infrared band are arranged in the divided respective parts as shown in FIG. 63. Therefore, of the light emitted from the above mentioned light source 24, either of the visible band and infrared band is selectively transmitted by this band limiting filter 328. The above mentioned driving motor 327 is controlled to rotate by the motor driver 29 controlled by the control part 25.

The light transmitted through the above mentioned band limiting filter 328 enters the light guide 33 inserted through the above mentioned cable 4 and insertable part 2, is led to the tip part 9 through this light guide 33 and is emitted from the light distributing lens 34 provided in this tip part 9 to illuminate the observed object.

Figure 64:
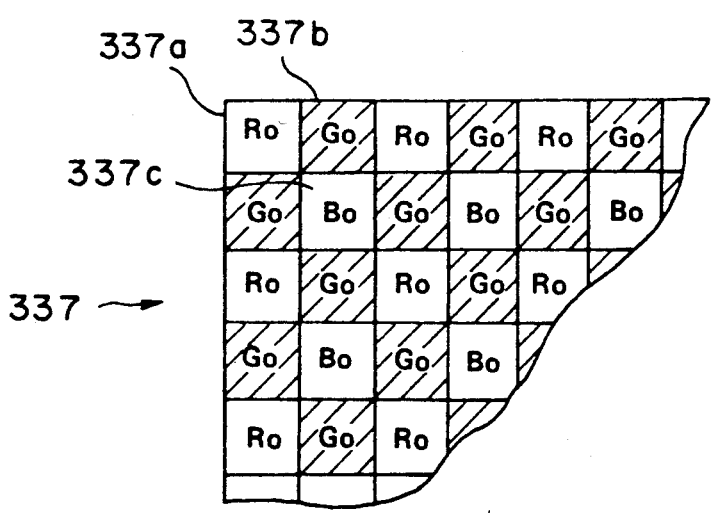

On the other hand, a solid state imaging device 336 as an imaging means is arranged in the image forming position of the objective lens system 35 provided in the tip part. This solid state imaging device 336 has a sensitivity at least to the visible band and infrared band. A color filter 337 as a wavelength range dividing means is arranged in front of the imaging surface of the above mentioned solid state imaging device 336. In this color filter 337, as shown in FIG. 64, filters 337a, 337b and 337c transmitting respectively different wavelength ranges are arranged, for example, to be mosaic-like.

Figure 65:
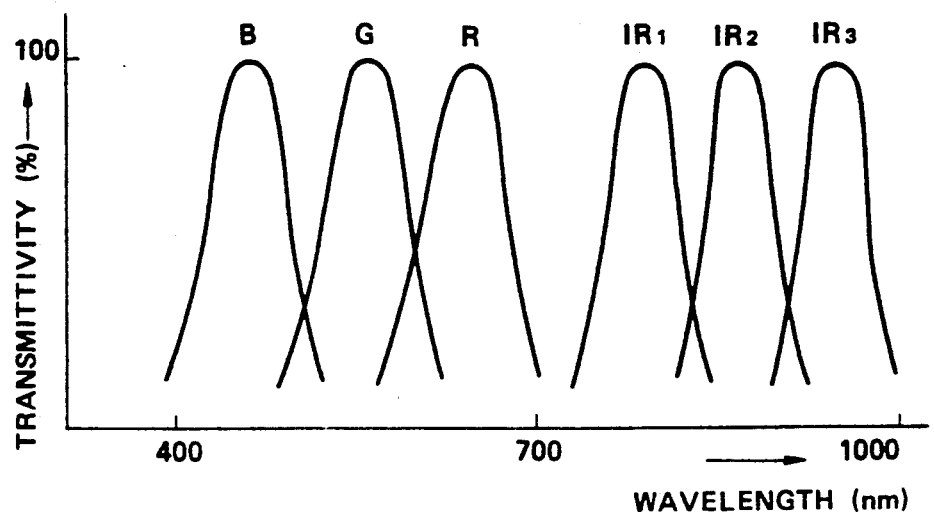

In this embodiment, the above mentioned respective filters 337a, 337b and 337c have a double transmitting characteristic and have transmitted wavelength ranges in the visible band and infrared band. That is to say, as shown in FIG. 65, the filter 337a transmits the red light R in the visible band and infrared light IR3 in the infrared band, the filter 337b transmits the green light G in the visible band and infrared light IR2 in the infrared band and the filter 337c transmits the blue light B in the visible band and infrared light IR1 in the infrared band. The above mentioned infrared lights IR1, IR2 and IR3 are respectively different in the wavelength range and the center wavelengths are longer in the order of IR1, IR2 and IR3.

In this embodiment, the transmitted wavelength ranges of the respective filters 337a, 337b and 337c of the above mentioned color filter 337 are limited to the wavelength ranges belonging to either of the visible band and infrared band by the above mentioned band limiting filter 328. That is to say, when the visible band is selected by the above mentioned band limiting filter 328, the infrared band will not be illuminated and therefore the respective filters 337a, 337b and 337c of the above mentioned color filter 337 will transmit respectively B, G and R of the visible band. On the other hand, when the infrared band is selected by the above mentioned band limiting filter 328, the visible band will not be illuminated and therefore the respective filters 337a, 337b and 337c of the above mentioned color filter 337 will transmit respectively IR1, IR2 and IR3 in the infrared band. The light transmitted through the above mentioned respective filters 337a, 337b and 337c are received by the above mentioned solid state imaging device 336 and are photoelectrically converted. The signals corresponding to the respective picture elements of this solid state imaging device 336 are input into a video signal processing part 338 and are processed in response to a simultaneous system. In this video signal processing part 338, the signals corresponding to the respective picture elements of the above mentioned solid state imaging device 336 are processed to be video signals by the type of the filters 337a, 337b and 337c in front of the respective picture elements. For example, red(R) is alloted to the picture element signal corresponding to the filter 337a, green(G) is alloted to the picture element signal corresponding to the filter 337b and blue(B) is alloted to the picture element signal corresponding to the filter 337c and the signals are processed to be video signals. The video signals output from this video signal processing part 338 are input into the above mentioned color CRT monitor 7 and the observed object is color-displayed.

In this embodiment formed as in the above, when the light source lighting device 26 is operated to be lit by the control part 25, a light including a visible light and infrared light will be emitted from the light source 24. Of the light emitted from this light source 24, only the visible band or infrared band is selectively transmitted by the band limiting filter 228. The light having passed through this band limiting filter 228 is radiated onto the observed object.

The reflected light of the observed object corresponding to this illuminating light is received by the solid state imaging device 336 through the color filter 337 arranged in front of the solid state imaging device. The respective filters 337a, 337b and 337c of the above mentioned color filter 337 have a transmitted wavelength range in the visible band and infrared band so that, when the visible band is selected by the above mentioned band limiting filter 328, the respective filters 337a, 337b and 337c of the above mentioned color filter 337 will transmit respectively B, G and R of the visible band but, on the other hand, when the infrared band is selected by the above mentioned band limiting filter 328, the respective filters 337a, 337b and 337c of the above mentioned color filter 337 will transmit respectively IR1, IR2 and IR3 of the infrared band.

The light having entered the above mentioned solid state imaging device 336 is photoelectrically converted and is processed in the video signal processing part 338 to produce video signals and the observed object image is color-displayed by the color CRT monitor That is to say, when the visible band is selected by the band limiting filter 328, a general visible range image of the observed object will be displayed but, on the other hand, when the infrared band is selected by the band limiting filter 328, an infrared range image of the observed object will be displayed in quasi colors.

Thus, according to this embodiment, by switching the band limiting filter 328, the observing band of either of the visible range and infrared range is selected in response to the observed object which can be color-displayed. Therefore, an optimum observing wavelength range can be selected in response to the observed object. The color tone difference in the respective positions of the observed object difficult to discriminate in the picture image of the general visible range can be easily detected.

The respective filters 337a, 337b and 337c of the above mentioned color filter 337 are not limited to transmit respectively R, G and B in the visible band as shown in FIG. 64 but may transmit respectively yellow-(Ye), green(G) and cyanine(Cy) in the visible band.

Figure 66:
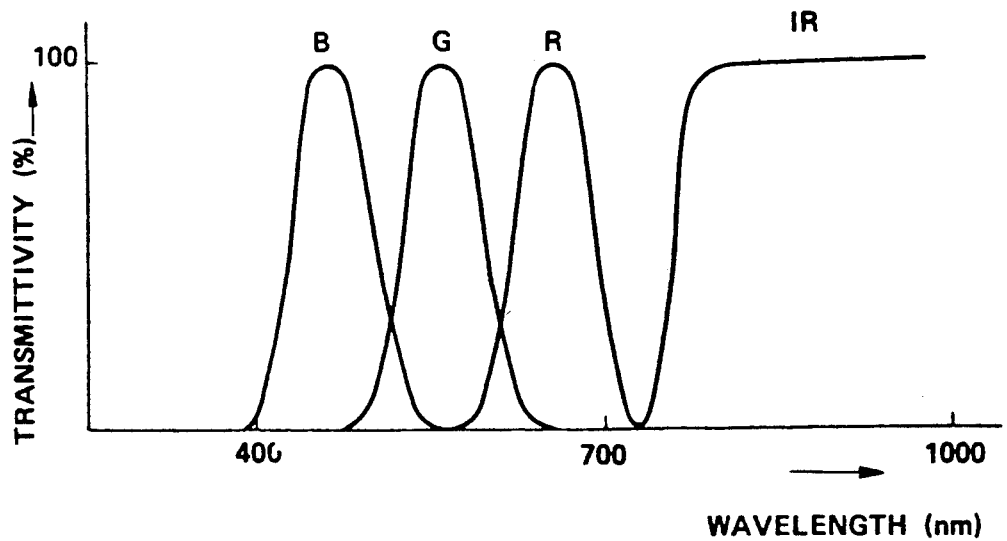
FIG. 66 is an explanatory diagram showing the transmitting characteristics of the respective filters of a color filter relating to the nineteenth embodiment of the present invention.

The nineteenth embodiment of the present invention is shown in FIG. 66.

The respective filters 337a, 337b and 337c of the color filter 337 in this embodiment are to transmit respectively the red light R and infrared band IR, the green light G and infrared band IR and the blue light B and infrared band IR as shown in FIG. 65.

In the video processing part 338, when the visible band is selected by the band limiting filter 328, the output signal of the solid state imaging device 336 will be processed as a color picture image to be a video signal but, on the other hand, when the infrared band is selected by the above mentioned band limiting filter 328, the output signal of the above mentioned solid state imaging device 336 will be processed as a monocolor picture image to be a video signal. The other formations are the same as in the eighth embodiment.

In this embodiment, by switching the band limiting filter 328, the color picture image in the visible band and monocolor picture image in the infrared band can be selectively displayed in response to the observed object.

In this embodiment, as compared with the color filter of the transmitting characteristic shown in FIG. 65, the respective filters 337a, 337b and 337c of the color filter 337 will be more easily formed and the lower cost can be realized.

The respective filters 337a, 337b and 337c of the above mentioned color filter 337 are not limited to transmit respectively R, G and B in the visible band as shown in FIG. 66 but may transmit yellow(Ye), green(G) and cyanine(Cy) in the visible band as shown, for example, in FIG. 45.

Figure 67:
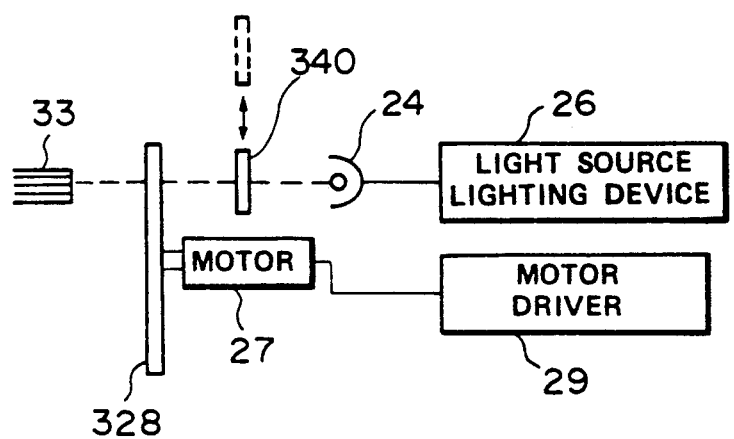
FIG. 67 is an explanatory diagram showing a light source part in the twentieth embodiment of the present invention.

The twentieth embodiment of the present invention is shown in FIG. 67.

In this embodiment, a band limiting filter 340 is provided insertably in the illuminating light path of the light source 24 in the nineteenth embodiment and has a band pass characteristic of a narrow band having 805 nm. in the center as shown in FIG. 49. It is preferable that the transmitted wavelength band Wo of this band limiting filter 240 is so narrow as to be less than about 40 nm.

The other formations are the same as in the nineteenth embodiment.

As shown in FIG. 50, the blood in which ICG is mixed has a maximum absorption at 805 nm. Therefore, when ICG is mixed in blood, for example, by venous injection, the infrared band is selected by the band limiting filter 328 and the above mentioned band limiting filter 340 having a band pass characteristic having a maximum absorption factor of 805 nm. in the center is interposed in the illuminating light path of the light source 24, the light of the narrow band having 805 nm. in the center will be radiated onto the observed body and the observed body image in this narrow band will be observed. The light having 805 nm. in the center will reach the deep part of the mucous membrane, absorption will be made in the vein part and therefore the vein part will be observed as a shadow. Therefore, as compared with the case of observing in other wavelength ranges, the vein running state can be observed in a much higher contrast.

The operation when the above mentioned band limiting filter 340 is retreated from the illuminating light path of the light source 24 is the same as in the eighteenth embodiment. The color filter 337 is not limited to be as shown in FIG. 66 but may have a transmitting characteristic shown, for example, in FIG. 45.

Figure 68:
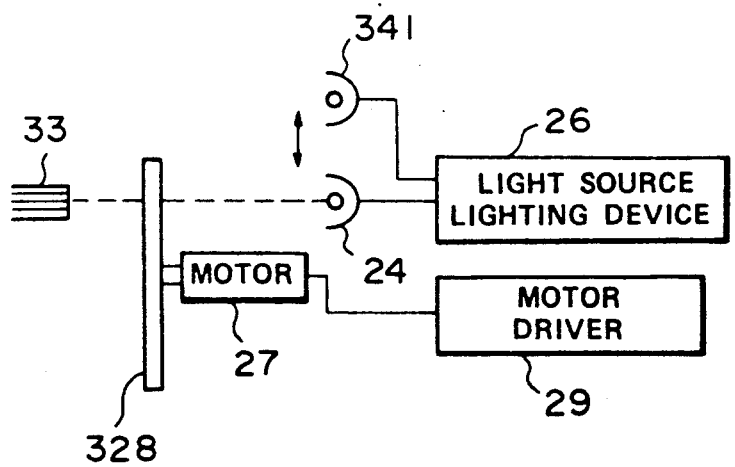
FIG. 68 is an explanatory diagram showing a light source part in a modification of the twentieth embodiment.

As shown in FIG. 68, a light source 341 such as a laser or LED emitting the light of a narrow band having 805 nm. in the center may be prepared instead of inserting the above mentioned band limiting filter 340 in the illuminating light path. When observing the observed object image in the narrow band having 805 nm. in the center, the above mentioned light source 341 may be used instead of the light source 24 emitting the light of a wide band.

Figure 69:
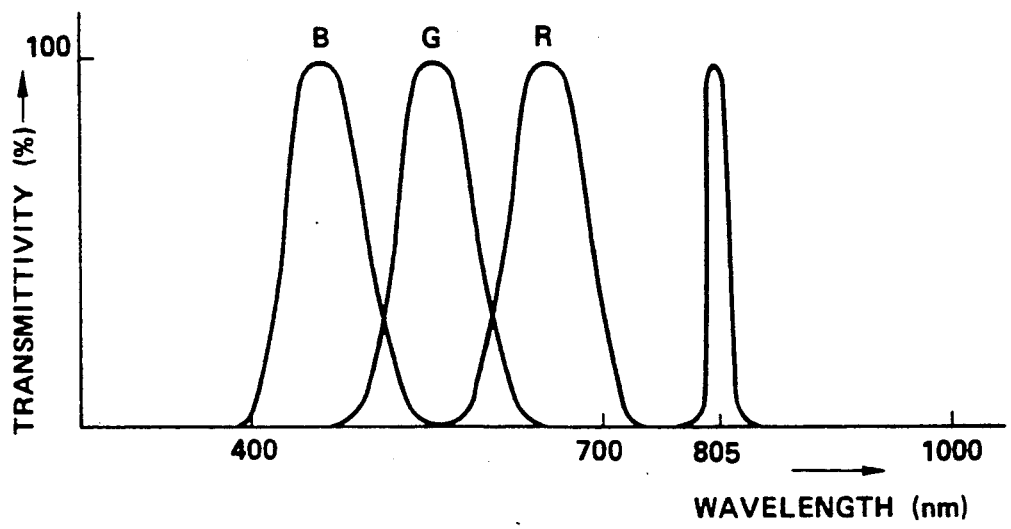
FIG. 69 is an explanatory diagram, showing the transmitting characteristic of a band limiting filter of a narrow band in the twenty-first embodiment of the present invention.

The twenty-first embodiment of the present invention is shown in FIG. 69.

In this embodiment, the transmitting characteristics of the respective filters 337a, 337b and 337c of the color filter 337 in the nineteenth embodiment are so made that, as shown in FIG. 69, the filter 337a transmits R in the visible band and the narrow band having 805 nm. in the center, the filter 337b transmits G in the visible band and the narrow band having 805 nm. in the center and the filter 337c transmits B in the visible band and the narrow band having 805 nm. in the center.

The other formations are the same as in the nineteenth embodiment.

In this embodiment, when the visible band is selected by the band limiting filter 328, a color picture image by an ordinary visible band will be obtained but, on the other hand, when the infrared band is selected by the above mentioned band limiting filter 328, the infrared light will be radiated onto the observed object, only the light of the narrow band having 805 nm. in the center will pass through the above mentioned color filter 337 and the observed object image in this narrow band will be observed.

The filters transmitting the narrow band having 805 nm. in the center need not be all of the filters 337a, 337b and 337c but, for example, one filter may have the above mentioned narrow band transmitting characteristic.

Figure 70:
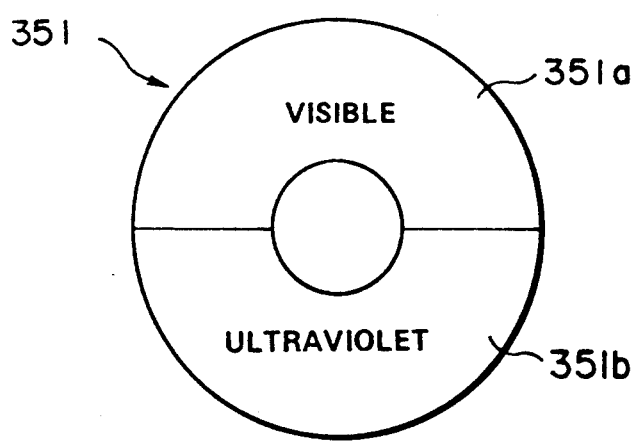
FIGS. 70 to 72 relate to the twenty-second embodiment of the present invention.
Figure 71:
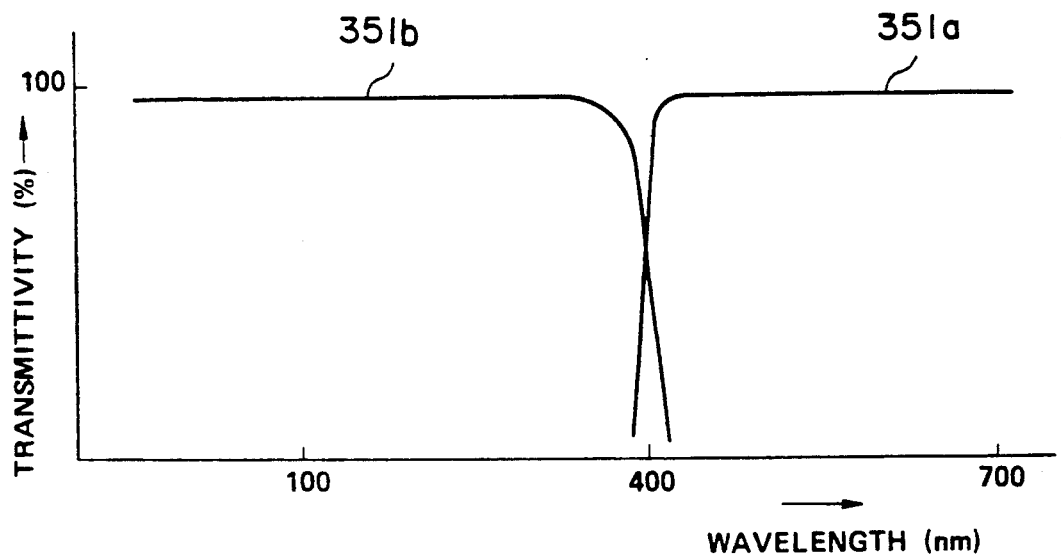
Figure 72:
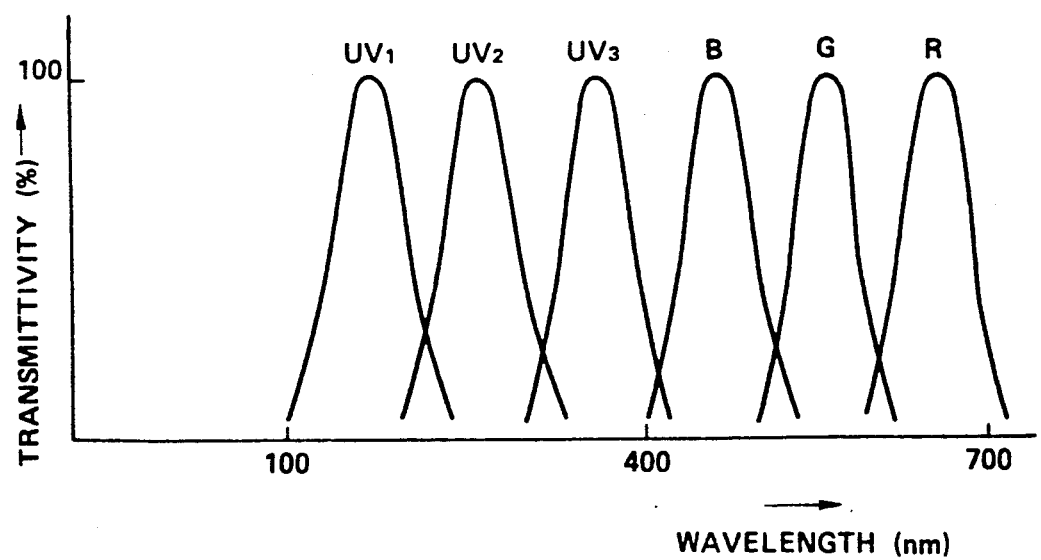

The twenty-second embodiment of the present invention is shown in FIGS. 70 to 72.

In this embodiment, a band limiting filter 351 as is shown in FIG. 70 is provided instead of the band limiting filter in the eighteenth embodiment.

The respective filters 351a and 351b of this band limiting filter 351 are filters transmitting respectively the visible band and ultraviolet band as shown in FIG. 71. The respective filters 337a, 337b and 337c of the color filter 337 have the transmitted wavelength range in the visible band and ultraviolet band as shown in FIG. 72. That is to say, the filter 337a transmits the red light R and the ultraviolet light UV3 in the ultraviolet band, the filter 337b transmits the green light G and the ultraviolet light UV2 in the ultraviolet band and the filter 337c transmits the blue light B and the ultraviolet light UV1. The above mentioned ultraviolet light UV2, UV2 and UV3 are respectively different in the wavelength range and are longer in the center wavelength in the order of UV1, UV2 and UV3.

In this embodiment, by switching the band limiting filter 351, either of the visible band and ultraviolet band is selected in response to the observed object which can be color-displayed. Therefore, the color tone difference in the respective positions of the observed object in the ultraviolet band which has not been able to be observed in the picture image of the general visible range can be observed.

Figure 73:
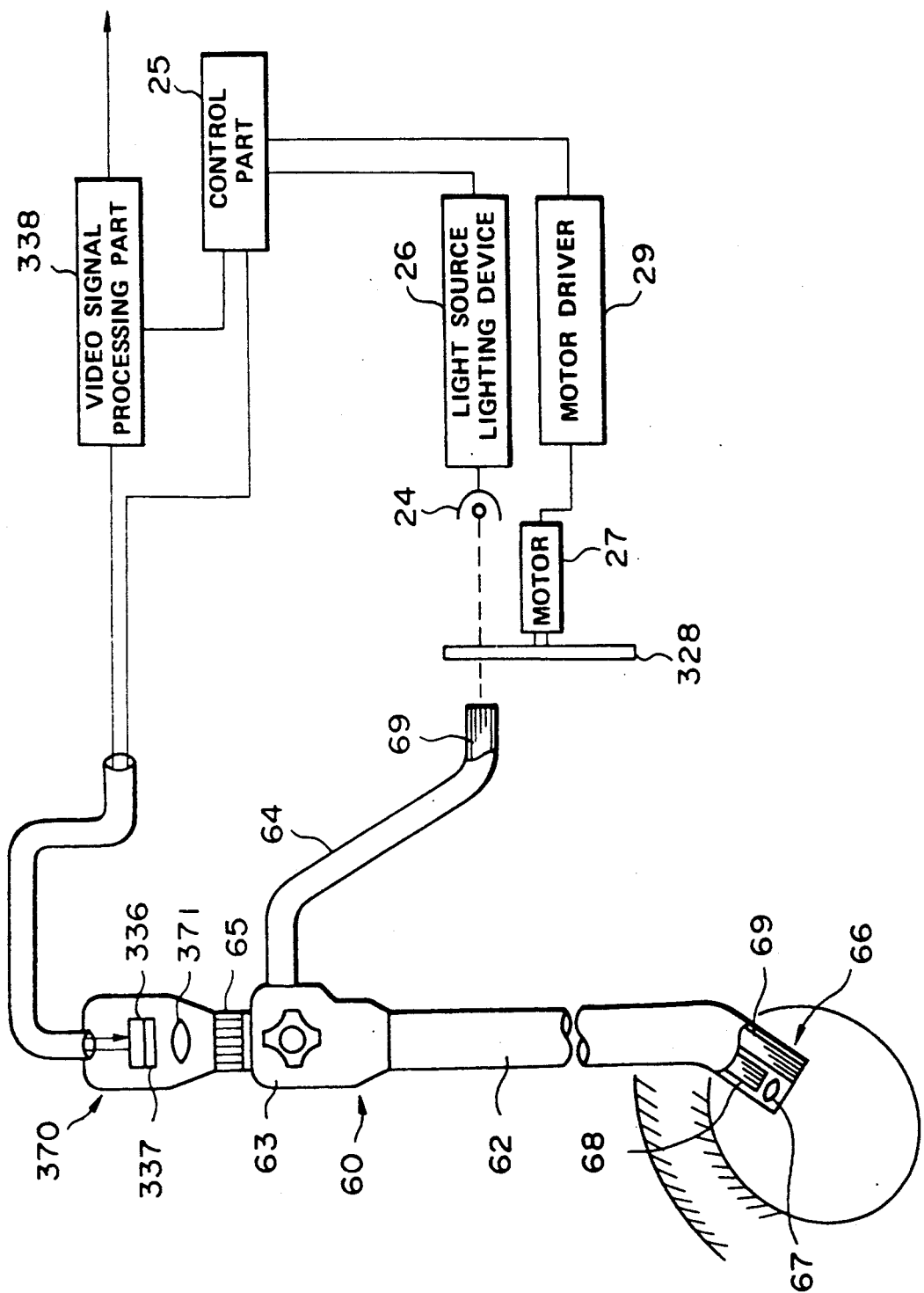
FIG. 73 is an explanatory diagram showing an endoscope apparatus relating to the twenty-third embodiment of the present invention.
Figure 74:
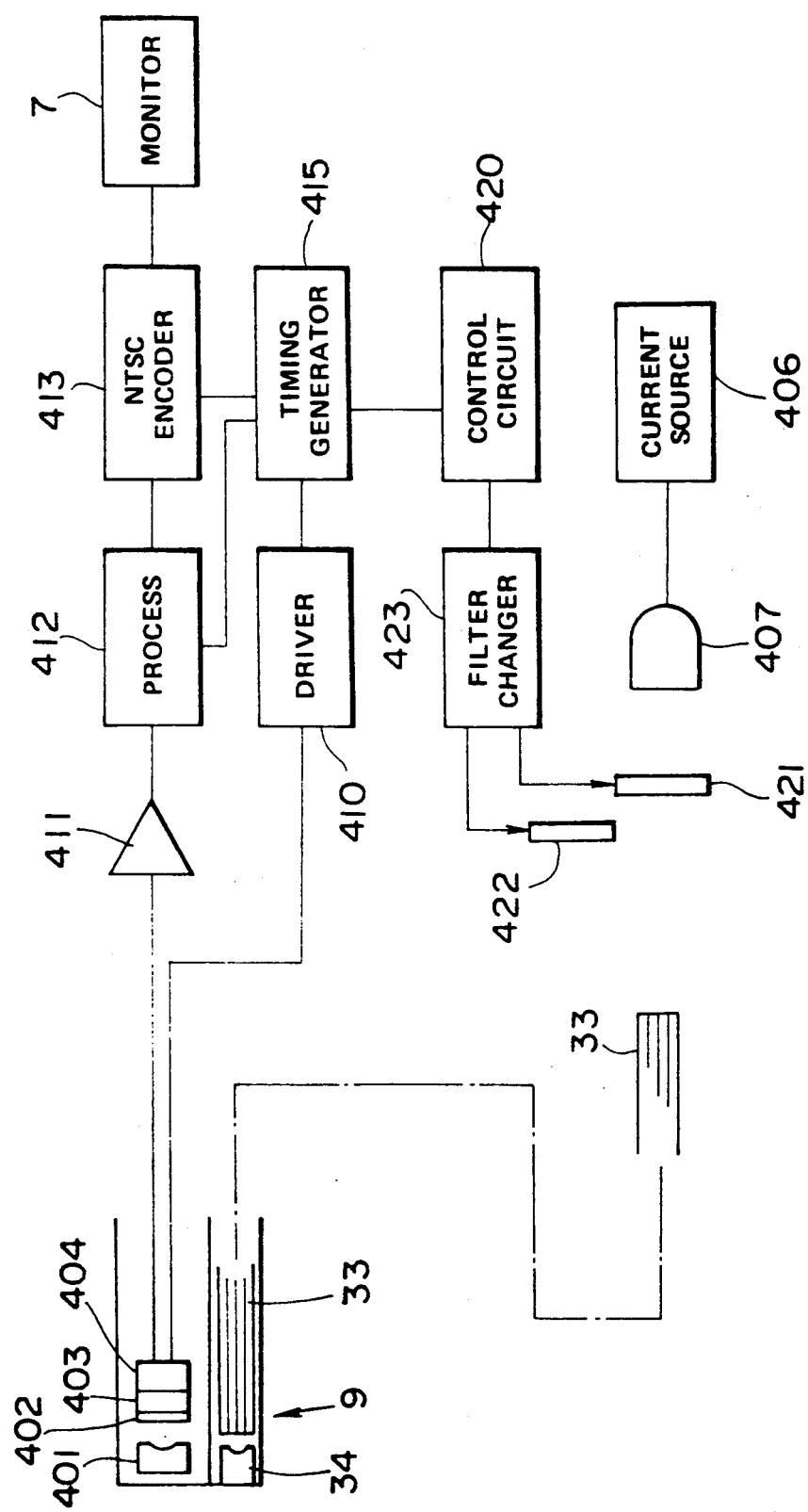
FIGS. 74 to 79 relate to the twenty-fourth embodiment of the present invention.

The twenty-third embodiment of the present invention is shown in FIG. 73.

In this embodiment, the imaging apparatus of the eighteenth embodiment is applied to an externally fitted television camera fitted to the eyepiece part of a fiberscope.

The fiberscope 60 is of the same formation as is shown in the fifth, eleventh and seventeenth embodiments and therefore its explanation shall be omitted.

An externally fitted television camera 370 is removably fitted to the eyepiece part 65 of the above mentioned fiberscope 60 and is provided with an image forming lens 371 forming an image of the light from the above mentioned eyepiece part 65 and a solid state imaging device 336 arranged in the image forming position of this image forming lens 371. The color filter 337 having a transmitting characteristic for the visible band and infrared band is provided in front of this solid state imaging device 336 the same as in the eighteenth embodiment. The light emitted from the light source 24 passes through the band limiting filter 328 transmitting selectively the visible band and infrared band and enters the entrance end of the light guide 69 of the fiberscope 60.

The other formations, operations and effects are the same as in the eighteenth embodiment.

In this embodiment, the combination of the color filter and band limiting filter is not limited to be as shown in the eighteenth embodiment but may be as shown in the eighteenth to twenty-third embodiments.

In the above mentioned eighteenth to twenty-third embodiments, the band limiting filter which can transmit selectively more than three as the ultraviolet band, visible band and infrared band may be used and the respective filters 337a, 337b and 337c of the color filter 337 having transmitted wavelength ranges in more than three bands which can be selected by the above mentioned band limiting filter may be used so that any observed wavelength band can be selected from among more than three observed wavelength bands.

The selectable observed wavelength band is not limited to be divided into the ultraviolet, visible and infrared bands but may be set to be, for example, a part of the long wavelength side of the visible range and the short wavelength side of the infrared range.

Further, the band limiting filter and color filter may be arranged between the light source 24 and an imaging means such as the solid state imaging device 336 and the arranging order can be optionally determined.

The twenty-fourth embodiment of the present invention is shown in FIGS. 74 to 79.

Figure 78:
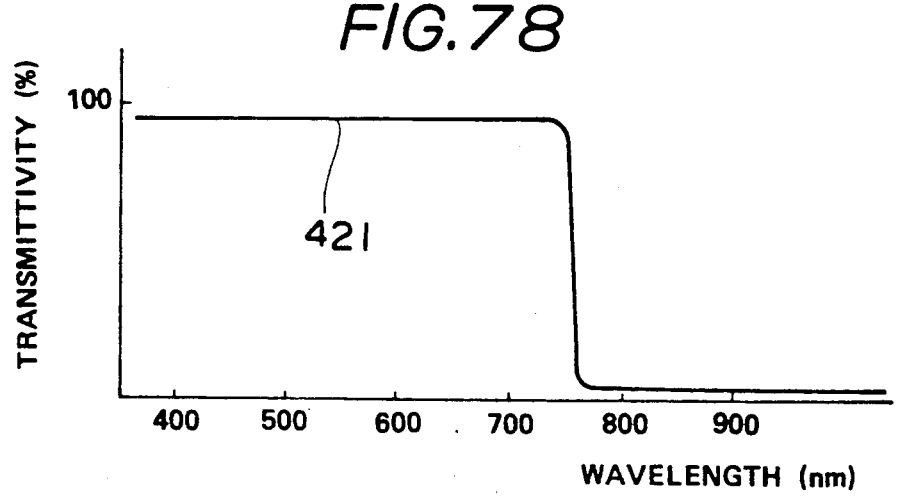
Figure 79:
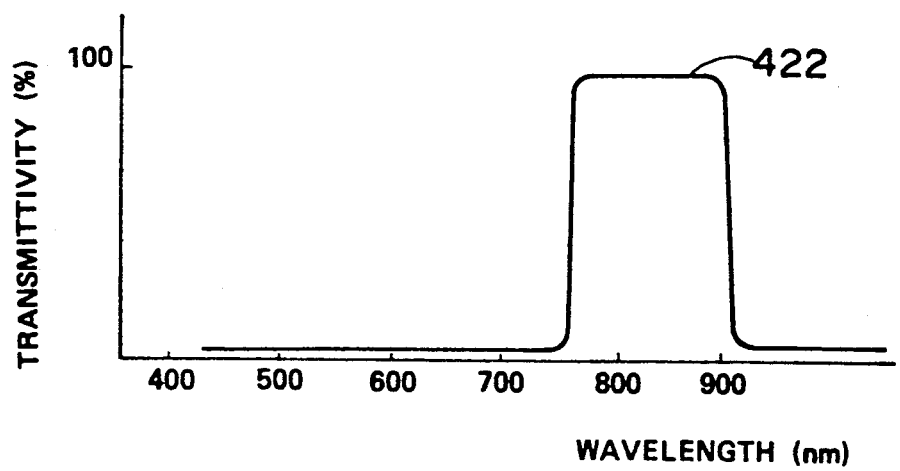

In this embodiment, a lamp 407 fed with an electric power by a current source 406 is provided within the control apparatus 6. This lamp 407 is to emit a light of a wavelength in a wide band ranging from a visible range to an infrared range. A visible light transmitting filter 421 and near infrared band pass filter 422 respectively individually insertable in an illuminating light path by a filter changer 423 are provided between the above mentioned lamp 407 and the entrance end of the light guide of the electronic endoscope 1. The above mentioned visible light transmitting filter 421 has a transmitting characteristic of transmitting a visible light range as shown in FIG. 78 and the above mentioned near infrared band pass filter 422 has a transmitting characteristic of transmitting only a near infrared light as shown in FIG. 79. The above mentioned filter changer 423 is controlled by a control circuit 420.

Figure 75:
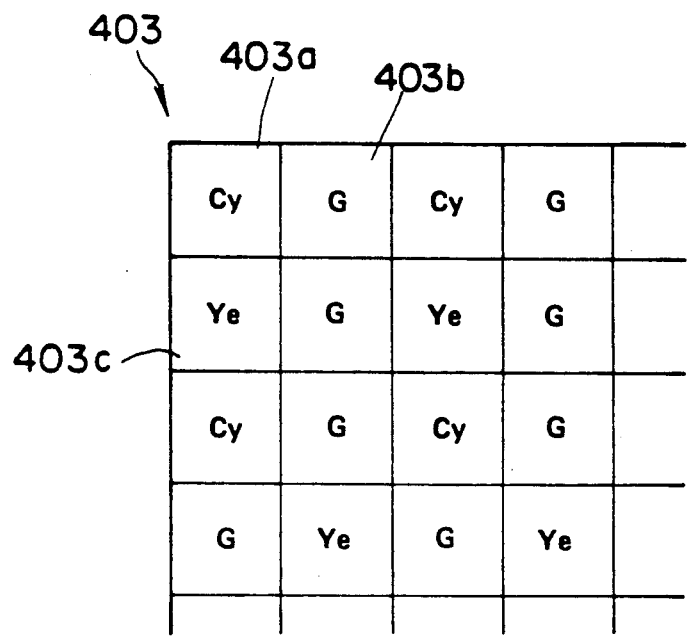
Figure 76:
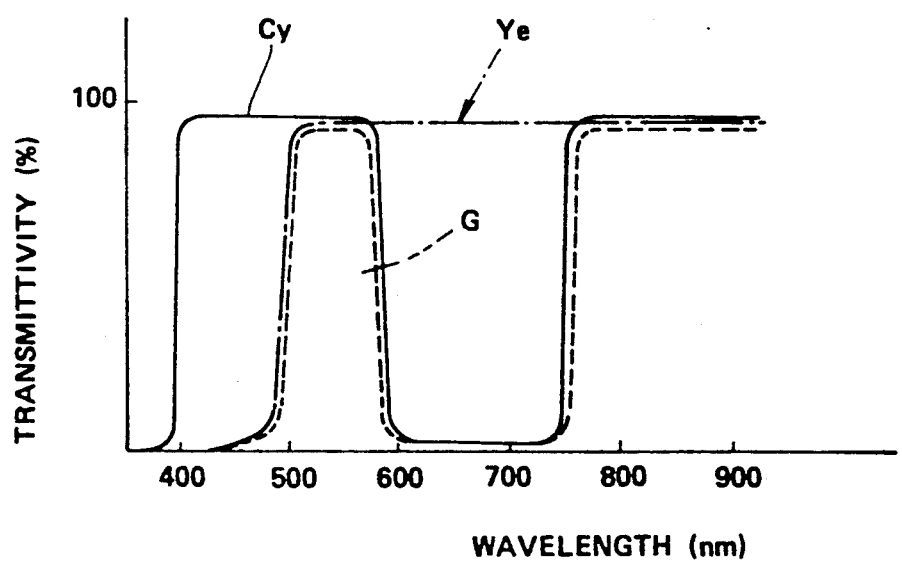

On the other hand, an objective lens system 401 is provided in the tip part 9 of the electronic endoscope 1. A solid state imaging device 404 is arranged in the image forming position of this objective lens system. This solid state imaging device 404 has a sensitivity at least to a visible to near infrared light range. A color separating filter 403 is provided on the front surface of the above mentioned solid state imaging device 404. As shown in FIG. 75, this color separating filter 403 is formed by arranging in a mosaic form respective color filters 403a, 403b and 403c transmitting respectively cyanine(Cy), green(G) and yellow(Ye) in the visible band. The respective filters 403a, 403b and 403c of the above mentioned color separating filter 403 have a double transmitting characteristic of transmitting not only Cy, G and Ye in the visible band but also an infrared light as shown in FIG. 76.

Figure 77:
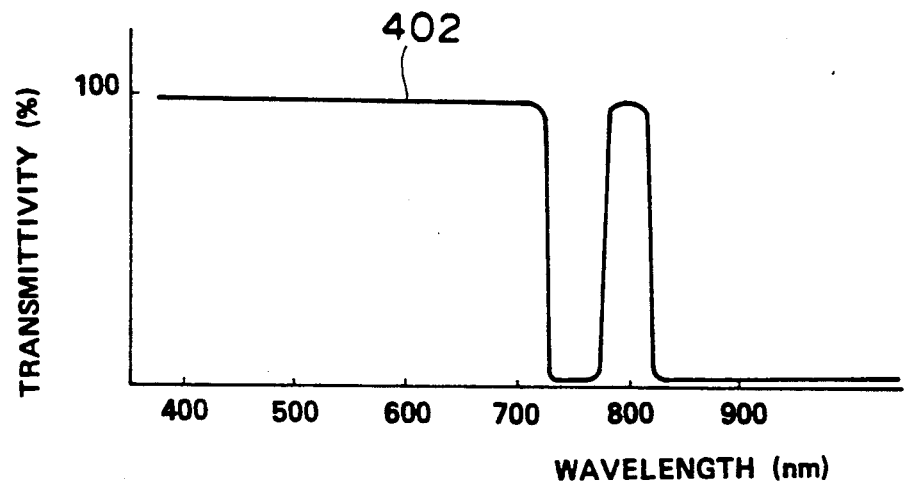

A filter 402 having a characteristic of transmitting a visible band and a narrow band having 805 nm. in the center as shown in FIG. 77 is provided between the above mentioned lens system 401 and solid state imaging device 404.

The above mentioned solid state imaging device 404 is driven by a driver 410 within the control apparatus and the signal read out is amplified by a pre-amplifier 411, is then input into a process circuit 412 and is processed to be $\gamma$-corrected, white-balanced and matrix-processed. The video signal from this process circuit 412 is input into an NTSC encoder 413, is converted to a video signal of an NTSC system and is input into the monitor 7.

The above mentioned control circuit 420, driver 410, process circuit 412 and NTSC encoder 413 are synchronized by a timing generator 414 generating the synchronized signal of the entire system.

In this embodiment, a light in a visible to infrared light range is emitted from the lamp 407 by an electric power from the current source 406, is transmitted to the tip part 9 of the electronic endoscope 1 through the light guide 33 and is radiated onto an object to be imaged. The returning light from the object by this illuminating light is made to form an image on the solid state imaging device 404 by the objective lens system and the object is imaged by this solid state imaging device 404.

Here, if only the visible light transmitting filter 421 is interposed in the illuminating light path by driving the filter changer 423 with the control by the control circuit 420, the light emitted from the above mentioned lamp 407 will pass through this visible light transmitting filter 421 to be made a visible light which will be radiated onto the object to be imaged. The returning light from the object by this illuminating light passes through the filter 402, is separated into colors by the color separating filter 403 and is then read out as a video signal by the solid state imaging device 404. The output signal of this solid state imaging device 404 is processed by the preamplifier 411, process circuit 412 and NTSC encoder 413 and a visible picture image is color-displayed in the monitor 7.

On the other hand, if only the near infrared band pass filter 422 is interposed in the illuminating light path by driving the filter changer 423 with the control by the above mentioned control circuit, the light emitted from the above mentioned lamp 407 will pass through this near infrared band pass filter 422 to be made a near infrared light which will be radiated onto the object to be imaged. The returning light from the object by this illuminating light enters the filter 402 and only the light in a narrow band having 805 nm. in the center passes through this filter 402. The light of this narrow band passes through the color separating filter 403 without being separated into colors by this separating filter and is read out as a video signal by the solid state imaging device 404. The output signal of this solid state imaging device 404 is processed by the pre-amplifier 11, process circuit 412 and NTSC encoder 413. The object image in the narrow band having 805 nm. in the center is displayed as a monocolor image in the monitor.

Thus, according to this embodiment, the same as in the other embodiments, not only an ordinary visible color picture image is obtained but also an infrared picture image in a narrow band having 805 nm. in the center can be obtained. Therefore, the same as in the ninth and sixteenth embodiments, by observing the infrared picture image in the narrow band having 805 nm. in the center by mixing ICG into blood, the veins running below the mucous membrane and the range of a disease in the deep part of the membrane which have been difficult or impossible to observe can be observed. Further, in the case of processing with a YAG laser, there is also an effect that, when the filter 402 having a transmitting characteristic of transmitting only the near infrared light having 805 nm. in the center in the infrared light range is provided in front of the solid state imaging device 404, the observed picture plane will not be disturbed by the light of 1060 nm. of the YAG laser.

Figure 80:
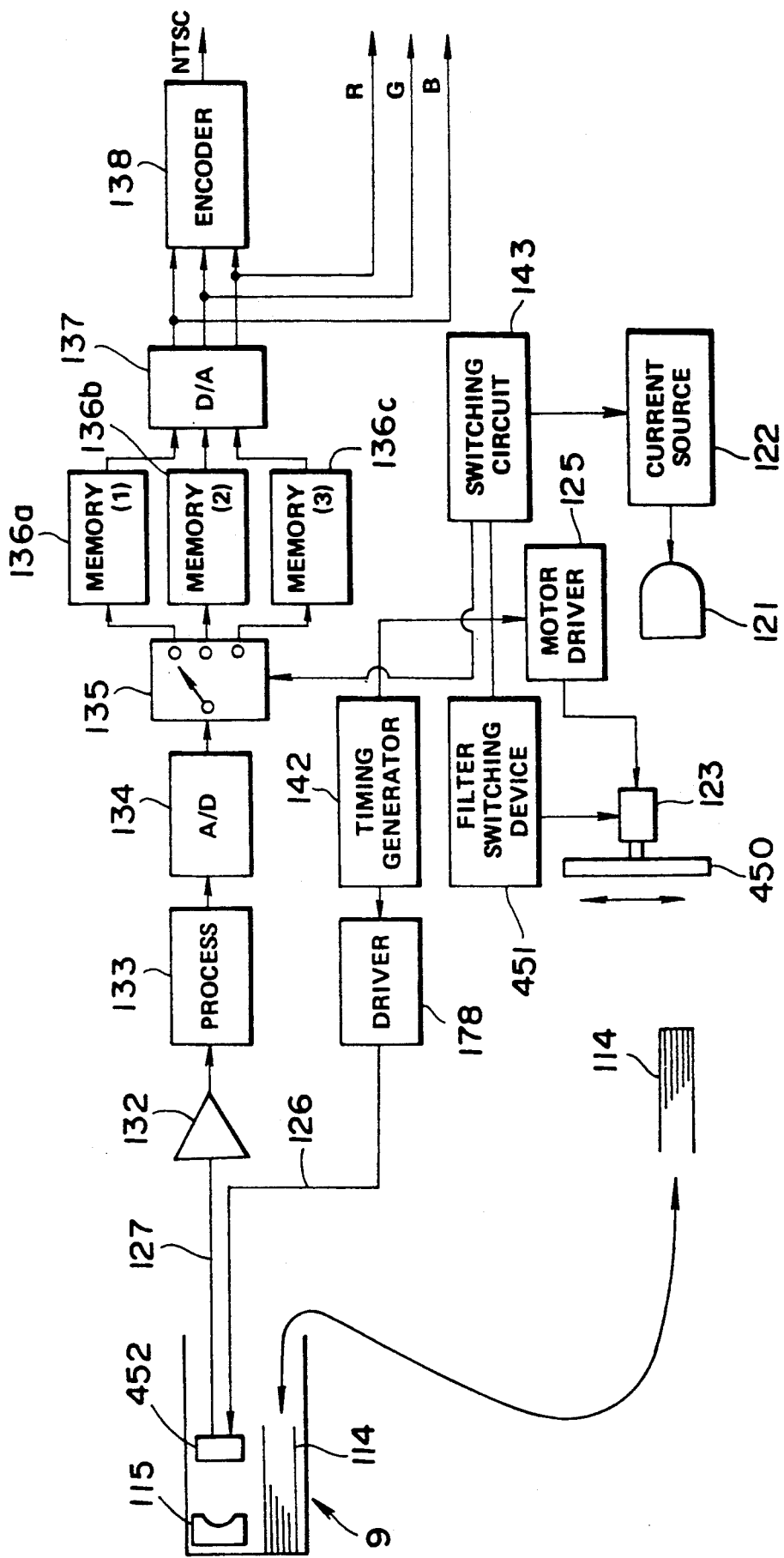
FIGS. 80 to 82 relate to the twenty-fifth embodiment of the present invention.
Figure 81:
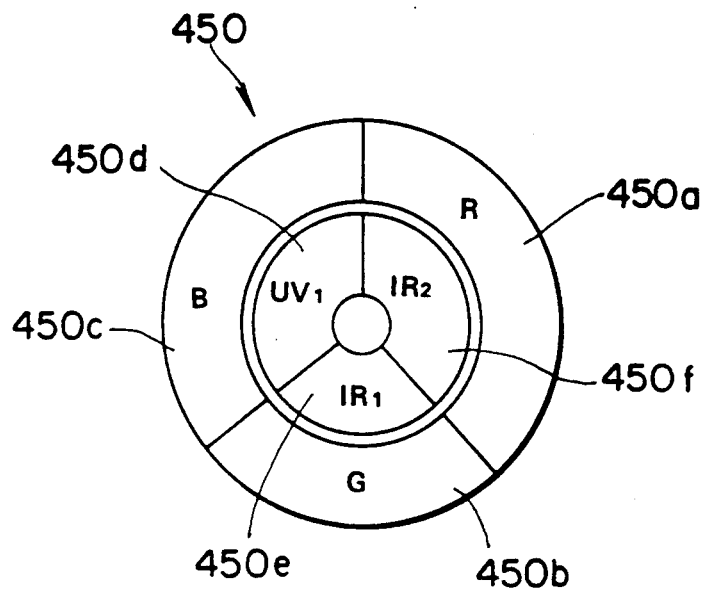
Figure 82:
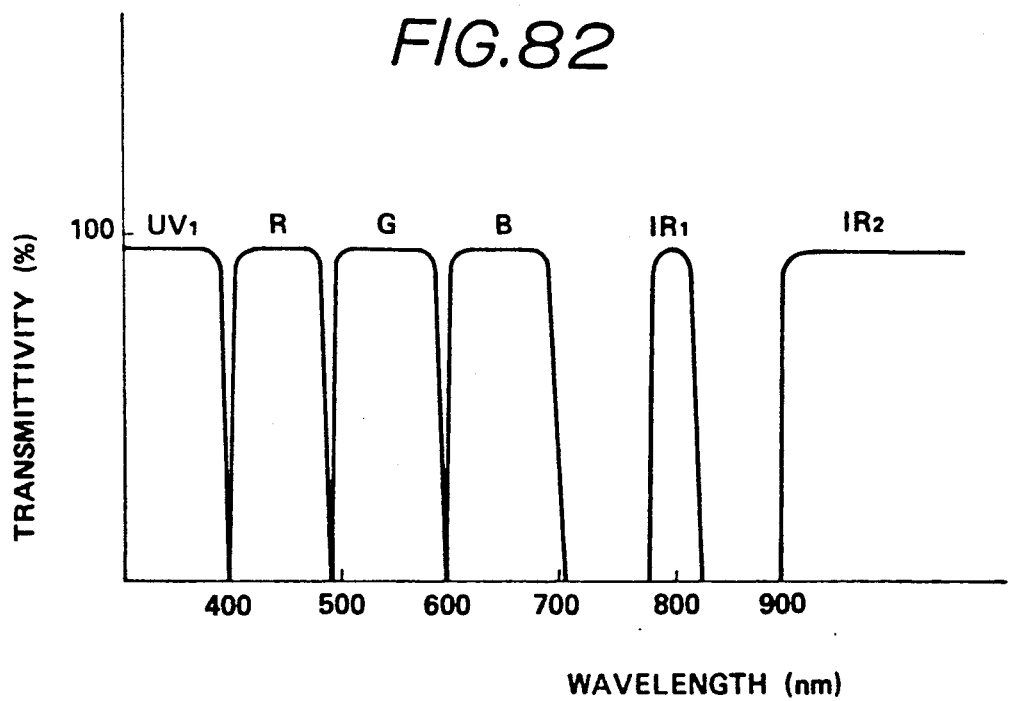

The twenty-fifth embodiment of the present invention is shown in FIGS. 80 to 82.

Figure 35:
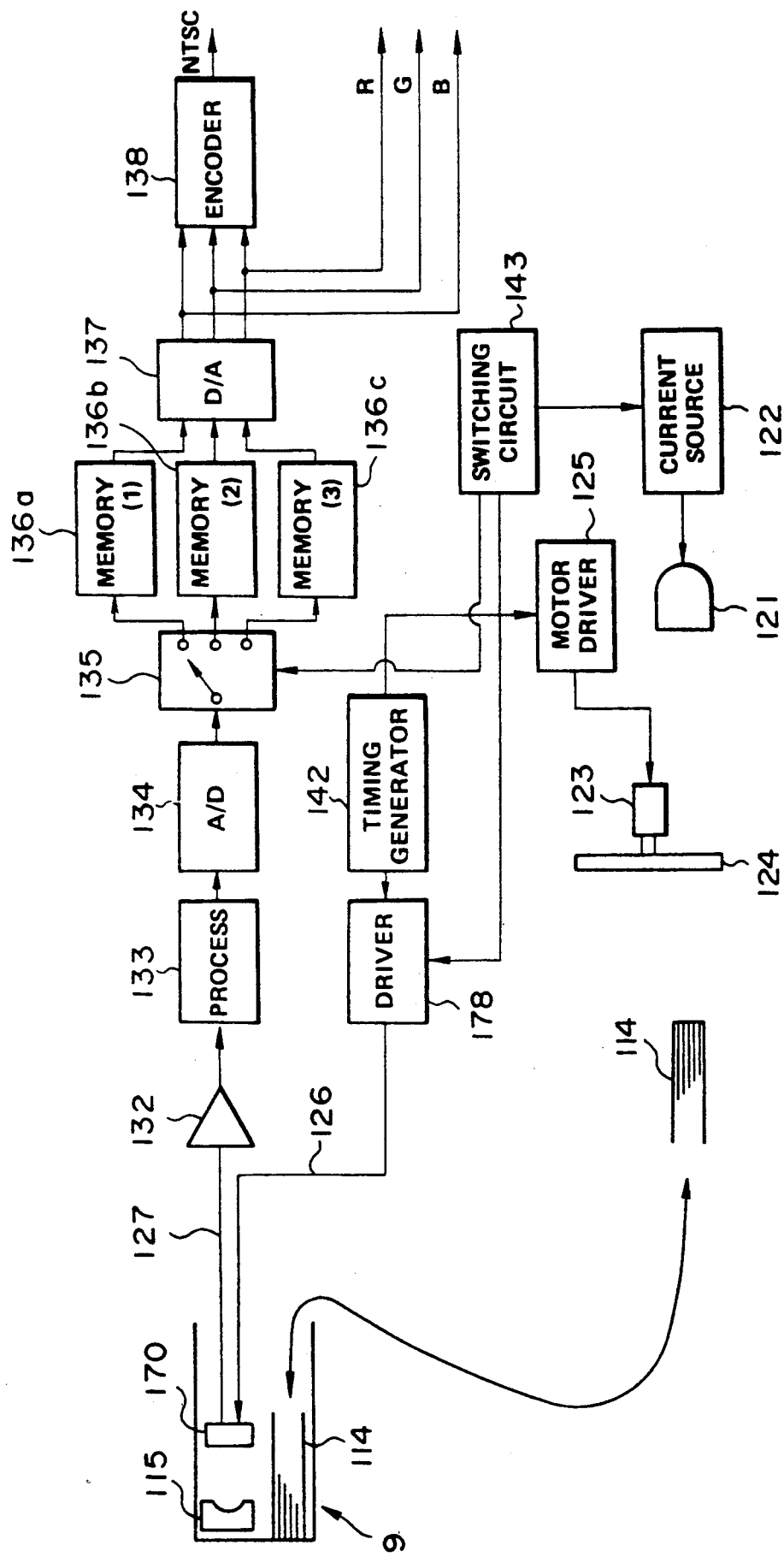
Figure 40:
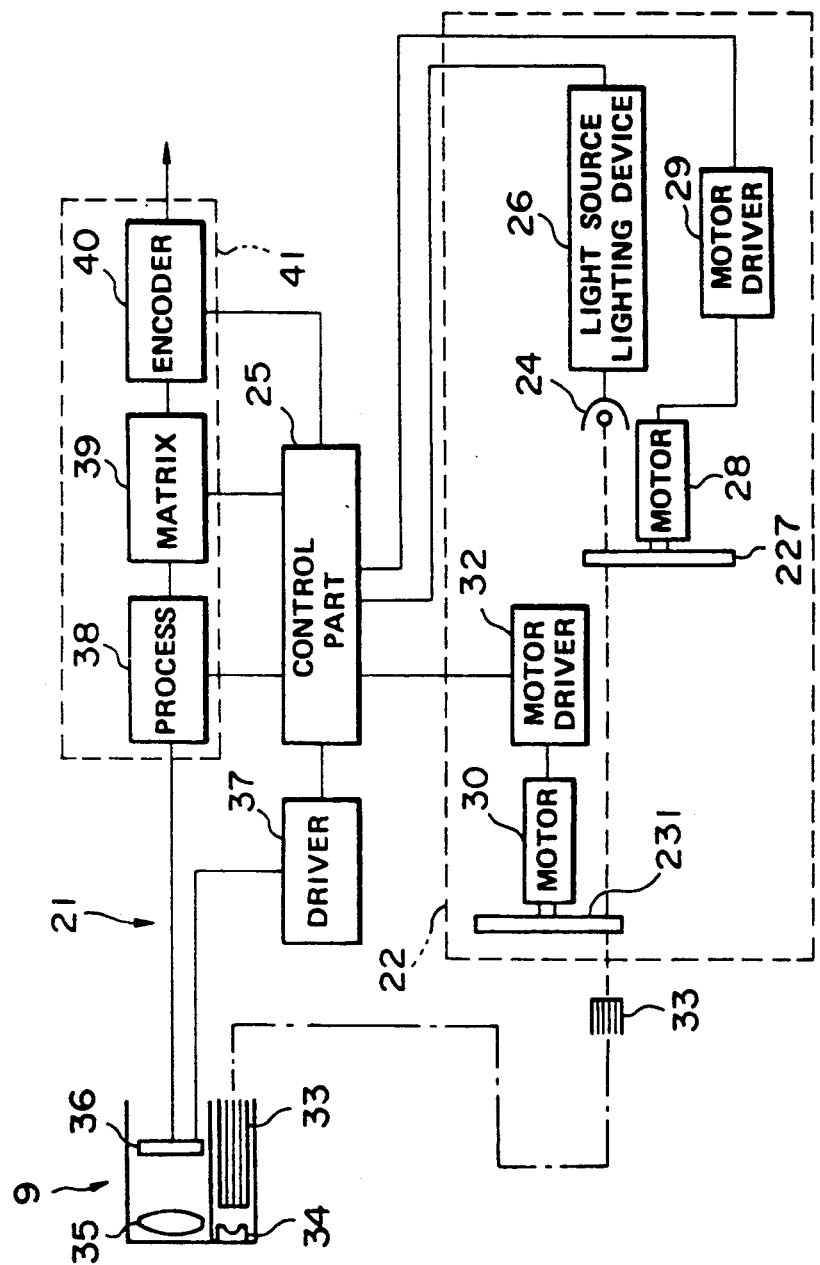
FIGS. 40 to 44 relate to the twelfth embodiment of the present invention.

The imaging apparatus of this embodiment is of substantially the same formation as of the eighth embodiment shown in FIG. 26 and the tenth embodiment shown in FIG. 35 but shutters such as the liquid crystal shutter 117 and electronic shutter are not provided.

As shown in FIG. 80, the objective lens system 115 is provided in the tip part of the electronic endoscope 1 and a solid state imaging device 452 is arranged in the image forming position of this objective lens system 115. This solid state imaging device 452 has a sensitivity to a wide wavelength range from an ultraviolet range to an infrared range and including a visible range. Signal lines 126 and 127 are connected to the above mentioned solid state imaging device 452, are inserted through the above mentioned insertable part 2 and universal cord and are connected to the connector 5.

On the other hand, a lamp 121 emitting a light in a wide band from an ultraviolet light to an infrared light is provided within the control apparatus. A rotary filter 450 rotated and driven by a motor 123 is arranged in front of the above mentioned lamp 121. In this rotary filter 450, as shown in FIG. 81, filters 450a, 450b and 450c transmitting respectively R, G and B are arranged in the peripheral direction on the outer peripheral side and a filter 450d transmitting an ultraviolet range UV1, a filter 450e having a band pass characteristic of a narrow band IR1 having 805 nm. in the center and a filter 450f transmitting an infrared light IR2 of more than 900 nm. are arranged in the peripheral direction on the inner peripheral side. The transmitting characteristics of the above mentioned respective filters 450a to 450f are shown in FIG. 82.

In this embodiment, a filter switching device 451 is provided and is made to move the above mentioned rotary filter 450 and motor 123 so that either of the outer peripheral side and inner peripheral side of the above mentioned rotary filter 450 may be interposed in the illuminating light path between the lamp 121 and the entrance end of the light guide 114.

The light having passed through the above mentioned rotary filter 450 enters the entrance end of the above mentioned light guide 114, is led to the tip part 9 through the light guide 114 and is emitted from this tip part 9 to illuminate the observed position.

The returning light from the observed position by this illuminating light is made to form an image on the solid state imaging device 452 by the objective lens system 115 and is photoelectrically converted. A driving pulse from the driver circuit 178 within the above mentioned control apparatus 6 is applied to the solid state imaging device 452 through the above mentioned signal line 126 and the signal is read out and transferred by this driving pulse. The video signal read out of this solid state imaging device 452 is input through the above mentioned signal line 127 into the pre-amplifier 132 provided within the above mentioned control apparatus or within the electronic endoscope 1. The video signal amplified by this preamplifier 132 is processed by the process circuit 133, A/D converter 234, selecting circuit 135, three memories (1) 136a, (2) 136b and (3) 136c, D/A converter 137 and converter 138 the same as in the eighth and tenth embodiments.

The other formations are the same as in the eighth or tenth embodiment.

In this embodiment, when the filter switching device 451 is controlled by the switching circuit 143 to interpose the outer peripheral side of the rotary filter 450 into the illuminating light path between the lamp 121 and the entrance end of the light guide 114, the light emitted from the above mentioned lamp 121 will pass in turn through the filters 450a, 450b and 450c transmitting respectively R, G and B of the above mentioned rotary filter 450 and will be divided in time series into the light of the respective wavelength range of R, G and B. This light of R, G and B is transmitted to the tip part 9 through the light guide 114 and is radiated onto the object to be imaged. The returning light from the object by the illuminating light in the field order of R, G and B in this visible range is made to form an image on the solid state imaging device 452 by the objective lens system 115 and the object is imaged by this solid state imaging device 452. Therefore, an ordinary visible picture image is color-displayed in the monitor.

On the other hand, when the filter switching device 451 is controlled by the above mentioned switching circuit 143 to interpose the inner peripheral side of the rotary filter 450 into the illuminating light path between the lamp 121 and the entrance end of the light guide 114, the light emitted from the above mentioned lamp 121 will pass in turn through the filters 450d, 450e and 450f transmitting respectively UV1, IR1 and IR2 of the above mentioned rotary filter 450 and will be divided in time series into light of the respective wavelength ranges of UV1, IR1 and IR2. The light is are transmitted to the tip part 9 through the light guide 114 and is radiated onto the object to be imaged. The returning light from the object by this illuminating light is made to form an image on the solid state imaging device 452 by the objective lens system 115 and the object is imaged by this solid state imaging device 452. Therefore, a picture image in invisible ranges such as the ultraviolet and infrared light ranges by the respective wavelength ranges of UV1, IR1 and IR2 is displayed in quasi colors in the monitor 7. When one or two of the memories 136a, 136b and 136c are selectively read out, a picture image by one or two wavelength ranges of UV1, IR1 and IR2 will be able to be obtained.

Thus, according to this embodiment, the same as in the other embodiments, not only an ordinary visible color picture image but also a picture image in invisible ranges such as the ultraviolet and infrared light ranges can be obtained.

The transmitted wavelength ranges of the respective filters provided on the outer peripheral side and inner peripheral side of the above mentioned rotary filter 450 are not limited to be as in this embodiment but can be set freely.

The present invention is not limited to the above mentioned respective embodiments. For example, the reflected light from the observed object is not limited to be received but the light having passed through the object may be received.

The present invention can be applied to others than the endoscope.

The present invention has effects that visible information can be obtained by selecting an optimum wavelength range in response to the observed object and the color tone difference in the respective positions of the observed object difficult to discriminate in the picture image in the general visible range can be easily detected.

In this invention, it is apparent that working modes different in a wide range can be formed on the basis of this invention without deviating from the spirit and scope of the invention. This invention is not restricted by its specific working modes except being limited by the appended claims.

What is claimed is:

1. An imaging apparatus for observing an object image of ordinary light and an object image of particular light comprising:

an illuminating means for emitting an illuminating light of a wavelength range ranging from a visible range to a range other than the visible range;

an image forming optical system for forming the object image to be imaged;

an imaging means having a sensitivity to a wavelength range ranging from the visible range to the range other than the visible range and using a solid state imaging device converting an image formed by said image forming optical system to an electric signal;

a color filter provided between said image forming optical system and said imaging means, said color filter separating said object image into images of a plurality of wavelength ranges, said color filter having a plurality of types of component filters, respective component filters having a transmitting characteristic of respectively transmitting the light of specific wavelength ranges within the visible band and the band other than the visible band;

a band dividing means for dividing the illuminating light into said visible band and said band other than the visible band, said band dividing means for selecting either band to select the wavelength range imaged by said imaging means and to obtain said object image of ordinary light or particular light; and a signal processing means for processing output signals of said imaging means in response to the wavelength ranges within a band selected by said band dividing means so as to be video signals.

2. An imaging apparatus according to claim 1 wherein said specific wavelength ranges within said visible band transmitted by the respective component filters of said color filter are respectively different in said respective component filters, said specific wavelength ranges within said band other than the visible band transmitted by said respective component filters are the same specific wavelength ranges within the infrared band, said band dividing means include a filter selectively transmitting the visible band and infrared band.

3. An imaging apparatus according to claim 2, wherein said band dividing means includes a filter transmitting a narrow band insertable provided in the optical path from said illuminating means to said imaging means.

4. An imaging apparatus according to claim 2 further comprising an illuminating means for emitting a light of a narrow band interchangeably provided with said illuminating means for emitting the illuminating light of the wavelength range ranging from the visible range to the range other than the visible range.

* * * * *